US011883449B2

(12) United States Patent
Machado et al.

(10) Patent No.: US 11,883,449 B2
(45) Date of Patent: *Jan. 30, 2024

(54) METHOD FOR REDUCING TOTAL GAS PRODUCTION AND/OR METHANE PRODUCTION IN A RUMINANT ANIMAL

(71) Applicants: Commonwealth Scientific and Industrial Research Organisation, Acton (AU); Meat & Livestock Australia Limited, North Sydney (AU); James Cook University, Townsville (AU)

(72) Inventors: Lorenna Machado, Águas Claras/DF (BR); Marie Elisabeth Magnusson, Rosslea (AU); Nigel William Tomkins, Queensland (AU); Robert Douglas Kinley, Mysterton (AU); Peter Canisius Denys, Mysterton (AU); Nicholas Andrew Paul, Annadale (AU)

(73) Assignees: Commonwealth Scientific and Industrial Research Organisation, Acton (AU); Meat & Livestock Australia Limited, North Sydney (AU); James Cook University, Townsville (AU)

(*) Notice: Subject to any disclaimer, the term of this patent is extended or adjusted under 35 U.S.C. 154(b) by 221 days.

This patent is subject to a terminal disclaimer.

(21) Appl. No.: 17/103,106

(22) Filed: Nov. 24, 2020

(65) Prior Publication Data
US 2021/0077555 A1 Mar. 18, 2021

Related U.S. Application Data

(63) Continuation of application No. 15/991,546, filed on May 29, 2018, now Pat. No. 10,881,697, which is a continuation-in-part of application No. 15/113,172, filed as application No. PCT/AU2015/000030 on Jan. 21, 2015, now Pat. No. 9,980,995.

(30) Foreign Application Priority Data
Jan. 21, 2014 (AU) .............................. 2014900182

(51) Int. Cl.
*A61K 36/04* (2006.01)
*A61K 9/00* (2006.01)
*A23K 50/10* (2016.01)
*A23K 10/30* (2016.01)
*A61P 1/00* (2006.01)

(52) U.S. Cl.
CPC .............. *A61K 36/04* (2013.01); *A23K 10/30* (2016.05); *A23K 50/10* (2016.05); *A61K 9/0056* (2013.01); *A61P 1/00* (2018.01)

(58) Field of Classification Search
CPC .................. A23K 10/30; A61K 36/04
See application file for complete search history.

(56) References Cited

U.S. PATENT DOCUMENTS

2002/0022049 A1    2/2002  Allen et al.
2011/0287132 A1   11/2011  Eino et al.
2012/0177806 A1*   7/2012  Kraan ................... A23K 40/25
                                                              426/635

FOREIGN PATENT DOCUMENTS

CN      104 026 370          9/2014
FR        2 857 562 A1       1/2005
WO         03/072118 A1      9/2003
WO      2006/105634 A1      10/2006
WO    WO 2015/109362         7/2015

OTHER PUBLICATIONS

AlgaeBase "Asparagopsis armata Harvey 1855" 3 p. 2022 (Year: 2022).*
Machado et al., "Effects of marine and freshwater macroalgae on in vitro total gas and methane production," *PloS One*, 9(1);e85289/1-e85289/11, 2014.
Machado et al., "The potential of macroalgae for beef production systems in Northern Australia," *J. Appl. Phycol.*, 27:2001-2005, 2015.
Makkar et al., "Seaweeds for livestock diets: A review," *Animal Feed Science and Technology*, 212:1-17, 2016.
Montañez-Valdez et al., "Effect of a calcified-seaweed extract as rumen buffer on ruminal disappearance and fermentation in steers," *Indian Journal of Animal Sciences*, 82(4):430-432, 2012.
Office Communication issued in U.S. Appl. No. 16/321,070, dated Sep. 21, 2020.
PCT International Search Report and Written Opinion issued in International Application No. PCT/AU2016/050689, dated Sep. 1, 2016.
Nielsen et al., Anaerobic digestion of macroalgae: methane potentials, pre-treatment, inhibition and co-digestion, Water Sci. Technolog. (2011) 64(8): 1723-1729 (DOI: 10.2166/wst.2011.654).
International Search Report for International Patent Application No. PCT/AU2015/000030 dated Apr. 15, 2015, 5 pgs.
Office Action for Canadian Patent Application No. 2,937,580 dated Oct. 22, 2020, 6 pages.
Examination Report 1 for New Zealand Patent Application No. 722423 dated Oct. 27, 2020, 3 pages.
Bach, S.J. et al., "Effect of feeding sun-dried seaweed (*Ascophyllum nodosum*) on fecal shedding of *Escherichia coli* O157:H7 by feedlot cattle and on growth performance of lambs", Anima Feed Science and Technology, 142: 17-32 (2008).
Cottyn, B. et al., "Rapid Method for the Gas-Chromatographic Determination of Volatile Fatty Acids in Rumen Fluid", National Institute for Animal Nutrition, 16(1): 105-107 (1968).
Dubois, B. et al. "Effect of Tropical Algae as Additives on Rumen in vitro Gas Production and Fermentation Characteristics", American Journal of Plant Sciences, 4: 34-43 (2013).

(Continued)

*Primary Examiner* — Thane Underdahl
(74) *Attorney, Agent, or Firm* — Daniel R. Evans; Merchant & Gould P.C.

(57) ABSTRACT

The present invention relates to a method of reducing total gas production and/or methane production in a ruminant animal.

19 Claims, 25 Drawing Sheets

(56) References Cited

OTHER PUBLICATIONS

Goering, H. et al., Forage Fiber Analyses (Apparatus, Reagents, Procedures, and Some Applications), Agriculture Handbook, U.S. Agricultural Research Service, 379: 24 pgs (1970).

Hino, T. et al., "Maintenance of Protozoa and Methanogens, and Fiber Digestion in Rumen-Simulating Continuous Culture", J. Gen. Appl. Microbiol., 39: 35-45 (1993).

Kinley, R.D. et al., "In vitro evaluation of feeding North Atlantic Stormtoss seaweeds on ruminal digestion", Journal of Applied Phycology, 27: 2387-2393 (2014).

Li, X., "Eremophila glabra reduces methane production in sheep", The University of Western Australia, School of Animal Biology, 113 pgs (2013).

Machado, L. et al., "Effects of Marine and Freshwater macroalgae on In Vitro Total Gas and Methane Production", PLOS One, 9(1): 1-11 (2014).

Ottenstein, D.M. et al., "Separation of Free Acids C2-C5 in Dilute Aqueous Solution Column Technology", Journal of Chromatographic Science, 9: 673-681 (1971).

Playne, M., "Determination of Ethanol, Volatile Fatty Acids, Lactic and Succinic Acids in Fermentation Liquids by Gas Chromatography", J. Sci. Food Agric., 36: 638-644 (1985).

Rai, S.N. et al., "Chemical composition and mineral profiles of certain sea weeds of Indian Coast",. Indian Journal of Animal Sciences, 78(11): 1278-1280 (2008).

Wang, J.K. et al., "Feastibility of Porphyra haitanensis as protein source for ruminants", 16(2): 278-283 (2008).

Chinese Office Action for Chinese Patent Application No. 202010297937.5 dated Jul. 28, 2021, 10 pages.

Examination Report for New Zealand Patent Application No. 722423 dated Nov. 17, 2020, 4 pages.

Examination Report for New Zealand Patent Application No. 722423 dated May 6, 2021, 5 pages.

Borowitzka, M. et al., "Algae as food", Microbiology of Fermented Foods, 585-602 (1998).

Manailal, A. et al., "In vivo therapeutic potentially of red seaweed, Asparagopsis (Bonnemaisoniales, Rhodophyta) in the treatment of Vibriosis in Penaeus monodon Fabricius", Saudi Journal of Biological Sciences, 19: 165-175 Dec. 2011).

Novaczek, I., "A Guide to the Common Edible and Medicinal Sea Plants of the Pacific Islands", Community Fisheries Training Pacific Series—3A, ISBN 982-203-835-6, 1-40 (Mar. 2001).

\* cited by examiner

METHOD FOR REDUCING TOTAL GAS PRODUCTION AND/OR METHANE PRODUCTION IN A RUMINANT ANIMAL

This application is a Continuation of U.S. patent application Ser. No. 15/991,546, filed 29 May 2018, which is a Continuation-in-Part of U.S. patent application Ser. No. 15/113,172, filed 21 Jul. 2016, now U.S. Pat. No. 9,980,995, which is a National Stage Application of PCT/AU2015/000030, filed 21 Jan. 2015, which claims benefit of Serial No. 2014900182, filed 21 Jan. 2014 in Australia and which applications are incorporated herein by reference. To the extent appropriate, a claim of priority is made to each of the above-disclosed applications.

FIELD OF THE INVENTION

The present invention relates to a method of reducing total gas production and/or methane production in a ruminant animal.

BACKGROUND OF THE INVENTION

Methane ($CH_4$) is a greenhouse gas (GHG) produced primarily by methanogenic microbes that are found in natural ecosystems (e.g. wetlands, oceans and lakes) and the gastrointestinal tract of invertebrates and vertebrates, such as termites and ruminants. Every year ~429-507 Tg of $CH_4$ are removed from the atmosphere and ~40 Tg from the stratosphere through reactions with hydroxyl (OH) radicals; and ~30 Tg by $CH_4$-oxidizing bacteria in soil.

Nevertheless, anthropogenic GHG emissions have been increasing rapidly, with the $CH_4$ concentration in the atmosphere now more than twofold higher than in the early 1800s. Methane is very effective in absorbing solar infrared radiation and has a global warming potential 25 times greater than $CO_2$. Consequently, its accumulation in the atmosphere contributes considerably to climate change. One of the main sources of anthropogenic $CH_4$ can be attributed to agricultural activities, including ruminant livestock.

According to a recent UN report, cattle-rearing generates more global warming greenhouse gases, as measured in $CO_2$ equivalent, than transportation. In Australia, ruminants are estimated to contribute ~10% of the total GHG emissions. Ruminants produce $CH_4$ as a by-product of the anaerobic microbial fermentation of feeds in the rumen and, to a lesser extent, in the large intestine. The ruminal microbial community is highly diverse and composed of bacteria, protozoa, fungi, and bacteriophages that act collectively to ferment ingested organic matter (OM), resulting in $CO_2$, $H_2$, volatile fatty acids (VFAs), and formates. Methanogenic archaea present in the rumen use these end-products and produce $CH_4$. Although the production of $CH_4$ reduces the partial pressure of $H_2$, which could otherwise inhibit rumen fermentation, it also reduces the amount of energy and carbon available for formation of VFAs essential for ruminant nutrition. Most of the $CH_4$ produced in ruminants is exhaled and belched by the animal and represents a loss of up to 12% of gross energy intake.

Mitigation strategies that reduce enteric $CH_4$ formation are important, and methods of reducing total gas production and/or methane production in ruminant animals represent a major challenge.

SUMMARY OF THE INVENTION

In one aspect, the present invention provides a method for reducing total gas production and/or methane production in a ruminant animal comprising the step of administering to said ruminant animal an effective amount of at least one species of red marine macroalgae.

In one embodiment the species of red marine macroalgae is an *Asparagopsis* species. In another embodiment, the species of *Asparagopsis* is *A. taxiformis*.

In one embodiment, the effective amount of at least one species of red marine macroalgae is administered to said ruminant animal by supplementing food intended for said animal with said effective amount of at least one species of red marine macroalgae.

In another aspect, the present invention provides a method for reducing total gas production and/or methane production in a ruminant animal comprising the step of administering to said ruminant animal an effective amount of at least one species of red marine macroalgae, wherein effective levels of desirable volatile fatty acids are maintained.

In one embodiment, the ratio of acetate to propionate is decreased.

In another embodiment the level of organic matter and/or dry matter degraded is maintained.

In a further embodiment, the at least one species of red marine macroalgae is administered at a dose of at least 3, 2, 1, 0.5, 0.25 0.125 or 0.067% of the organic matter administered to the ruminant animal.

In another aspect, the amount of total gas produced by ruminal fermentation in vitro is reduced by at least 61% relative to the amount of total gas produced when decorticated cottonseed is subjected to ruminal fermentation in vitro.

In a further aspect, the methane production in the ruminant animal is reduced by at least 10% relative to the amount of methane produced by a ruminant animal administered decorticated cottonseed.

In a further aspect, the methane production in the ruminant animal is reduced by at least 15% relative to the amount of methane produced by a ruminant animal administered decorticated cottonseed.

In another aspect, the amount of methane produced by ruminal fermentation in vitro is reduced by at least 98.8% relative to the amount of methane produced when decorticated cottonseed is subjected to ruminal fermentation in vitro.

In a further aspect, the methane production in the ruminant animal is reduced by at least 83% relative to the amount of methane produced by a ruminant animal administered a lupin diet.

In one embodiment, said ruminant animal is selected from the members of the Ruminantia and Tylopoda suborders. In another embodiment, said ruminant animal is cattle or sheep. In a further embodiment, said ruminant animal is a cattle.

In another embodiment, method further comprises administering to said ruminant animal an effective amount of at least one species of macroalgae is selected from the group consisting of *Asparagopsis armata*, *Asparagopsis taxiformis*, *Dictyota* spp (e.g. *Dictyota bartayresii*), *Oedogonium* spp, *Ulva* spp, and *C. patentiramea*.

In another aspect the present invention also provides a feed supplement for reducing total gas production and/or methane production in a ruminant animal, said supplement comprising an effective amount of at least one species of red marine macroalgae. In one embodiment the species of red marine macroalgae is an *Asparagopsis* species. In another embodiment, the species of *Asparagopsis* is *A. taxiformis*.

In another embodiment, the supplement further comprises an effective amount of at least one species of macroalgae selected from the group consisting of *Asparagopsis armata*,

*Asparagopsis taxiformis*, *Dictyota* spp (e.g. *Dictyota bartayresii*), *Oedogonium* spp, *Ulva* spp, and *C. patentiramea*.

In another aspect, the present invention also provides a feed for a ruminant animal, wherein said feed is supplemented with a feed supplement described herein.

In another aspect the present invention provides a method for reducing methane production by a ruminant animal, said method comprising the step of administering to said animal a feed supplement described herein or a feed described herein.

DETAILED DESCRIPTION

Figure 1:
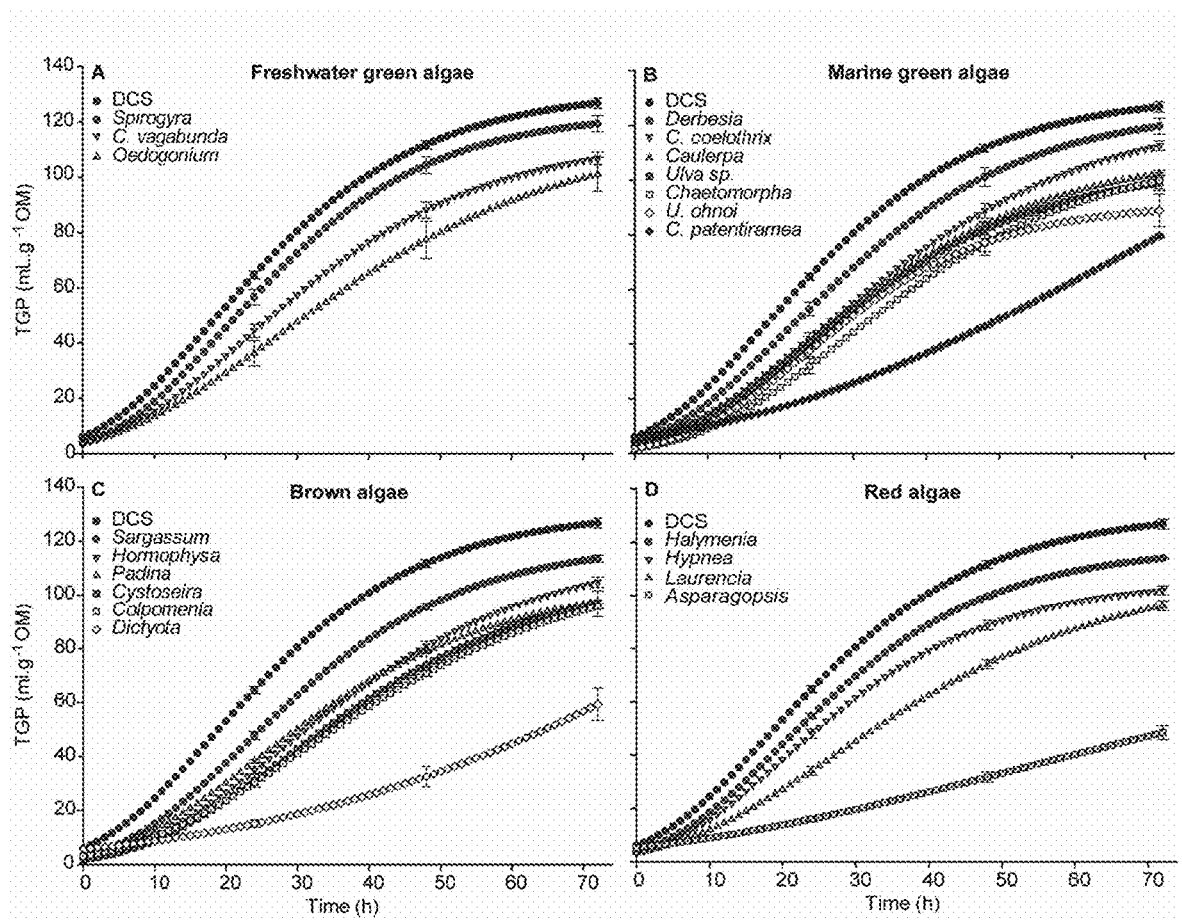
FIG. 1 shows total gas production (TGP) (ml·g$^{-1}$ OM) from anaerobic fermentation in vitro in the presence of macroalgae species over the 72 h incubation period. Error bars represent ±SE (n=4). Species full names are given in Table 1. This figure demonstrates *Dictyota* and *Asparagopsis* spp. reduce total gas production from anaerobic fermentation.
Figure 2:
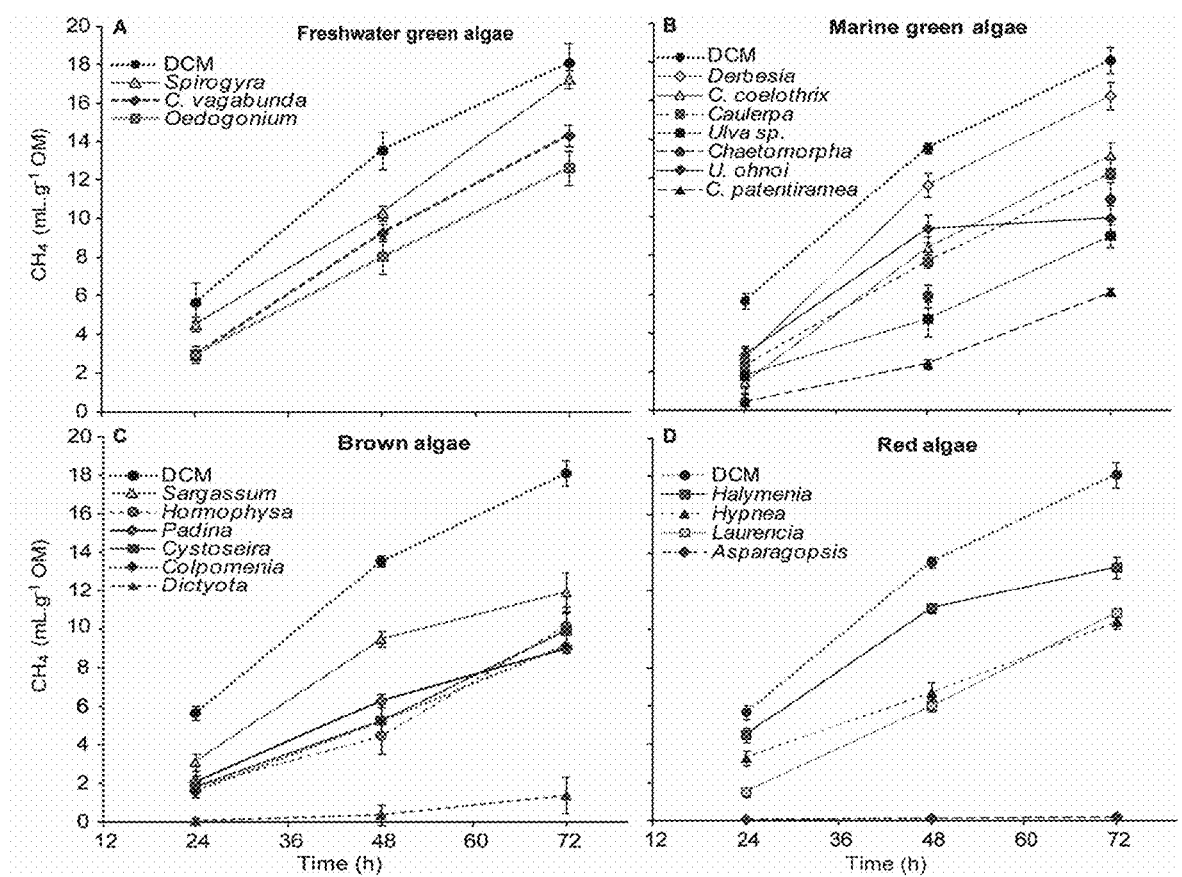
FIG. 2 shows methane ($CH_4$) production (ml·g$^{-1}$ OM) from anaerobic fermentation in vitro in the presence of macroalgae species at 24, 48, and 72 h. Error bars represent ±SE (n=3-4). Species full names are given in Table 1. This figure demonstrates *Dictyota* and *Asparagopsis* spp. reduce methane production from anaerobic fermentation.

The present invention relates to a method for reducing total gas production (TGP) and/or methane ($CH_4$) production by a ruminant animal. In particular, the present inventors have shown that red marine macroalgae possess the property of reducing methane production in ruminant animals.

FIGS. 1, 6, 7 and 25 show a reduction of total gas produced in vitro from anaerobic fermentation (also referred to herein as ruminal fermentation) in the presence of red marine macroalgae. FIGS. 2, 10, 11, 23 and 24 show a reduction of methane produced in vitro from anaerobic fermentation in the presence of red marine macroalgae. FIGS. 14, 15, 18 and 19 show a reduction of methane produced in vivo in ruminant animals administered red marine macroalgae.

The invention therefore relates to a method for reducing total gas production and/or methane production in a ruminant animal comprising the step of administering to said ruminant animal an effective amount of at least one species of red marine macroalgae.

In one embodiment, the species of red marine macroalgae belong to the genus *Asparagopsis*.

As used herein, the term "reducing" includes the reduction of amount of substance in comparison with a reference. For example, the reduction in the amount of total gas and/or methane produced by a ruminant animal or animals administered a composition comprising a red marine macroalgae according to the present invention, relative to an animal or animals not administered a composition comprising a red marine macroalgae composition of the present invention. The reduction can be measured in vitro with an artificial rumen system that simulates anaerobic fermentation, or in vivo with animals confined in respiration chambers. It is within the knowledge and skill of those trained in the art to assess enteric methanogenesis by a ruminant animal.

As used herein the term "anaerobic fermentation" is intended to include anaerobic fermentation in vivo, for example, in a ruminant animal.

As used herein, the term 'reducing total gas production' refers to the reduction of the total amount of gas produced, for example the amount of total gas produced in the gastrointestinal tract. The term includes the collective volume of all gasses generated as a result of anaerobic fermentation, for example, in the systems described herein. Fermentation in the rumen and the gut of a ruminant gives rise to production of gas including methane. The present invention aims to reduce this process, such as to reduce the total amount of gas produced in the gastro-intestinal tract. It is within the knowledge and skill of those trained in the art to assess total gas production by a ruminant animal.

As used herein, the term 'reducing methane production' refers to the reduction of methane produced in the gastrointestinal tract. The term includes the specific volume of methane generated as a result of anaerobic fermentation, for example, in the systems described herein. Fermentation in the rumen and the gut of a ruminant gives rise to production of methane. The present invention aims to reduce this process, such as to reduce the total amount of methane produced in the gastro-intestinal tract. It is within the knowledge and skill of those trained in the art to assess methane production by a ruminant animal.

The present study provides the first evidence that macroalgae can effectively reduce methane production, and the present inventors have demonstrated that all species had similar or lower TGP and $CH_4$ production relative to a positive control of decorticated cottonseed (DCS). Importantly, decorticated cottonseed is used as a feed supplement for cattle because it considerably reduces $CH_4$ production compared to other high energy grains. The reduction in total gas production, compared to DCS, was similar among species, indicating macroalgae reduce ruminant TGP and $CH_4$ production relative to high energy grains, and some macroalgae reduce ruminant TGP and $CH_4$ production relative to the DCS positive control.

For example, the present inventors have shown *Cladophora patentiramea* had the lowest TGP of the marine green macroalgae, producing a total of 79.7 mL·g$^{-1}$ OM (FIG. 1b). *Dictyota* was the most effective species of brown macroalgae, reducing TGP to 59.4 mL·g–1 OM after 72 h (FIG. 1c), resulting in a significantly lower TGP (53.2%) than for the decorticated cottonseed (DCS) positive control (FIG. 1c, Tukey's HSD 72 h, p<0.0001). This effect was even greater at 24 h (TGP=76.7% lower than DCS). Other brown macroalgae reduced TGP by >10%, with *Padina*, *Cystoseira*, and *Colpomenia* significantly reducing TGP compared to DCS (Table 2, Tukey's HSD 72 h, p<0.02). The most effective of all macroalgae was the red alga *Asparagopsis* (FIG. 1d) with the lowest TGP, 48.4 mL·g–1 OM.

Furthermore, the present inventors have shown $CH_4$ production generally followed the same pattern as TGP described above and in the Examples, and notably $CH_4$ production was directly and significantly correlated with TGP values. For example, the positive control DCS had the highest $CH_4$ output, producing 18.1 mL·g$^{-1}$ OM at 72 h. *Asparagopsis, Dictyota* and *C. patentiramea* also had the most pronounced effect on reducing in vitro $CH_4$ production. *C. patentiramea* had a $CH_4$ output of 6.1 mL·g–1 OM (Table 1) and produced 66.3% less $CH_4$ than DCS (FIG. 2b, Tukey's HSD 72 h, p<0.0001). *Dictyota* produced 1.4 mL·g$^{-1}$ OM and was the most effective of the brown macroalgae, reducing $CH_4$ output by 92% (FIG. 2c, Table 2, Tukey's HSD 72 h, p<0.001), and the concentration of $CH_4$ within TGP, 23.4 mL·L–1, by 83.5% compared to DCS (Table 2).

*Asparagopsis* had the lowest $CH_4$ output among all species of macroalgae producing a maximum of 0.2 mL·g–1 OM throughout the incubation period (Table 2, Tukey's HSD 72 h, p<0.001). This is a reduction of 98.9% on CH4 output compared to DCS (FIG. 2d), independently of time. Notably, *Asparagopsis* also had the lowest concentration of $CH_4$ within TGP producing only 4.3 mL·L$^{-1}$ of $CH^4$ per litre of TGP after 72 h, making it distinct from all other species (Table 2).

In preferred embodiments of the invention, the amount of total gas produced is reduced by at least 90%, 80%, 70%, 61%, 60%, 50%, 40%, 30%, 20% or 10% compared to a reference. In one embodiment the reference is the amount of total gas produced when animals are not administered an effective amount of at least one species of red marine macroalgae. In another embodiment, the reference is the amount of total gas produced when animals are administered decorticated cottonseed. In another embodiment, the reference is the amount of total gas produced when decorticated cottonseed is subjected to in vitro anaerobic fermentation.

In one embodiment, the amount of total gas produced by ruminal fermentation in vitro is reduced by at least 61.8% relative to the amount of total gas produced when decorticated cottonseed is subjected to ruminal fermentation in vitro.

In preferred embodiments of the invention, the amount of methane produced is reduced by at least 90%, 80%, 70%, 61%, 60%, 53%, 50%, 40%, 30%, 20%, 15%, 11% or 10% compared to a reference. In one embodiment the reference is the amount of methane produced when animals are not administered an effective amount of at least one species of red marine macroalgae. In another embodiment, the reference is the amount of methane produced when animals are administered decorticated cottonseed. In another embodiment, the reference is the amount of methane produced when animals are administered a pelleted commercial shipper ration based on lupins, oats, barley, wheat with cereal straw as the roughage component [chemical composition (g/kg DM) of ash, 72; crude protein (CP) 112; neutral detergent fibre (aNDFom) 519; acid detergent fibre (ADFom) 338, and free of cobalt, selenium and rumen modifiers], with an additional amount of crushed lupins referred to herein as 'a lupin diet'. In another embodiment, the reference is the amount of methane produced when a lupin diet is subjected to in vitro anaerobic fermentation.

In one embodiment, the amount of methane produced by ruminal fermentation in vitro is reduced by at least 98.8% compared to the amount of methane produced when decorticated cottonseed is subjected to ruminal fermentation in vitro.

In one embodiment, the amount of methane produced is reduced by at least 10% compared to the amount of methane produced when a ruminant animal is administered decorticated cottonseed.

In one embodiment, the amount of methane produced is reduced by at least 15% compared to the amount of methane produced when a ruminant animal is administered decorticated cottonseed.

The present inventors have also demonstrated that *Asparagopsis* can effectively reduce methane production, relative to a positive control of a lupin diet in sheep. In one embodiment, the amount of methane produced is reduced by at least 53% compared to the amount of methane produced when a ruminant animal is administered a lupin diet.

By "effective amount", is meant a quantity of at least one species of red marine macroalgae sufficient to allow improvement, e.g. reduction in the amount of methane production in comparison with a reference or control, reduction in the amount of total gas produced in comparison with a reference or control, maintenance of effective levels of desirable volatile fatty acids in comparison with a reference or control, reduction in the acetate to propionate ratio in comparison with a reference or control, maintenance of liveweight, dry matter intake and/or organic matter intake in comparison with a reference or control. Within the meaning of the present invention, the methane reductive effect can be measured in the rumen with an artificial rumen system, such as that described in T. Hano., J. Gen. Appl. Microbiol., 39, 35-45, 1993 or by in vivo oral administration to ruminants.

Therefore, in one embodiment, the at least one species of red marine macroalgae is administered at a dose of preferably at least 16.67, 10, 5, 3, 2, 1, 0.5, 0.25 0.125 or 0.067% of the organic matter administered to the ruminant animal.

In a preferred embodiment, the at least one species of red marine macroalgae is administered at a dose of preferably at least 3, 2, 1, 0.5, 0.25 0.125 or 0.067% of the organic matter administered to the ruminant animal.

For example, if a 450 kg ruminant animal (e.g. steer) consumes 2.5% to 3% of its body weight per day of feed, then the at least one species of red marine macroalgae is administered at a dose proportional to the amount of organic matter administered to the ruminant. In the case of a 450 kg ruminant animal, and where 80% of the feed is organic matter, if the animal consumes about 2.5% of its body weight per day, then the at least one species of red marine macroalgae is administered at a dose of about 0.27, 0.18, 0.09, 0.045, 0.0225, 0.01125 or 0.00603 kg per day to result in a dose at least 3, 2, 1, 0.5, 0.25 0.125 or 0.067% of the organic matter administered to the ruminant animal.

In the case of a 450 kg ruminant animal, if the animal consumes about 3% of its body weight per day, and where 80% of the feed is organic matter, then the at least one species of red marine macroalgae is administered at a dose of about 0.324, 0.216, 0.108, 0.054, 0.027, 0.0135 or 0.007236 kg per day to result in a dose at least 3, 2, 1, 0.5, 0.25 0.125 or 0.067% of the organic matter administered to the ruminant animal.

An effective amount of the at least one species of red marine macroalgae may be determined by the methods described herein, including the in vitro and in vivo dose-response studies described herein. For example, the present inventors have demonstrated that ruminal fermentation in vitro can be used to examine the effect of amounts of the at least one species of red marine macroalgae on levels of volatile fatty acids, including acetate and propionate, methane production, and total gas production. Therefore, ruminal fermentation in vitro can be used to characterize doses of the at least one species of red marine macroalgae that may be an effective amount sufficient to allow improvement, e.g. reduction in the amount of methane production in comparison with a reference or control, reduction in the amount of total gas produced in comparison with a reference or control, maintenance of effective levels of desirable volatile fatty acids in comparison with a reference or control, or reduction in the acetate to propionate ratio in comparison with a reference or control.

A ruminant is a mammal of the order Artiodactyla that digests plant-based food by initially softening and partially fermenting it within the animal's first stomach chambers, then regurgitating the semi-digested mass, now known as cud, and chewing it again.

The process of rechewing the cud to further break down plant matter and stimulate digestion is called "ruminating". Ruminants have a digestive tract with four chambers, namely the rumen, reticulum, omasum and abomasum. In the first two chambers, the rumen and the reticulum, the food is mixed with saliva and separates into layers of solid and liquid material. Solids clump together to form the cud, or bolus. The cud is then regurgitated, chewed slowly to completely mix it with saliva, which further breaks down fibers. Fiber, especially cellulose, is broken down into glucose in these chambers by symbiotic anaerobic bacteria, protozoa and fungi. The broken-down fiber, which is now in the liquid part of the contents, then passes through the rumen into the next stomach chamber, the omasum. The food in the abomasum is digested much like it would be in the monogastric stomach. Digested gut contents are finally sent to the small intestine, where the absorption of the nutrients occurs. Almost all the glucose produced by the breaking down of cellulose is used by the symbiotic bacteria. Ruminants get their energy from the volatile short chain fatty acids (VFAs) produced by the bacteria, namely acetate, propionate, butyrate, valerate, and isovalerate.

Importantly, the inventors have shown that red marine macroalgae possess the property of reducing total gas production and/or methane production in ruminant animals without compromising rumen fermentation.

For example, the inventors have shown that red marine macroalgae possess the property of reducing total gas production and/or methane production in ruminant animals without compromising rumen fermentation, for example, while maintaining effective levels of desirable volatile fatty acids.

The inventors have also shown that red marine macroalgae possess the property of reducing total gas production and/or methane production in ruminant animals without compromising rumen fermentation, for example, while not significantly affecting daily feed intakes and/or animal liveweight.

As used herein, the term "effective levels", includes an amount of substance in an animal or animals following treatment (e.g. administration of the at least one species of red marine macroalgae) that is not significantly differ significantly from a control or reference, including the amount of substance in an animal or animals not administered a composition comprising a red marine macroalgae composition of the present invention.

For example, an "effective amount of volatile fatty acids" is intended to include the amount of one or more volatile fatty acids produced by a ruminant animal or animals not administered a composition comprising a red marine macroalgae according to the present invention.

Carbohydrate metabolism provides energy for the growth of rumen microbes primarily through the fermentation of cellulose and starch. The insoluble polymers are converted to oligosaccharides and soluble sugars by extracellular enzymes from the rumen microorganisms. The resulting sugars are then fermented to one of various forms of volatile fatty acids, carbon dioxide and hydrogen. As used herein, the volatile fatty acids—acetic acid, propionic acid and butyric acid—are also referred to as acetate, propionate and butyrate, respectively.

Volatile fatty acids are utilized by the animal as primary carbon and energy sources with varying degrees of efficiency. High levels of propionic acid are desirable because propionic acid is a primary metabolic precursor for gluconeogenesis in the animal. The fermentation of 6-carbon sugars to acetic acid is relatively inefficient since in this process, carbon and hydrogen are lost via eructation in the form of carbon dioxide or importantly, methane. On the other hand, the production of propionic acid utilizes hydrogen and does not result in a loss of carbon or methane.

It becomes possible then to improve feed utilization efficiency and/or the rate of growth of ruminant animals by increasing the molar proportion of propionic acid relative to acetic acid, or in another embodiment, by increasing total volatile fatty acid concentration (i.e. the sum of acetic, propionic and butyric acids) in the rumen.

Figure 13:
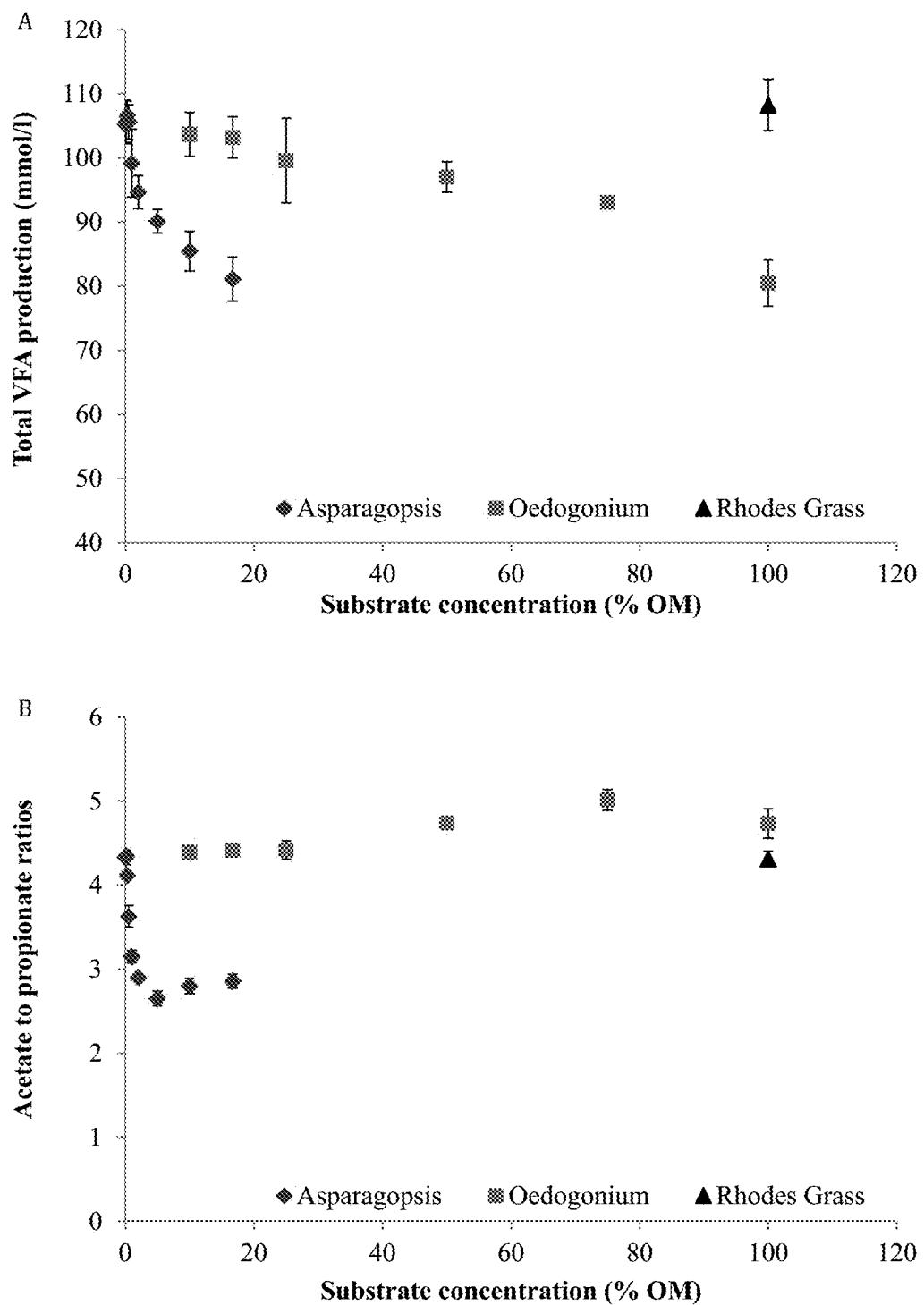
FIG. 13 shows the mean total volatile fatty acid (VFA) production (A) and acetate to propionate (B) ratios in a dose-response experiment in vitro. This figure demonstrates *Asparagopsis* does not reduce the amount of VFAs at doses of *Asparagopsis* that inhibit total gas and methane production. This figure also demonstrates *Asparagopsis* does not reduce the amount of VFAs at doses of *Asparagopsis* that do not reduce the amount of organic matter or dry matter degraded from anaerobic fermentation. This figure also demonstrates *Asparagopsis* decreases the acetate to propionate ratio at doses of *Asparagopsis* that inhibit total gas and methane production. In conjunction with Table 8, this data also demonstrates *Asparagopsis* increases the amount of propionate at doses of *Asparagopsis* that do not reduce the amount of organic matter or dry matter degraded from anaerobic fermentation. In conjunction with Table 8, this figure also demonstrates *Asparagopsis* decreases the amount of acetate at doses of *Asparagopsis* that do not reduce the amount of organic matter or dry matter degraded from anaerobic fermentation.
Figure 17:
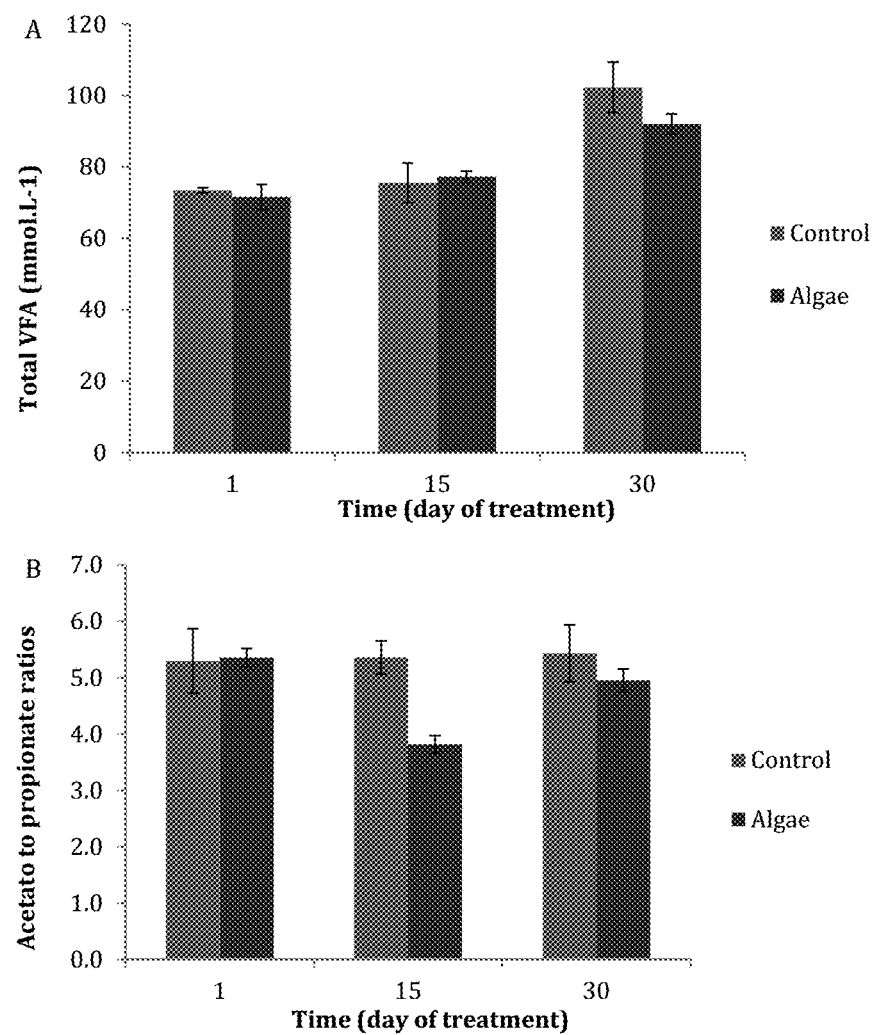
FIG. 17 shows mean total volatile fatty acid (VFA) production (A) and acetate to propionate ratios (B) of steers. Error bars represent ±SE (n=2). This figure demonstrates *Asparagopsis* does not reduce the amount of total VFA production (an indicator of rumen function) at doses of *Asparagopsis* that inhibit methane production in vivo. This figure also demonstrates *Asparagopsis* does not reduce the amount of total VFA at doses of *Asparagopsis* that do not reduce the amount of dry matter intake in vivo. This figure also demonstrates *Asparagopsis* decreases the ratio of acetate to propionate at doses of *Asparagopsis* that inhibit total gas and methane production after 15 and 30 days of treatment. This figure also demonstrates *Asparagopsis* decreases the ratio of acetate to propionate at doses of *Asparagopsis* that do not reduce the amount of organic matter or dry matter intake.
Figure 20:
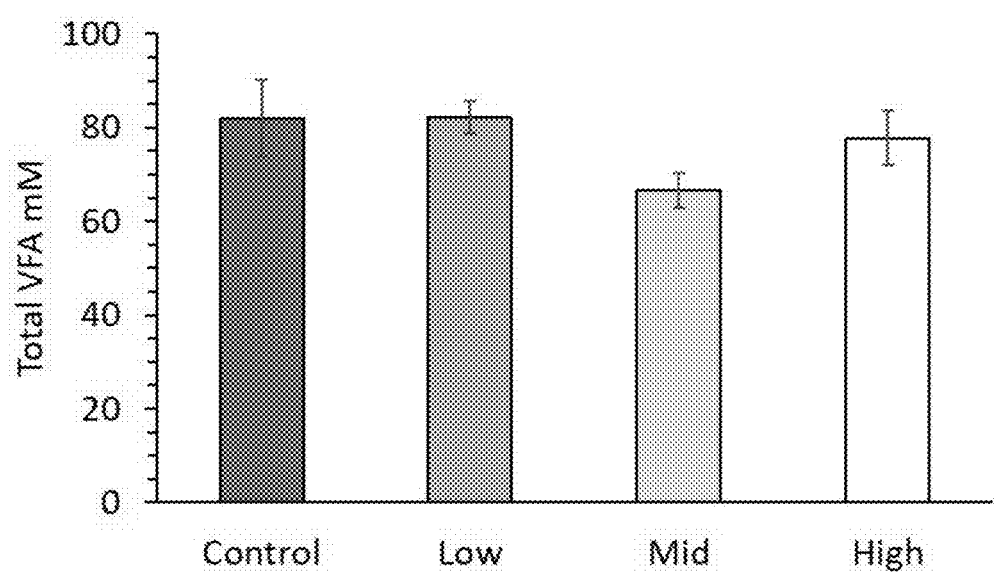
FIG. 20 shows changes induced in total volatile fatty acid (TVFA) concentration in rumen fluid extracted from Brangus steers consuming a feedlot total mixed ration with *Asparagopsis taxiformis* included at 4 dose levels (0.00, 0.05, 0.10, and 0.20% of organic matter intake). Columns are not identified with different letters because they were not significantly different at $P<0.05$. This figure demonstrates *Asparagopsis* does not reduce the amount of total VFAs, including at doses of *Asparagopsis* that reduce methane production in vivo.

The present inventors have demonstrated a reduction of total gas produced and/or methane produced in anaerobic fermentation in vitro and in vivo in the presence of red marine macroalgae, without negatively affecting total VFA production in cattle. FIG. 13 A shows *Asparagopsis* maintains effective levels of VFAs during anaerobic fermentation in vitro. This figure also demonstrates *Asparagopsis* decreases the acetate to propionate ratio at doses of *Asparagopsis* that inhibit total gas and methane production. In conjunction with Table 8, this data also demonstrates *Asparagopsis* decreases the amount of acetate, and increases the amount of propionate, at doses of *Asparagopsis* that do not reduce the amount of organic matter or dry matter degraded from anaerobic fermentation. FIG. 17 demonstrates *Asparagopsis* does not negatively affect the amount of VFAs at doses of *Asparagopsis* that inhibit methane production in vivo in cattle, and doses of *Asparagopsis* that do not reduce the amount of dry matter intake in vivo. This data also demonstrates *Asparagopsis* decreases the ratio of acetate to propionate at doses of *Asparagopsis* that inhibit total gas and methane production at 15 and 30 days of treatment, and *Asparagopsis* decreases the ratio of acetate to propionate at doses of *Asparagopsis* that do not reduce the amount of organic matter or dry matter intake. FIG. 20 demonstrates *Asparagopsis* does not negatively affect the amount of VFAs at doses of *Asparagopsis* that inhibit methane production in vivo in cattle.

Importantly, the present inventors have shown *Asparagopsis* does not reduce the amount of VFAs in cattle; at doses of *Asparagopsis* that do not reduce the amount of organic matter or dry matter intake/degradation; at doses that decrease the acetate to propionate ratio; at doses that decrease the amount of actetate; at doses that increase the amount of propionate; and/or at doses of *Asparagopsis* that inhibit total gas and methane production, in vitro and in vivo.

Importantly, the present inventors have demonstrated *Asparagopsis* does not reduce the amount of VFAs at doses of *Asparagopsis* that inhibit total gas and methane production in cattle.

The present inventors have also shown *Asparagopsis* does not reduce the amount of organic matter or dry matter intake/degradation in sheep; at doses that decrease the acetate to propionate ratio; at doses that decrease the amount of actetate; at doses that increase the amount of propionate; and/or at doses of *Asparagopsis* that inhibit methane production, in vitro and in vivo. For example, the present inventors have shown *Asparagopsis* does not reduce the amount of organic matter or dry matter intake/degradation in sheep fed 1.2 times maintenance energy.

Figure 18:
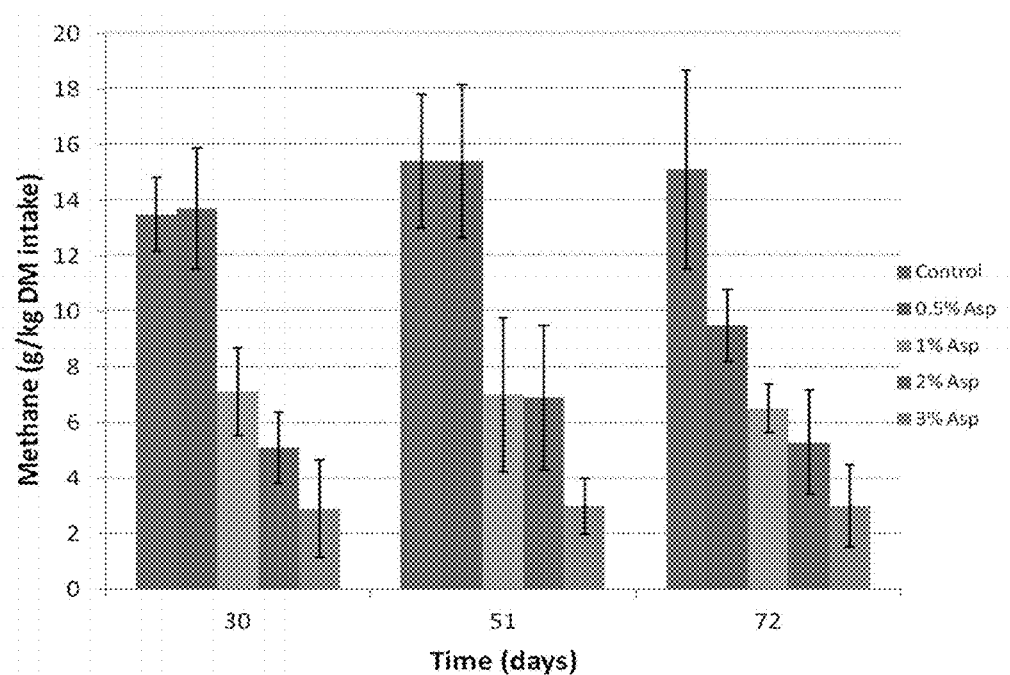
FIG. 18 shows mean methane production in $g \cdot kg^{-1}$ DMI for sheep fed a pelleted diet supplemented with or without *Asparagopsis* on a daily basis. Different doses of *Asparagopsis* (as a % of organic matter) as shown. This figure demonstrates *Asparagopsis* reduces methane production in vivo. A dose response was significant, with increasing doses of *Asparagopsis* (as a % of organic matter) above 0.5% OM basis, resulting in reductions in methane produced of between 53% and 80%. Error bars represent ±SE. In conjunction with Tables 10 and 11, this figure also demonstrates *Asparagopsis* reduces the amount of methane produced at doses of *Asparagopsis* that do not reduce the amount of organic matter or dry matter degraded from anaerobic fermentation, and that *Asparagopsis* reduces the amount of methane produced at doses of *Asparagopsis* that do not negatively affect the molar concentration of propionate, and which decrease the ratio of acetate to propionate.

In conjunction with Tables 10 and 11, FIG. 18 demonstrates *Asparagopsis* decreases the amount of acetate; increases the amount of propionate; and decreases the acetate to propionate ratio at doses of *Asparagopsis* that inhibit methane production in sheep.

In conjunction with Tables 10 and 11, FIG. 18 demonstrates *Asparagopsis* decreases the amount of acetate; increases the amount of propionate; and decreases the acetate to propionate ratio at doses of *Asparagopsis* that do not affect animal liveweight or daily feed intakes of sheep.

Figure 21:
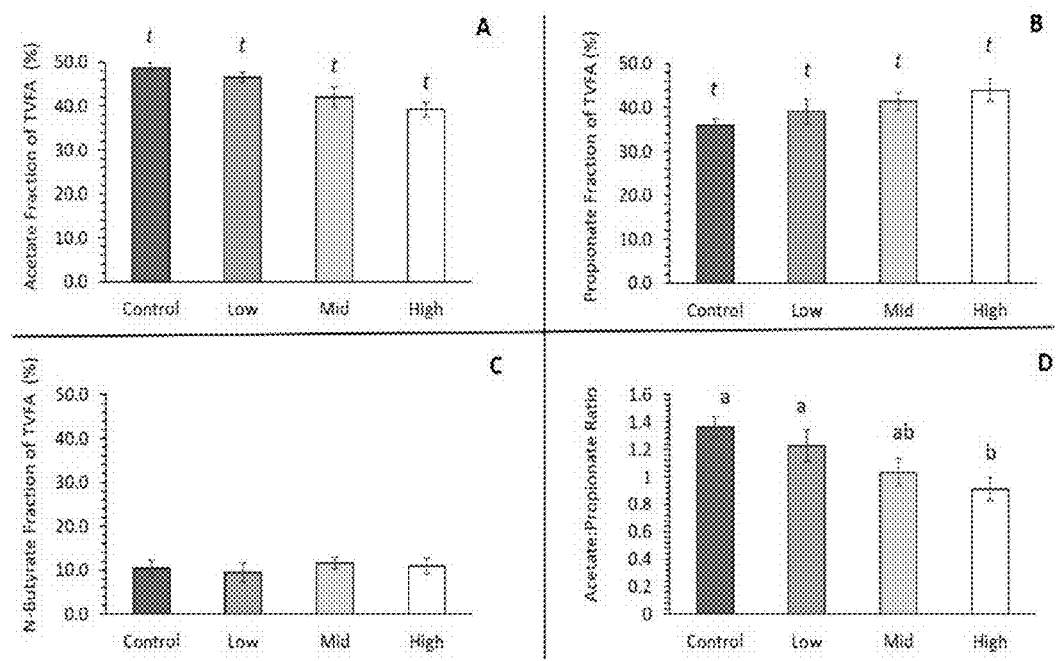
FIG. 21 shows Changes induced in acetate (A), propionate (B), and butyrate (C) the three major volatile fatty acids fractions of the total volatile fatty acids (TVFA) and the acetate to propionate ratio (D) in rumen fluid extracted from Brangus steers consuming a feedlot total mixed ration with increasing *Asparagopsis taxiformis* inclusion at 4 dose levels of 0.00, 0.05, 0.10, and 0.20% of organic matter intake. Columns identified with different letters were significantly different at $P<0.05$ and those with identified with a 't' were different as a trend at $P0.05$ and $P<0.10$. This figure demonstrates inclusion of *Asparagopsis* in feed results in a decrease in acetate (%) and increase in propionate (%) while maintaining total levels of VFAs, including at doses of *Asparagopsis* that inhibit methane production in vivo.

FIG. 21 demonstrates *Asparagopsis* decreases the amount of acetate; increases the amount of propionate; and decreases the acetate to propionate ratio at doses of *Asparagopsis* that inhibit methane production in vivo in cattle.

Therefore, in one aspect, the invention relates to a method for reducing total gas production and/or methane production in a ruminant animal comprising the step of administering to said ruminant animal an effective amount of at least one species of red marine macroalgae, wherein effective levels of desirable volatile fatty acids are maintained.

In one embodiment, the desirable volatile fatty acids are acetate and propionate.

As used herein, the term "volatile fatty acids" ("VFA") includes the end product of anaerobic microbial fermentation of feed ingredients in the rumen. The common VFAs include acetate, propionate, butyrate, isobutyrate, valerate, and isovalerate. The VFA's are absorbed by the rumen and used by the animal for energy and lipid synthesis.

In preferred embodiments of the invention, the total VFA produced in ruminal fermentation in the presence of an effective amount at least one species of red marine macroalgae is at least 80 mmol/L.

In other embodiments of the invention, the total VFA produced in ruminal fermentation in the presence of an effective amount at least one species of red marine macroalgae is at least 65 mmol/L.

The present inventors have also demonstrated that *Asparagopsis* does not reduce the amount of VFAs in cattle at doses of *Asparagopsis* that do not reduce the amount of organic matter or dry matter degraded from ruminal fermentation, or dry matter intake. The present inventors have also demonstrated that *Asparagopsis* does not reduce the amount of dry matter intake or liveweight of sheep. For example, the present inventors have demonstrated that *Asparagopsis* does not reduce the amount of dry matter intake or liveweight of sheep fed at 1.2 times maintenance energy. This indicates that red marine macroalgae reduce total gas production and/or methane production in ruminant animals without compromising rumen fermentation.

Therefore, in one aspect, the invention relates to a method for reducing total gas production and/or methane production in a ruminant animal comprising the step of administering to said ruminant animal an effective amount of at least one species of red marine macroalgae, wherein the amount of organic matter and/or dry matter degraded is maintained. In another aspect, the invention relates to a method for reducing total gas production and/or methane production in a ruminant animal comprising the step of administering to said ruminant animal an effective amount of at least one species of red marine macroalgae, wherein the amount of dry matter intake is maintained.

As used herein the terms, "organic matter" and "dry matter" means the amount of feed (on an organic or moisture-free basis, respectively) that an animal consumes in a given period of time, typically 24 hours. It is known in the art how to calculate organic matter and dry matter intake and/or degradation. For example, dry matter and organic matter may be 90% and 80% of the amount of feed, respectively In one embodiment, the at least one species of red marine macroalgae is administered at a dose of preferably at least 16.67, 10, 5, 3, 2, 1, 0.5, 0.25 0.125 or 0.067% of the organic matter administered to the ruminant animal.

In a preferred embodiment, the at least one species of red marine macroalgae is administered at a dose of preferably at least 3, 2, 1, 0.5, 0.25 0.125 or 0.067% of the organic matter administered to the ruminant animal to maintain the amount of organic matter and/or dry matter degraded.

In another embodiment, both the amount of organic matter or dry matter degraded is maintained, and the effective levels of desirable volatile fatty acids are maintained.

In a preferred embodiment, the at least one species of red marine macroalgae is administered at a dose of preferably at least 3, 2, 1, 0.5, 0.25 0.125 or 0.067% of the organic matter administered to the ruminant animal to maintain effective levels of desirable volatile fatty acids.

Importantly, the present inventors have demonstrated that *Asparagopsis* increases the amount of propionate at doses of *Asparagopsis* that inhibit total gas and methane production, and *Asparagopsis* increases the amount of propionate at doses of *Asparagopsis* that do not reduce the amount of organic matter or dry matter degraded.

In another aspect, the invention relates to a method for reducing total gas production and/or methane production in a ruminant animal comprising the step of administering to said ruminant animal an effective amount of at least one species of red marine macroalgae, wherein the amount of organic matter or dry matter degraded is maintained and/or the ratio of acetate to propionate is decreased.

In a preferred embodiment, the at least one species of red marine macroalgae is administered at a dose of preferably at least 3, 2, 1, 0.5, 0.25 0.125 or 0.067% of the organic matter administered to the ruminant animal to decrease the ratio of acetate to propionate.

In one embodiment the ratio of acetate to propionate (C2/C3 ratio) following administration of an effective amount of at least one species of red marine macroalgae is not negatively affected. In another embodiment, the ratio of acetate to propionate (C2/C3 ratio) following administration of an effective amount of at least one species of red marine macroalgae is reduced.

In a preferred embodiment of the invention, the ratio of acetate to propionate (C2/C3 ratio) following administration of an effective amount at least one species of red marine macroalgae is not greater than 5. In another embodiment, the ratio of acetate to propionate (C2/C3 ratio) following administration of an effective amount at least one species of red marine macroalgae is not greater than 4. In another embodiment, the ratio of acetate to propionate (C2/C3 ratio) following administration of an effective amount at least one species of red marine macroalgae is not greater than 3. In another embodiment, the ratio of acetate to propionate (C2/C3 ratio) following administration of an effective amount at least one species of red marine macroalgae is not greater than 2.

In another embodiment, the molar concentration of propionate is not negatively affected.

For example, FIG. 17 shows that total VFA concentration is not negatively affected following administration of *Asparagopsis* to a ruminant animal (cattle), with total VFA concentrations equivalent to 73.5, 75.5 and 102.3 mmol·L−1 for control at day 1, after 15 d and 30 d, respectively.

FIG. 20 also shows that total VFA concentration is not negatively affected following administration of *Asparagopsis* to a ruminant animal (cattle).

Table 11 shows that propionate concentration is not negatively affected following administration of *Asparagopsis* to a ruminant animal (sheep), with significantly higher propionate concentrations following inclusion of *Asparagopsis* in feed at doses of 0.5, 1, 2, and 3% of organic matter intake per day.

The present inventors have demonstrated a dose dependent effect of dose on total VFA production and/or acetate to propionate ratio. For example, FIG. 13 shows a dose dependent effect of dose on total VFA production and/or acetate to propionate ratio. FIG. 17 shows that administration of at least one species of red marine macroalgae to a ruminant animal decreases the ratio of acetate to propionate. Table 11 shows that inclusion of *Asparagopsis* in animal feed decreases the ratio of acetate to propionate in a ruminant animal (sheep). FIG. 21 also shows that administration of at least one species of red marine macroalgae to a ruminant animal decreases the ratio of acetate to propionate.

Rumen fermentation of low quality fibrous feeds is the major source of methane production in ruminants.

Examples of ruminants are listed below. However, preferably the red marine macroalgae is used as an additive for foodstuffs for domesticated livestock such as cattle, goats, sheep and llamas. The present invention is particularly useful in cattle and sheep. Therefore, in one embodiment, said ruminant animal is selected from the members of the Ruminantia and Tylopoda suborders. In another embodiment, said ruminant animal is cattle or sheep. In a further embodiment, said ruminant animal is a cattle.

By "administer" and "administered", is meant the action of introducing at least one species of red marine macroalgae according to the invention into the animal's gastro-intestinal tract. More particularly, this administration is an administration by oral route. This administration can in particular be carried out by supplementing the feed intended for the animal with said at least one species of red marine macroalgae, the thus supplemented feed then being ingested by the animal. The administration can also be carried out using a stomach tube or any other means making it possible to directly introduce said at least one species of red marine macroalgae into the animal's gastro-intestinal tract.

The present inventors have demonstrated a reduction of total gas produced and/or methane produced in anaerobic fermentation in the presence of an effective amount of red marine macroalgae.

As discussed above, in preferred embodiments of the invention, an effective amount at least one species of red marine macroalgae is at least 16.67, 10, 5, 3, 2, 1, 0.5, 0.25 0.125 or 0.067% of the organic matter administered to the ruminant animal.

For example, the at least one species of red marine macroalgae is administered at a dose of preferably at least 3, 2, 1, 0.5, 0.25 0.125 or 0.067% of the organic matter available in the diet of the ruminant animal.

For example, if a ruminant animal consumes approximately 2.5-3% of its live weight of feed a day, a 400 kg ruminant animal may consume 10-12 kg of feed a day.

As discussed above, in preferred embodiments of the invention, an effective amount at least one species of red marine macroalgae is at least 16.67, 10, 5, 3, 2, 1, 0.5, 0.25 0.125 or 0.067% of the organic matter administered to the ruminant animal per day. Preferably, the at least one species of red marine macroalgae is administered at a dose of preferably at least 3, 2, 1, 0.5, 0.25 0.125 or 0.067% of the organic matter administered to the ruminant animal per day.

Therefore, if a 400 kg ruminant animal consumes about 10 kg of organic matter a day, an effective amount at least one species of red marine macroalgae is at least about 0.3, 0.2, 0.1, 0.05, 0.025, 0.0125, or 0.0067 kg of at least one species of red marine macroalgae per day. These doses are equivalent to 0.00075, 0.0005, 0.00025, 0.000125, 0.0000625, 0.0000325 or 0.00001675 kg per kg body weight per day.

The effective amount can be administered to said ruminant animal in one or more doses.

The effective amount can also be administered to said ruminant animal in one or more doses on a daily basis.

In another preferred embodiment a method as defined herein before is provided, wherein the dosage of at least one species of red marine macroalgae is within the range of 0.0005-1.8 g/kg body weight per day, more preferably within the range of 0.05-0.9 g/kg body weight per day, most preferably 0.1-0.45 g/kg body weight per day.

In another preferred embodiment a method as defined herein before is provided, wherein the dosage of at least one species of red marine macroalgae is within the range of 0.025-8 g/kg body weight per day, more preferably 0.05-4 g/kg body weight per day, most preferably 0.1-5 g/kg body weight per day.

The dosages defined herein as the amount per kg body weight per day concern the average amount of the at least one species of red marine macroalgae during a given period of treatment, e.g. during a week or a month of treatment. The at least one species of red marine macroalgae may thus be administered every day, every other day, every other two days, etc., without departing from the scope of the invention. Preferably though, the method comprises daily administration of the at least one species of red marine macroalgae in the prescribed dosages. Even more preferably the at least one species of red marine macroalgae is administered during feeding of the animal each time the animal is fed, in amounts yielding the above daily dosages.

The present method may comprise administration of the at least one species of red marine macroalgae in accordance with the above described dosage regimens for a period of at least 5, 10, 25, 50, 100, 250 or 350 days. An aspect of the invention resides in the fact that the present methods provides very persistent effectiveness in reducing enteric methanogenesis, e.g. the effect does not diminish over extended periods of treatment, e.g. as a result of increasing resistance of rumen or gut microorganisms, thereby rendering long-term treatment of the ruminant particularly feasible.

By "at least one species", is meant a single species but also mixtures of species comprising at least two species of red marine macroalgae.

When using a mixture of species the proportions can vary from less than 1% to 99%, more advantageously from 25% to 75% and even more advantageously approximately 50% for each species.

In one embodiment, the at least one species of red marine macroalgae is selected from a species of belonging the five genera of red seaweed in the family Bonnemaisoniaceae (*Asparagopsis, Bonnemaisonia, Delisea, Ptilonia, Leptophyllis*).

In one embodiment, the species of red marine macroalgae is an *Asparagopsis* species.

*Asparagopsis* has a heteromorphic life history with two free-living life history stages—a gametophyte (large foliose form) and a sporophyte (or tetrasporophyte—smaller, filamentous form). Historically, the tetrasporophyte was recognised as a separate genus (*Falkenbergia*). Therefore, the term "*Asparagopsis*" as used herein refers to the genus *Asparagopsis*, and other taxonomic classifications now known to belong to the genus *Asparagopsis*.

There are two recognised species of *Asparagopsis*, one tropical/sub-tropical (*Asparagopsis taxiformis*) and one temperate (*Asparagopsis armata*) and present throughout the world.

Therefore, in one embodiment, the species of the genus *Asparagopsis* are selected from the species:
  a. *Asparagopsis armata*
  b. *Asparagopsis taxiformis*

Without wishing to be bound by theory, the five genera of red seaweed in the family Bonnemaisoniaceae (*Asparagopsis, Bonnemaisonia, Delisea, Ptilonia, Leptophyllis*), produce and store bioactive halogenated natural products. These secondary metabolites function as natural defences against predation, fouling organisms and microorganisms, and competition among species.

*Dictyota* (also referred to herein) produces an array of secondary metabolites, in particular, isoprenoids (terpenes). *Asparagopsis* produces halogenated low molecular weight compounds, in particular brominated and chlorinated haloforms. Many of these compounds have strong antimicrobial properties and inhibit a wide range of microorganisms, including Gram-positive and Gram-negative bacteria, as well as, mycobacterium and fungus activities, and therefore may be involved in contributing to the effects described herein. Secondary metabolites from *Asparagopsis* also inhibit protozoans.

Accordingly, given the significant effects of *Asparagopsis* described herein, including reducing total gas production and $CH_4$ output, in one embodiment the at least one species of red marine macroalgae is preferably administered in a form that results in the effects described herein (e.g. to reduce $CH_4$ output) without affecting nutritionally important fermentation parameters.

In another embodiment, the at least one species of red marine macroalgae is preferably administered in a form in which the secondary metabolites remain therapeutically effective.

According to an embodiment of the invention, the at least one species of red marine macroalgae is freeze dried and ground to a powder. For example, the at least one species of red marine macroalgae is freeze dried and ground through a sieve (e.g. a 1 mm sieve).

According to another embodiment of the invention, the at least one species of red marine macroalgae is air dried and coarsely milled.

The at least one species of red marine macroalgae may be administered to the ruminant in one of many ways. The at least one species of red marine macroalgae can be administered in a solid form as a veterinary pharmaceutical, may be distributed in an excipient, and directly fed to the animal, may be physically mixed with feed material in a dry form or the at least one species of red marine macroalgae may be formed into a solution and thereafter sprayed onto feed material. The method of administration of the at least one species of red marine macroalgae to the animal is considered to be within the skill of the artisan.

When used in combination with a feed material, the feed material is preferably grain/hay/silage/grass-based. Included amongst such feed materials are improved and/or tropical grass or legume based forages either grazed directly or prepared as a conserved forage hay, any feed ingredients and food or feed industry by-products as well as bio-fuel industry by-products and corn meal and mixtures thereof, or feed lot and dairy rations, such as those high in grain content.

The time of administration is not crucial so long as the reductive effect on methane production is shown. As long as the feed is retained in the rumen, administration is possible at any time. However, since the at least one species of red marine macroalgae is preferably present in the rumen at about the time methane is produced, the at least one species of red marine macroalgae is preferably administered with or immediately before feed.

In a particular embodiment of the invention, said effective amount of at least one species of red marine macroalgae is administered to a ruminant animal by supplementing a feed intended for said animal with said effective amount of at least one species of red marine macroalgae. By "supplementing", within the meaning of the invention, is meant the action of incorporating the effective amount of at least one species of red marine macroalgae according to the invention directly into the feed intended for the animal. Thus, the animal, when feeding, ingests the at least one species of red marine macroalgae according to the invention which can then act to increase e.g. the digestibility of the fibres and/or cereals contained in the animal's feed.

Thus, another subject of the invention relates to a feed supplement for a ruminant animal comprising at least one species of red marine macroalgae.

In another aspect the present invention also provides a feed supplement for reducing total gas production and/or methane production in a ruminant animal, said supplement comprising an effective amount of at least one species of red marine macroalgae.

In one embodiment, the effective amount of at least one species of red marine macroalgae is administered to said ruminant animal by supplementing food intended for said animal with said effective amount of at least one species of red marine macroalgae.

In one embodiment, the species of red marine macroalgae is an *Asparagopsis* species. In another embodiment, the species of *Asparagopsis* is *A. taxiformis*.

As discussed above, in one embodiment the present invention maintains the levels of VFAs in the ruminant animal. Thus, this method allows the ruminant animal to maintain energy from feed based on e.g. fibers and cereals, and as a result, starting from the same calorific intake, to maintain the energy available for metabolism while mitigating total gas and $CH_4$ production.

This is advantageous for the livestock farmer who can thus optimize the cost of the feed per unit of metabolisable energy available. This also represents a substantial economic benefit.

Figure 16:
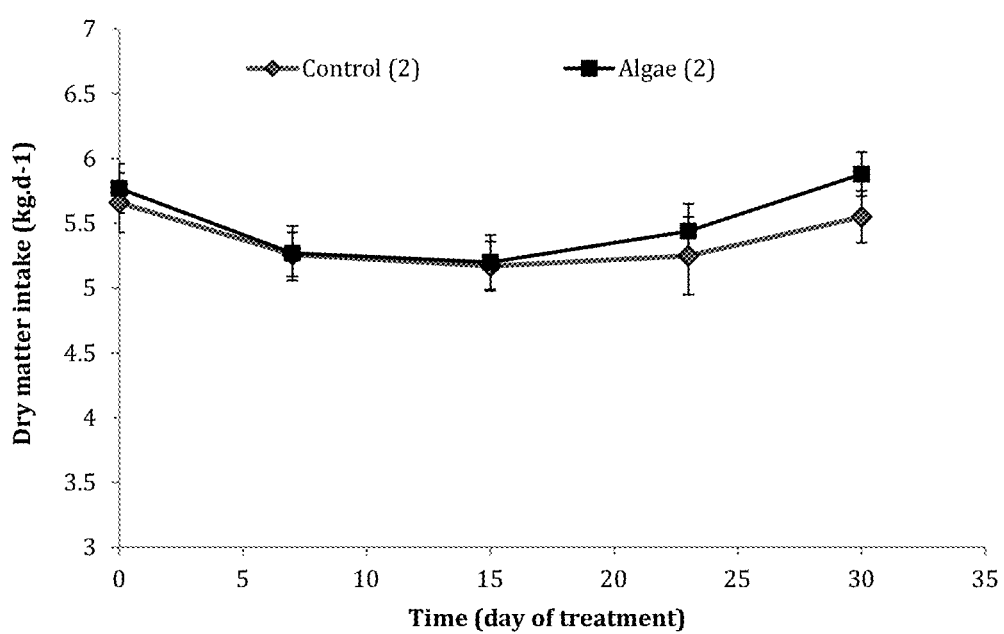
FIG. 16 shows mean feed intake for seven days for steers expressed as dry matter intake ($kg \cdot d^{-1}$). Number in parentheses indicates the number of steers per treatment. This figure demonstrates *Asparagopsis* does not reduce the dry matter intake in vivo. This figure also demonstrates *Asparagopsis* does not reduce the dry matter intake in vivo at doses of *Asparagopsis* that inhibit total gas and methane production in vivo. Error bars represent ±SE.

The present inventors have demonstrated that administration of an effective amount of *Asparagopsis* to a ruminant animal does not negatively impact voluntary feed intake. For example, FIG. 16 shows that administration of an effective amount of *Asparagopsis* to a ruminant animal at a dose equivalent to an average of 2.9% of dry matter intake per day does not negatively impact voluntary feed intake with differences in take between control and supplemented animals being no greater than 5.6% after 30 days of treatment. Table 11 demonstrates that administration of an effective amount of *Asparagopsis* to a ruminant animal at a dose equivalent to an average of 0.5%, 1%, 2% or 3% of organic matter intake per day does not negatively impact voluntary feed intake.

Therefore, the present invention provides a method wherein the level of organic matter and/or dry matter degraded is maintained.

As used herein, the term "animal feed supplement" refers to a concentrated additive premix comprising the active ingredients, which premix or supplement may be added to an animal's feed or ration to form a supplemented feed in accordance with the present invention. The terms "animal feed premix," "animal feed supplement," and "animal feed additive" are generally considered to have similar or identical meanings and are generally considered interchangeable. Typically, the animal feed supplement of the present invention is in the form of a powder or compacted or granulated solid. In practice, livestock may typically be fed the animal feed supplement by adding it directly to the ration, e.g. as a so-called top-dress, or it may be used in the preparation or manufacture of products such as compounded animal feeds or a lick blocks, which will be described in more detail hereafter. The invention is not particularly limited in this respect. A supplement according to the invention is typically fed to an animal in an amount ranging from 16-2500 g/animal/day.

In one embodiment, a supplement according to the invention is administered at an amount based on actual individual animal intake (e.g. g/kg DM intake).

The present animal feed supplement comprises at least one species of red marine macroalgae and is formulated so that when added to feed, the at least one species of red marine macroalgae is present at at least 0.067, 0.125, 0.25, 0.5, 1, 2, 3, 5, 10 or 16.67% of the organic matter of the feed.

For example, if a ruminant animal consumes approximately 5 kg of organic matter a day, the animal feed supplement comprises at least one species of red marine macroalgae and is formulated so that when added to feed, the at least one species of red marine macroalgae is present at a dose of 3.35, 6.25, 12.5, 25, 50, 100, 150, 250, 500 or 833.5 grams per day, respectively.

In preferred embodiments of the invention, the supplement comprises the at least one species of red marine macroalgae species present in an amount ranging from 10-100 wt %, preferably said amount is in excess of 10, 20, 30, 40, 50, 60, 70, 80, 90, 95, 97 or 99 wt %, on a dry weight basis.

It is within the skills of the trained professional to determine exactly the ideal amounts of the components to be included in the supplement and the amounts of the supplement to be used in the preparation of the ration or compounded animal feed, etc., taking into account the specific type of animal and the circumstances under which it is held. Preferred dosages of each of the components are given herein.

The animal feed supplements of the present invention may comprise any further ingredient without departing from the scope of the invention. It may typically comprise well-known excipients that are necessary to prepare the desired product form and it may comprise further additives aimed at improving the quality of the feed and/or at improving the performance of the animal consuming the supplement. Suitable examples of such excipients include carriers or fillers, such as lactose, sucrose, mannitol, starch crystalline cellulose, sodium hydrogen carbonate, sodium chloride and the like and binders, such as gum Arabic, gum tragacanth, sodium alginate, starch, PVP and cellulose derivatives, etc. Examples of feed additives known to those skilled in the art include vitamins, amino acids and trace elements, digestibility enhancers and gut flora stabilizers and the like.

Furthermore, the present inventors have found that good results are obtained when other macroalgae are used. For example, the present inventors have demonstrated *Dictyota, Oedogonium*, and *Cladophora patentiramea* reduce total gas production and $CH_4$ production from ruminal fermentation.

Therefore, in another embodiment, method further comprises administering to said ruminant animal an effective amount of at least one species of macroalgae selected from the group consisting of *Asparagopsis armata, Asparagopsis taxiformis, Dictyota* spp (e.g. *Dictyota bartayresii*), *Oedogonium* spp, *Ulva* spp, and *C. patentiramea*.

In general, marine algae were more effective than freshwater algae in reducing $CH_4$ production. Freshwater macroalgae have a similar biochemical composition to DCS, however, the $CH_4$ output relative to DCS was reduced to 4.4% for *Spirogyra* and 30.3% for *Oedogonium* after 72 h incubation. However, there was no correlation between the biochemical composition of freshwater macroalgae and a reduction in $CH_4$. Although $CH_4$ was reduced there were no apparent negative effects on fermentation variables. Rather, freshwater macroalgae had slightly higher total VFA concentration than DCS with similar organic matter degradability (OMd), demonstrating that fermentation processes had not been compromised.

Marine algae reduced $CH_4$ production significantly, with two species, the brown macroalga *Dictyota* and the red macroalga *Asparagopsis* having the most significant effects. *Dictyota* inhibited TGP by 53.2% and $CH_4$ production by over 92% compared to DCS, while *Asparagopsis* was the most effective treatment reducing TGP by 61.8%, and $CH_4$ production by 98.9% compared to DCS. *Dictyota* and *Asparagopsis* also produced the lowest total VFA concentration when administered at a dose of 16.67% of organic matter in vitro, and the highest molar concentration of propionate among all species, demonstrating that at this dose fermentation was significantly affected.

A decrease in the concentration of total VFAs is often associated with anti-nutritional factors that interfere with ruminal fermentation. *Asparagopsis*, at the concentrations tested in cattle, was over 17 times more effective in reducing the proportion of $CH_4$ within total gas produced than terrestrial plants high in tannins, or some feed cereals or legumes.

*Asparagopsis* has a similar (primary) biochemical composition to DCS with the exception of high levels of zinc and low PUFA. Both *Asparagopsis* and *Dictyota* had high concentrations of zinc, however, *Halymenia* also had a similar concentration but produced 47.9% more TGP and 89.5% more $CH_4$ than *Dictyota*. Notably, when zinc is added to a diet at a concentration above 250 mg·kg−1 DM, it can reduce in vitro substrate degradability and increase molar proportion of propionate, which are indicative parameters of reduced methane output. However, the concentration of zinc in *Dictyota* was 0.099 mg·kg−1 DM and in *Asparagopsis* 0.15 mg·kg−1 DM, and these concentrations are far below the threshold of 250 mg·kg−1 DM. Therefore, there is little supporting evidence that zinc reduces the production of $CH_4$ to the extent to which it occurs in *Dictyota* and *Asparagopsis*. Without wishing to be bound by theory, it is possible, however, that zinc acts synergistically with secondary metabolites produced by both species of algae to reduce $CH_4$ production. Some elements can enhance secondary metabolite concentrations of plants even at low threshold concentrations.

Without wishing to be bound by theory, the present inventors propose that *Asparagopsis* and *Dictyota* are rich in secondary metabolites with strong antimicrobial properties, and the lack of a strong relationship between gas and methane production, and any of the >70 primary biochemical parameters analysed suggests that the reduction in total gas production and $CH_4$ may be associated with secondary metabolites.

Accordingly, in one aspect the present invention relates to a method for reducing total gas production and/or methane production in a ruminant animal comprising the step of administering to said ruminant animal an effective amount of at least one species of red marine macroalgae and a second species of marine macroalgae.

In one embodiment the second species of marine macroalgae is selected from the group consisting of *Asparagopsis armata, Asparagopsis taxiformis, Dictyota* spp (e.g. *Dictyota bartayresii*), *Oedogonium* spp, *Ulva* spp, and *C. patentiramea*.

A further aspect of the invention concerns products such as a compounded animal feeds and a lick blocks, comprising a supplement as defined herein before.

The term 'compounded animal feed composition' as used herein, means a composition which is suitable for use as an animal feed and which is blended from various natural or non-natural base or raw materials and/or additives. Hence, in particular, the term 'compounded' is used herein to distinguish the present animal feed compositions from any naturally occurring raw material. These blends or compounded feeds are formulated according to the specific requirements of the target animal. The main ingredients used in commercially prepared compounded feeds typically include wheat bran, rice bran, corn meal, cereal grains, such as barley, wheat, rye and oat, soybean meal, alfalfa meal, cottonseed meal, wheat powder and the like. A commercial compound feed will typically comprise no less than 15% of crude protein and no less than 70% digestible total nutrients, although the invention is not particularly limited in this respect. Liquid, solid as well as semi-solid compounded animal feed compositions are encompassed within the scope of the present invention, solid and semi-solid forms being particularly preferred. These compositions are typically manufactured as meal type, pellets or crumbles. In practice, livestock may typically be fed a combination of compounded feed, such as that of the present invention, and silage or hay or the like. Typically a compounded animal feed is fed in an amount within the range of 0.3-10 kg/animal/day. It is within the skills of the trained professional to determine proper amounts of these components to be included in the compounded animal feed, taking into account the type of animal and the circumstances under which it is held.

The compounded animal feed compositions of the invention may comprise any further feed additive typically used in the art. As is known by those skilled in the art, the term 'feed additive' in this context refers to products used in animal nutrition for purposes of improving the quality of feed and the quality of food from animal origin, or to improve the animals' performance, e.g. providing enhanced digestibility of the feed materials. Non-limiting examples include technological additives such as preservatives, antioxidants, emulsifiers, stabilising agents, acidity regulators and silage additives; sensory additives, especially flavours and colorants; (further) nutritional additives, such as vitamins, amino acids and trace elements; and (further) zootechnical additives, such as digestibility enhancers and gut flora stabilizers.

As will be clear to those skilled in the art, the present compounded animal feed compositions can comprise any further ingredient or additive, without departing from the scope of the invention.

In a further aspect, the invention provides a lick stone or lick block comprising the supplement of the invention. As is known to those skilled in the art such lick stones or blocks are particularly convenient for feeding mineral supplements (as well as proteins and carbohydrates) to ruminants grazing either or both natural and cultivated pastures. Such lick blocks or lick stones in accordance with the present invention typically comprise, in addition to the red macroalgae of the invention, various types of binders, e.g. cements, gypsum, lime, calcium phosphate, carbonate, and/or gelatin; and optionally further additives such as vitamins, trace elements, mineral salts, sensory additives, etc.

A further aspect of the invention concerns a method of reducing gastro-intestinal methane production in a ruminant, said method comprising administering a composition comprising at least one species of red marine macroalgae.

The term 'reducing gastro-intestinal methanogenesis' and 'reducing gastro-intestinal methane production' as used herein refers to the reduction of methane gas production in the gastro-intestinal tract. As explained hereinbefore, fermentation in the rumen and the gut of a ruminant gives rise to production of methane gas by so-called methanogens. The present invention aims to reduce this process, such as to reduce the methane excretion directly from the gastro-intestinal tract. It is within the knowledge and skill of those trained in the art to assess methane excretion by an animal. As explained before, methane production in the rumen and gut is a process normally occurring in healthy animals and decreasing methanogenesis does not enhance or diminish the ruminant's general state of health or well-being.

Thus, the present methods of treatment are non-therapeutic methods of treatment, i.e. the methods do not improve the health of an animal suffering from a particular condition, do not prevent a particular disease or condition, nor do they to any extent affect the health of the ruminant in any other way, i.e. as compared to a ruminant not receiving the present methods of treatment. The advantages of the present methods are limited to environmental and/or economic aspects as explained before.

As will be clear from the above, the present method comprises oral administration of the at least one species of red marine macroalgae. Preferably the treatment comprises oral administration of the compounded animal feed compositions and/or the animal feed supplement products as defined hereinbefore, even though other liquid, solid or semi-solid orally ingestible compositions may be used without departing from the scope of the invention, as will be understood by those skilled in the art.

In accordance with the foregoing, still a further aspect of the invention concerns the use of a composition comprising the at least one species of red marine macroalgae for the non-therapeutic reduction of gastro-intestinal methane production in a ruminant.

In another aspect, the present invention also provides a feed for a ruminant animal, wherein said feed is supplemented with a feed supplement described herein.

In another aspect the present invention provides a method for reducing methane production by a ruminant animal, said method comprising the step of administering to said animal a feed supplement described herein or a feed described herein.

The invention will now be further described by way of Examples, which are meant to serve to assist one of ordinary skill in the art in carrying out the invention and are not intended in any way to limit the scope of the invention.

Example 1: Materials and Methods

Collection and Preparation of Algae Samples

Twenty species of marine and freshwater macroalgae were selected for this study based on their occurrence and abundance in aquaculture systems and intertidal areas around Townsville, Queensland, Australia (Table 3). Seven species of macroalgae were harvested from large scale cultures at James Cook University, Townsville. The remaining species were collected at two intertidal reef flats: Nelly Bay, Magnetic Island (19° 16' S; 146° 85' E) under GBRMPA permit number GO2/20234.1; Rowes Bay (19° 23' S, 146° 79' E, Townsville) under DPIF permit number 103256; and from marine and freshwater aquaculture facilities in Townsville and surrounds.

All macroalgae were rinsed in freshwater to remove sand, debris and epiphytes. Biomass was centrifuged (MW512; Fisher & Paykel) at 1000 rpm for 5 min to remove excess water and weighed. A sub-sample of each species was preserved in 4% formalin for taxonomic identification, while the remaining biomass was freeze-dried at −55° C. and 120 µbar (VirTis K benchtop freeze-drier) for at least 48 h. Freeze-dried samples were ground in an analytical mill through 1 mm sieve, and stored in airtight containers at −20° C. until incubation.

Biochemical Parameters of Substrates

The proximate and elemental composition (from here on referred to as biochemical parameters) of macroalgae, decorticated cottonseed meal (DCS) and Flinders grass (*Iseilema* sp.) hay were evaluated in duplicate (Table 3 and Table 4). Moisture content was determined using a digital moisture analyzer (A&D, MS-70, Tokyo, Japan), where 2 g samples were heated at 105° C. to constant weight. The dry matter (DM) content was determined by deducting the moisture content from the total weight of the samples. Organic matter content (OM) was determined by combustion of the 2 g samples in a muffle furnace for 6 h at 550° C. Carbon, hydrogen, oxygen, nitrogen, phosphorous, and sulfur (CHONS) were quantified by elemental analysis (OEA laboratory Ltd., UK). Crude protein (CP) fraction was estimated using total nitrogen content (wt %) of the biomass with nitrogen factors of 5.13, 5.38, and 4.59 for green, brown and red macroalgae, respectively, and 6.25 for DCS and Flinders grass hay. Total lipid content was extracted and quantified using the Folch method. Fatty acids were extracted by a one-step extraction/transesterification method and quantified as fatty acid methyl esters (FAME) by gas GC/MS/FID (Agilent 7890 GC with FID—Agilent 5975C EI/TurboMS), as described in (Table 5). Carbohydrate content was determined by difference according to equation (1):

Carbohydrates (wt %)=100−(Ash+Moisture+Total lipids+Crude proteins)　　(1)

Where ash, moisture, total lipids and crude proteins are expressed as a percentage of DM.

The gross energy content (GE) of each sample was calculated according to Channiwala and Parikh, based on elemental composition:

$GE\ (Mj\ kg^{-1}\ DM)=0.3491*C+1.1783*H+0.1005*S-0.1034*O-0.0151*N-0.0211*ash$

Since macroalgae accumulate essential mineral elements and heavy metals which can inhibit anaerobic digestion, the concentrations of 21 elements were also quantified on 100 mg samples using ICP-MS analysis.

Example 2: In Vitro Experimental Design

Rumen fluid was collected from three rumen fistulated Bos indicus steers (632±32.62 kg live weight) which were maintained at the School of Biomedical and Veterinary Sciences, JCU, according to experimental guidelines approved by CSIRO Animal Ethics Committee (A5/2011) and in accordance with the Australian Code of Practice for the Care and Use of Animals for Scientific Purposes (NHMRC, 2004). The steers were fed Flinders grass hay (*Iseilema* spp.) ad libitum throughout the study to maintain a consistent microbial activity in the inoculum. Approximately 1 L of rumen liquid and solids were collected from each animal before the morning feed and placed into pre-heated thermal flasks. Pooled rumen fluid was blended at high speed for 30 seconds, using a hand held blender, to ensure complete mixing of solid and liquid phase and detachment of particulate associated bacteria into suspension, and then strained through a 1 mm mesh. Strained rumen fluid was continuously purged with high purity $N_2$ and maintained at 39° C. Rumen medium was prepared using rumen fluid and pre-heated buffer solution [Goering H, Van Soest P. J. (1970) Forage fiber analyses (apparatus, reagents, procedures, and some applications): US Agricultural Research Service Washington, DC] (no trypticase added) in a 1:4 (vol:vol) ratio.

A series of batch culture incubations were conducted to assess the effect of species of macroalgae on ruminal fermentation/total gas production and $CH_4$ concentration in head-space using an Ankom RF Gas Production System (Ankom Technology, New York, USA). Samples of 0.2 g OM of macroalgae were weighed into pre-warmed 250 mL Schott bottles with 1 g OM of Flinders grass (ground through 1 mm sieve), resulting in 0.2/1.2 g OM, and 125 mL of rumen medium. Therefore, *Asparagopsis* was administered at a dose of 16.67% OM. To optimize anaerobic conditions, bottles were purged with $N_2$, sealed and incubated at 39° C. in three temperature controlled incubator/shakers (Ratek, OM11 Orbital Mixer/Incubator, Australia), with the oscillation set at 85 rpm. A blank and a positive control, a bottle containing 1 g OM of Flinders grass and 0.2 g OM of DCS, were included in each incubator. The incubations were repeated on three different occasions with four replicates. For each incubation run, bottles were randomly allocated and placed inside incubators. Each bottle was fitted with an Ankom RF module and monitored for 72 h with reading intervals of 20 minutes to generate TGP curves. Each module contained a pressure valve set to vent at 5 psi. Head-space gas sample were collected from each module directly into pre-evacuated 10 mL exetainers (Labco Ltd, UK) every 24 h. TGP of the head-space sample was converted from pressure readings to mL/g OM.

Post-Fermentation Parameters

After 72 h incubation, pH (PHM220 Lab pH Meter, Radiometer Analytical, Lyon, France) was recorded and residual fluid samples were stored at −20° C. until analyses. VFAs were quantified at the University of Queensland (Ruminant Nutrition Lab, Galton College, Queensland, Australia) following standard procedures [Cottyn BG, Boucque CV (1968) Rapid method for the gas-chromatographic determination of volatile fatty acids in rumen fluid. Journal of Agricultural and Food Chemistry 16: 105-107; Ottenstein D, Bartley D (1971) Separation of free acids C2-C5 in dilute aqueous solution column technology. Journal of Chromatographic Science 9: 673-681; Playne M J (1985) Determination of ethanol, volatile fatty acids, lactic and succinic acids in fermentation liquids by gas chromatography. Journal of the Science of Food and Agriculture 36: 638-644]. Total VFA concentration was calculated by subtracting the total VFA concentration in the initial inoculum (buffered rumen fluid) from the total VFA concentration in the residual fluid. Residual fluids were also analysed for total ammonia concentration using semi-automated colorimetry (Tropwater Analytical Services, JCU, Townsville). Solid residues were analysed for apparent degradability of organic matter (OMd), calculated as the proportional difference between organic matter incubated and recovered after 72 h. $CH_4$ concentration in the collected gas samples were measured by gas chromatography (GC-2010, Shimadzu), equipped with a Carbosphere 80/100 column and a Flame Ionization Detector (FID). The temperature of the column, injector and FID were set at 129° C., 390° C., and 190° C., respectively. Helium and $H_2$ were used as carrier and burning gases, respectively. Four external standards of known composition: 1) $CH_4$ 0% and $CO_2$ 0% in $N_2$; 2) $CH_4$ 3% and $CO_2$ 7% in $N_2$; 3) $CH_4$ 8.89%, $CO_2$ 15.4%, and $H_2$ 16.8% in N2; and 4) $CH_4$ 19.1%, $CO_2$ 27.1%, and $H_2$ 38.8% in $N_2$ (BOC Ltd, Australia) were injected daily for construction of standard curves and used to quantify $CH_4$ concentration. Standards were collected following the same procedure used for collection of fermentation gas samples. Additionally, standard 2 ($CH_4$ 3% and $CO_2$ 7% in $N_2$) was injected every 2 h between successive gas samples to verify GC gas composition readings. Head-space samples (1 mL) were injected automatically into the GC to determine $CH_4$ concentrations. Peak areas were determined by automatic integration. $CH_4$ measured were related to TGP production to estimate relative concentrations.

Data Analysis

Corrected TGP data were fitted to a modified non-linear sigmoidal model of Gompertz [Bidlack J, Buxton D (1992) Content and deposition rates of cellulose, hemicellulose, and lignin during regrowth of forage grasses and legumes. Canadian Journal of Plant Science 72: 809-818]:

$$y=Ae^{-Be^{-Ct}}　　(3)$$

where y is the cumulative total gas production (mL), A the maximal gas production ($mL \cdot g^{-1}$), B the lag period before exponential gas production starts (h), C is the specific gas production rate ($mL \cdot h^{-1}$) at time t (h). The gas production parameters A, B, and C, were calculated using the non-linear procedure of SAS (JMP 10, SAS Institute, Cary, NC, USA). One-way analyses of variance (ANOVA) were used to compare the differences in total gas production (TGP) and $CH_4$ production at 72 h between species. Post-hoc comparisons were made using Tukey's HSD multiple comparisons.

Following the ANOVAs, multivariate analyses were used to investigate the relationships between the biochemical and post-fermentation parameters. Two complementary multivariate techniques were used. To examine correlations between variables nonmetric multidimensional scaling was used (MDS; Primer v6 [Clarke K R, Gorley R N (2006) PRIMER v6: User Manual/Tutorial: PRIMER-E Ltd, Plymouth, UK. 190 p.]) and to examine possible threshold values for effects Classification and regression tree was used (CART; TreesPlus software).

For MDS, samples that are close together on plots have similar composition. Thus, a MDS bi-plot was produced to investigate correlations between the biochemical and post-fermentation parameters of species at 72 h incubation. Data was reassembled in a Bray-Curtis similarity matrix using mean values for each species.

Information on the strength and nature of the correlation of biochemical or post-fermentation parameters with the distribution of species within the MDS space was represented as vectors in an ordination bi-plot. The parameters most highly correlated with the MDS space, based on Pearson's correlation coefficients (PCC) higher than 0.7, were plotted (Tables 1 and 2).

Because there were no overarching relationships between the major primary compositional variables and TGP, $CH_4$, and other post-fermentation variables (see results, Example 3), a multivariate CART was conducted to test the direct effects of biochemical compositional values for each species on TGP, $CH_4$ production, acetate and propionate concentrations. In this instance CART was used to highlight independent variables that may have subtle or interactive effects on the post-fermentation parameters. Data was fitted using 10-fold cross validation based on minimizing the error sum of squares. The sum of squares is equivalent to the least squares of linear models. Final tree models were chosen based on the ±1SE rule, which provided 2 key independent variables for the split.

Example 3: Total Gas and Methane Production

Total gas production (TGP) was lower for all species of macroalgae compared to DCS (FIG. 1, ANOVA: 72 h, $F_{20,63}=14.36$, $p<0.001$). The freshwater green macroalga *Spirogyra* (FIG. 1a) and the marine green macroalga *Derbesia* (FIG. 1b) had the highest TGP of all species, producing a total of 119.3 mL·g$^{-1}$ OM and 119.7 mL·g$^{-1}$ OM, respectively, and were not significantly different from DCS (Table 2, Tukey's HSD 72 h, $p>0.05$). *Oedogonium* was the only freshwater green macroalga that was significantly different from DCS (FIG. 1a, Tukey's HSD 72 h, $p<0.05$), decreasing TGP by up to 20.3% after 72 h incubation. *Cladophora patentiramea* had the lowest TGP of the marine green macroalgae, producing a total of 79.7 mL·g$^{-1}$ OM (FIG. 1b). The effect was most prominent at 24 h when TGP was reduced by 68.9% compared to DCS, and TGP was significantly reduced at 72 h, (FIG. 1b, Tukey's HSD 72 h, $p<0.0001$).

*Dictyota* was the most effective species of brown macroalgae, reducing TGP to 59.4 mL·g-1 OM after 72 h (FIG. 1c), resulting in a significantly lower TGP (53.2%) than for DCS (FIG. 1c, Tukey's HSD 72 h, $p<0.0001$). This effect was even greater at 24 h (TGP=76.7% lower than DCS). Although other brown macroalgae were not as effective as *Dictyota*, overall they reduced TGP by >10%, with *Padina*, *Cystoseira*, and *Colpomenia* significantly reducing TGP compared to DCS (Table 2, Tukey's HSD 72 h, $p<0.02$). The most effective of all macroalgae was the red alga *Asparagopsis* (FIG. 1d) with the lowest TGP, 48.4 mL·g-1 OM.

Although *Asparagopsis* had a similar trend to *Dictyota* and *C. patentiramea* for the first 48 h, its efficacy was maintained throughout the incubation period, producing 61.8% less TGP than DCS after 72 h.

Figure 12:
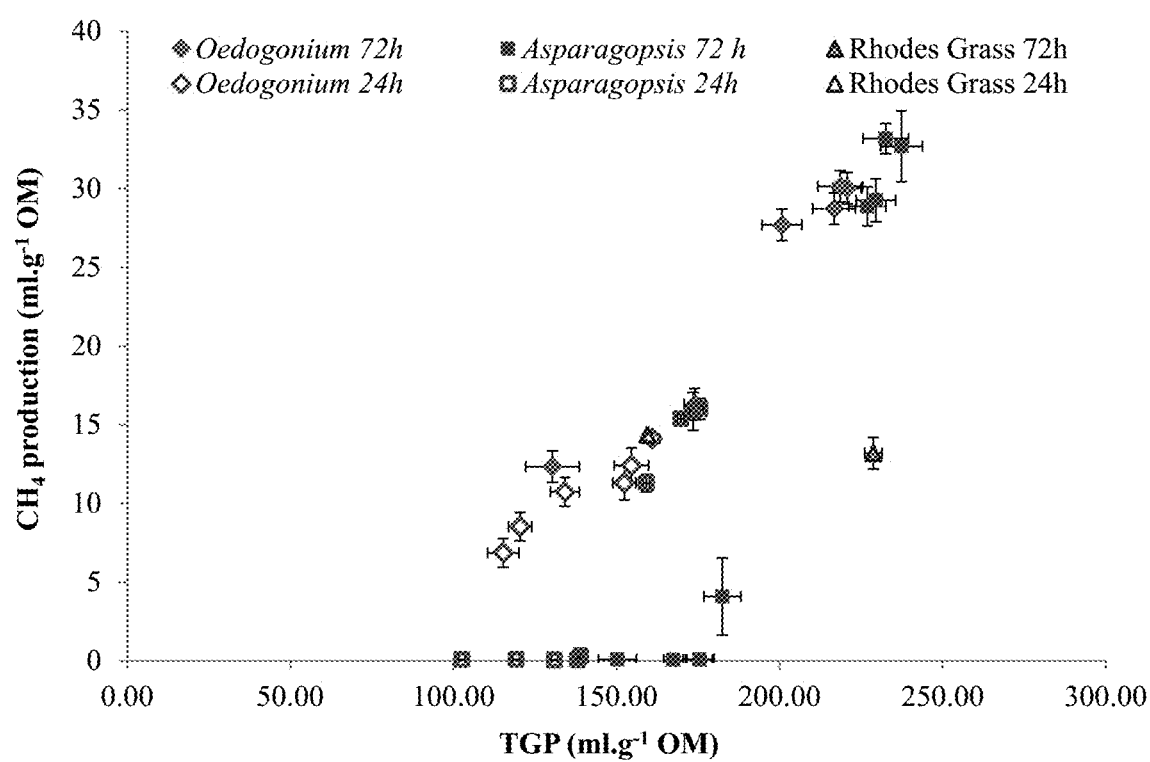
FIG. 12 shows the relationship between total gas (ml·g$^{-1}$ OM) and methane production (ml·g$^{-1}$ OM) of *Asparagopsis*, *Oedogonium*, and Rhodes grass (control) at 24 and 72 h of anaerobic incubation in vitro. Error bars represent ±SE.

$CH_4$ production generally followed the same pattern as TGP and notably $CH_4$ production was directly and significantly correlated with TGP values (FIG. 12). DCS had the highest $CH_4$ output, producing 18.1 mL·g$^{-1}$ OM at 72 h. All macroalgal treatments were, on average, lower than DCS after 72 h (FIG. 2, ANOVA: 72 h, $F_{20,55}=10.24$, $p<0.0001$). In a similar manner to TGP, the freshwater green macroalga *Spirogyra* (FIG. 2a) and marine green macroalga *Derbesia* (FIG. 2b) had the highest $CH_4$ production of all species, and grouped with DCS (Table 2, Tukey's HSD 72 h, $p>0.05$). *Asparagopsis, Dictyota* and *C. patentiramea* also had the most pronounced effect on reducing in vitro $CH_4$ production. *C. patentiramea* had a $CH_4$ output of 6.1 mL·g-1 OM (Table 1) and produced 66.3% less CH4 than DCS (FIG. 2b, Tukey's HSD 72 h, $p<0.0001$). *Dictyota* produced 1.4 mL·g$^{-1}$ OM and was the most effective of the brown macroalgae, reducing $CH_4$ output by 92% (FIG. 2c, Table 2, Tukey's HSD 72 h, $p<0.001$), and the concentration of $CH_4$ within TGP, 23.4 mL·L-1, by 83.5% compared to DCS (Table 2).

*Asparagopsis* had the lowest $CH_4$ output among all species of macroalgae producing a maximum of 0.2 mL·g-1 OM throughout the incubation period (Table 2, Tukey's HSD 72 h, $p<0.001$). This is a reduction of 98.9% on $CH_4$ output compared to DCS (FIG. 2d), independently of time. Notably, *Asparagopsis* also had the lowest concentration of $CH_4$ within TGP producing only 4.3 mL·L$^{-1}$ of $CH^4$ per litre of TGP after 72 h, making it distinct from all other species (Table 2).

Other Post-Fermentation Parameters

There were significant effects of macroalgae on VFA production among species (ANOVA: 72 h, $F20, 60=2.01$, $p=0.02$). *Spirogyra* produced 36.59 mmol·L$^{-1}$ of VFA, the highest total VFA production among all species and 31.6% more than DCS. *Oedogonium, C. vagabunda, Caulerpa, Chaetomorpha, Ulva* sp., *Sargassum* and *Hypnea* also produced 2.3% to 20.4% more VFA than the control DCS (Table 2). *Dictyota* and *Asparagopsis* had the lowest total VFA production. The decrease in total VFA was influenced by the inhibition of acetate (C2) production leading to a decrease in the C2:C3 ratio. *Asparagopsis* had the lowest C2:C3 ratio, 0.92, followed by *Dictyota* with almost double this value, 1.73 (Table 2).

Ammonia ($NH_3$) production varied significantly among species (ANOVA: 72 h, $F20,63=3.37$, $p<0.0001$). DCS had the highest concentration of $NH_3$ at 9.5 mg N·L$^{-1}$, while *Asparagopsis* and *Hypnea* had the lowest $NH_3$ concentration of 6.7 mg N·L$^{-1}$. Although apparent organic matter degradability (OMd) varied from a minimum of 58% for *Dictyota* to maximum of 64% for DCS, this difference was not significant ($p>0.05$). Similarly pH varied from a minimum of 6.85 for *Spirogyra* to a maximum of 7.13 for *Dictyota* (Table 2), this difference was not significant and all values were within the range required to maximize fiber digestion for ruminant.

Biochemical and Post-Fermentation Parameters

Figure 3:
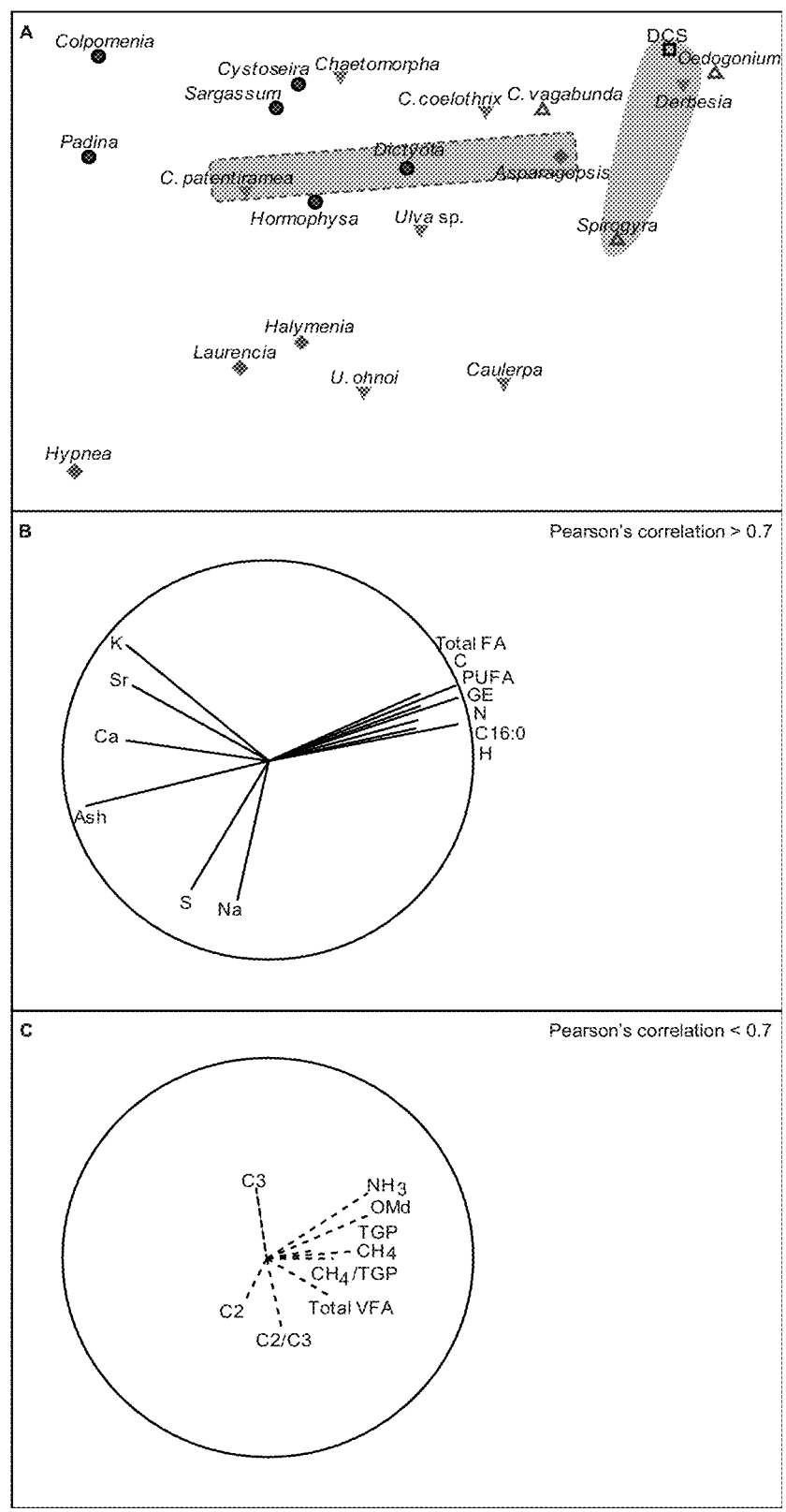
FIG. 3 shows Multi-dimensional scaling analysis (MDS) to illustrate similarities between macroalgae species based on biochemical and post-fermentation parameters. (A) MDS plot (Stress=0.11) of the distribution of species within ordination space. Species within grey cluster had the highest TGP and $CH_4$ production, while species within dotted line grey cluster had the lowest TGP and $CH_4$ production. (B) shows the MDS vectors with Pearson's correlation coefficients (r) higher than 0.7 superimposed. (C) shows post-fermentation parameters vectors superimposed (note all correlation coefficients lower than 0.7, see Table 2). White and blue triangles: Freshwater green algae, green triangles: Marine green algae, brown circles: Brown algae, red diamonds: Red algae; and square: DCS. Species full names are given in Table 1. This figure demonstrates species (e.g. *Dictyota*, *Asparagopsis* spp.) that reduce methane and/or TGP production from anaerobic fermentation are spread across the MDS bi-plot, and these variables are not strongly correlated to any of the main biochemical variables that affected the spread of species within the MDS.

The MDS bi-plot between biochemical parameters and post-fermentation parameters at 72 h showed that *Oedogonium* and *Derbesia* grouped closely with DCS, and this grouping was most similar to *C. vagabunda, C. coelothrix*,

*Asparagopsis* and *Spirogyra* (FIG. 3*a*). The biochemical parameters with the highest correlation with the MDS space were ash, C, GE, and H and these were the most important parameters in differentiating algae (Table 1). The species located on the top right corner of the MDS bi-plot (FIG. 3*a*) were positively correlated to the elements C, N, H, and GE, total fatty acid, polyunsaturated fatty acid (PUFA) and C:16 (FIG. 3*b*). Most brown macroalgae grouped together on the top left corner of the MDS plot (FIG. 3*a*) with *Padina, Colpomenia*, and *Sargassum* having the highest strontium concentrations of >1.5 g·kg$^{-1}$ DM (Table 1). Species with higher TGP and $CH_4$ production clustered on the left side of the MDS bi-plot (continuous line cluster, FIG. 3*a*). However, species with low TGP and $CH_4$ production were spread across the bi-plot (dotted line cluster, FIG. 3*a*), indicating that these variables were not strongly correlated to any of the main biochemical variables that affected the spread of species within the MDS (r <0.19, and 0.42, respectively; FIG. 3*a*). Similarly, the other post-fermentation parameters were not strongly correlated to any biochemical parameter in the MDS bi-plot (FIG. 4*b*, Table 2).

Figure 4:
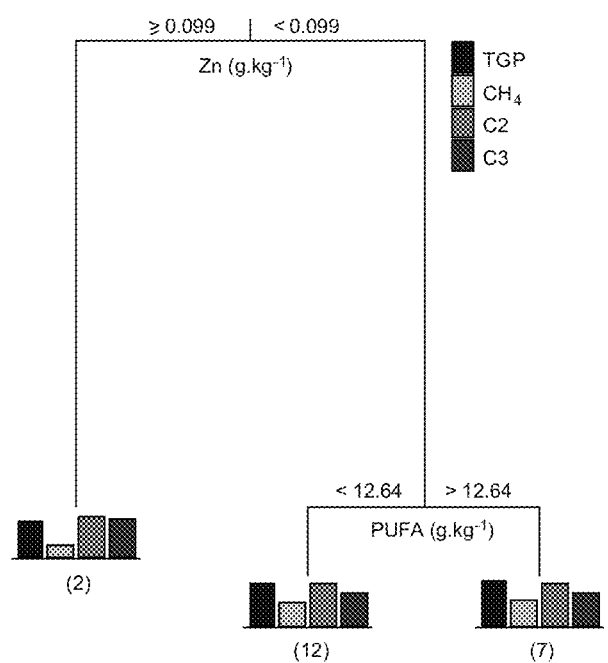
FIG. 4 shows multivariate classification and regression tree model. This CART is based on biochemical variables explaining 79.1% of the variability in total gas production (TGP), $CH_4$ production, and acetate (C2) and propionate (C3) molar proportions. Data was fourth-root transformed. Numbers in brackets indicate the number of species grouped in each terminal branch. This figure demonstrates that zinc was the independent variable with the highest importance on the multivariate CART model, suggesting that zinc may interact with other biochemical variables specific to *Dictyota* and *Asparagopsis* spp.
Figure 5:
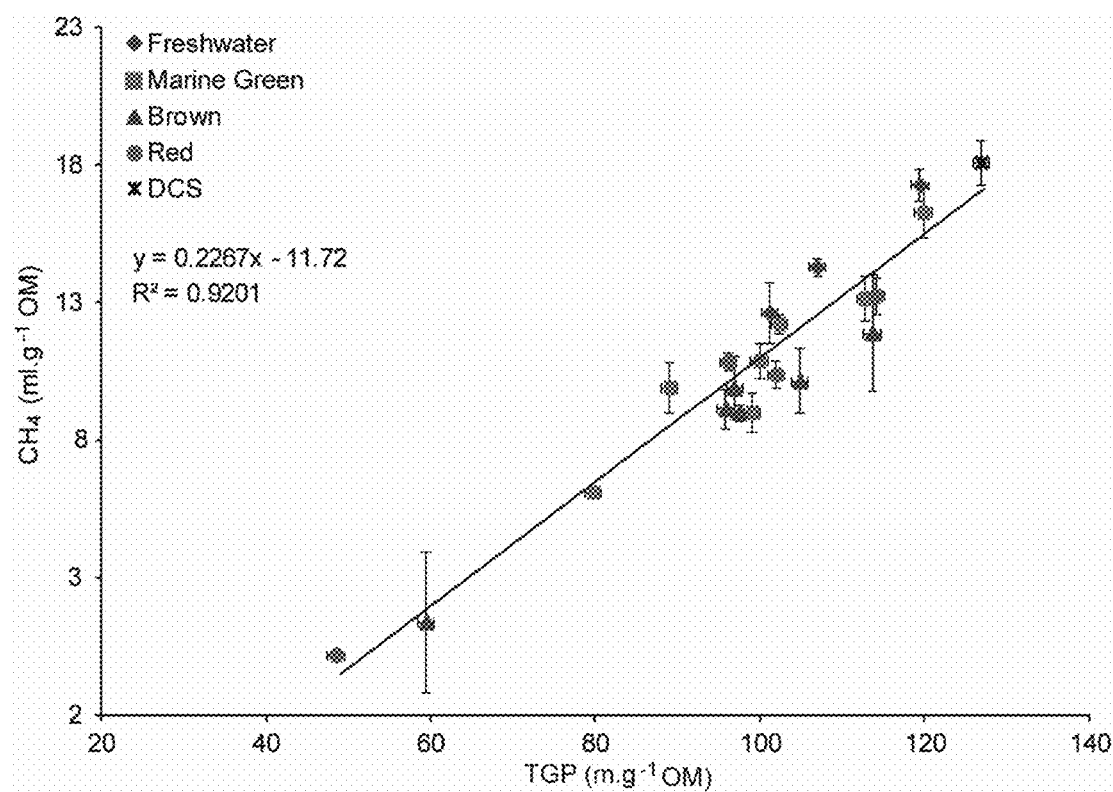
FIG. 5 shows the linear relationship between total gas (ml·g$^{-1}$ OM) and $CH_4$ production (ml·g$^{-1}$ OM) in vitro for macroalgae species compared with decorticated cottonseed meal (DCS). Individual data points represent mean values (mg·g$^{-1}$ OM, ±SE) for each species.
Figure 6:
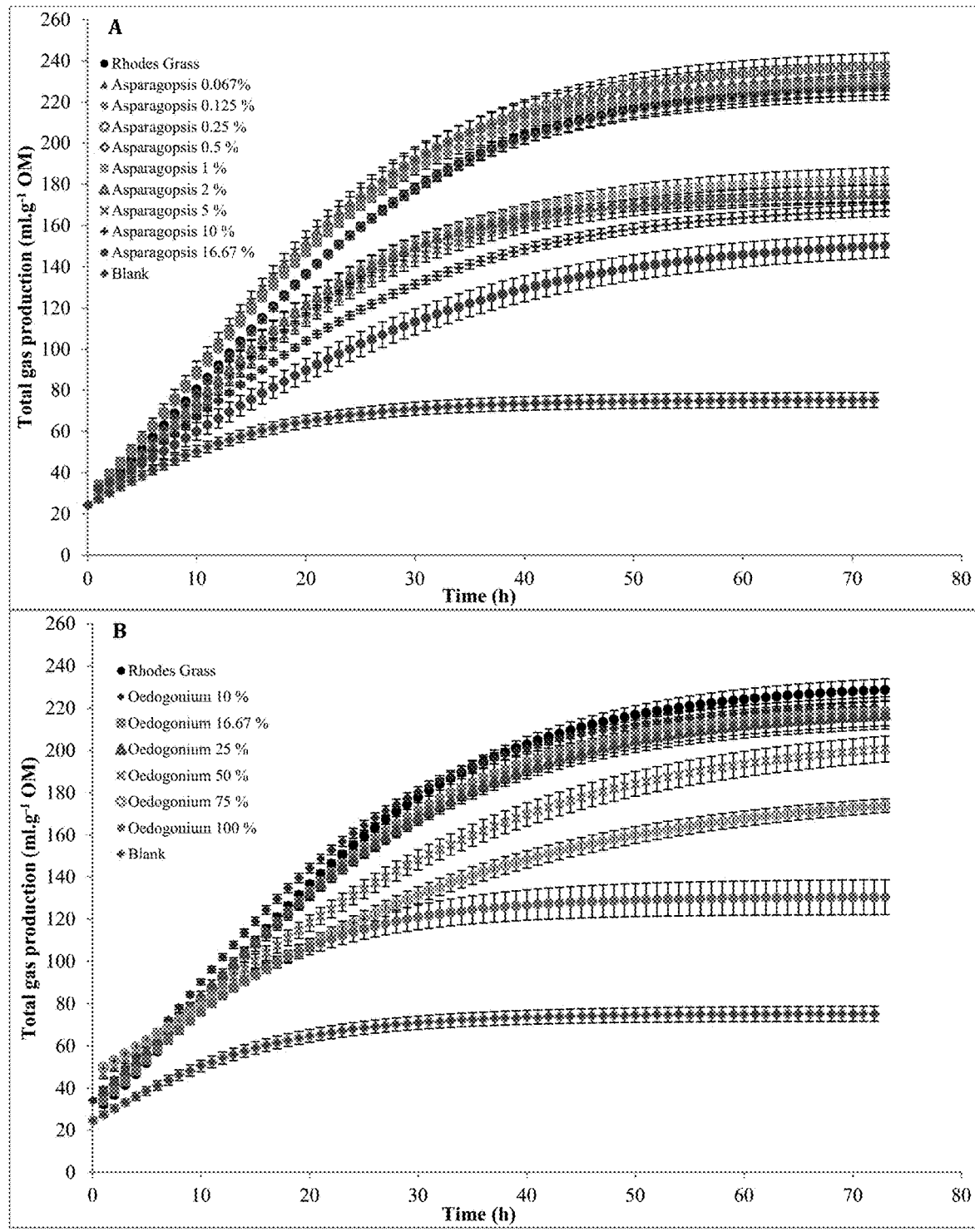
FIG. 6 shows total gas production of *Asparagopsis* (A) and *Oedogonium* (B) in vitro over the 72 h incubation period. Error bars represent ±SE (n=4). This figure demonstrates *Asparagopsis* and *Oedogonium* spp. reduce total gas production from anaerobic fermentation in vitro. This figure also demonstrates *Asparagopsis* and *Oedogonium* spp. reduce total gas production from anaerobic fermentation in a dose dependent manner.
Figure 7:
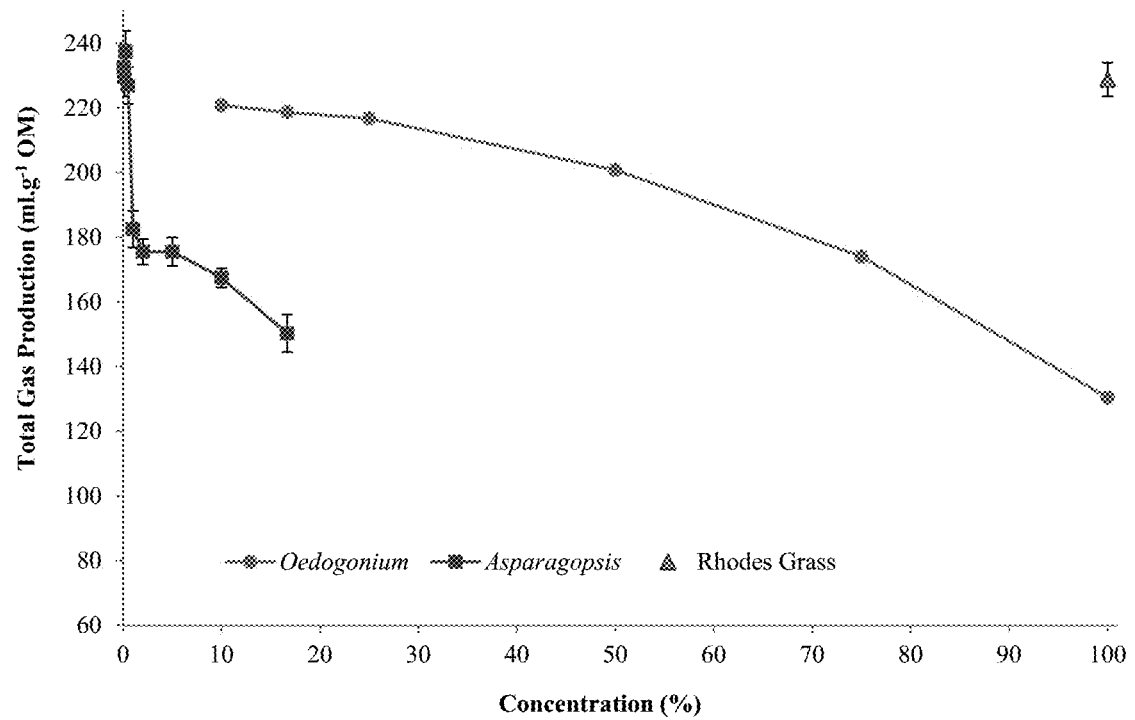
FIG. 7 shows total gas production in the presence of *Asparagopsis*, *Oedogonium* and Rhodes grass (control) at 72 h. This figure demonstrates *Asparagopsis* and *Oedogonium* spp. reduce total gas production from anaerobic fermentation in vitro. This figure also demonstrates *Asparagopsis* and *Oedogonium* spp. reduce total gas production from anaerobic fermentation in a dose dependent manner. Error bars represent ±SE.
Figure 8:
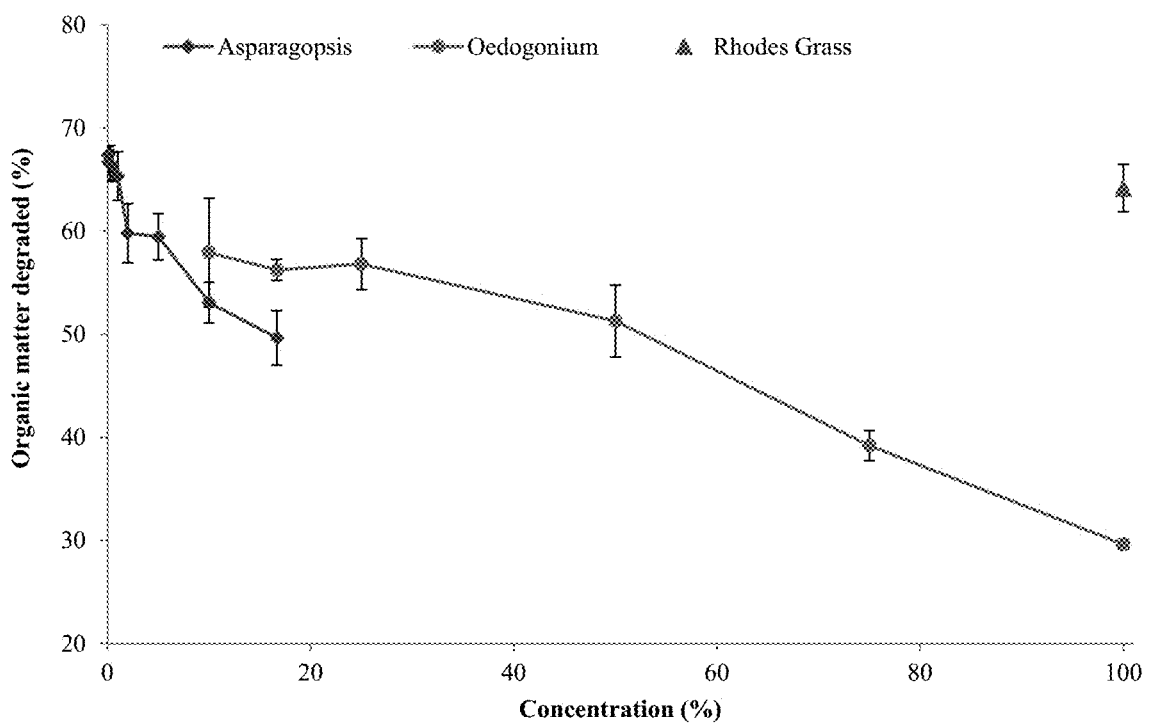
FIG. 8 shows Organic Matter degradation (%) in the presence of *Asparagopsis*, *Oedogonium* and Rhodes grass (control) after 72 h anaerobic incubation in vitro. This figure demonstrates *Asparagopsis* and *Oedogonium* spp. reduce the amount of organic matter degraded from anaerobic fermentation in a dose dependent manner. This figure also demonstrates *Asparagopsis* spp. does not reduce the amount of organic matter degraded at doses that inhibit total gas and methane production. Error bars represent ±SE.
Figure 9:
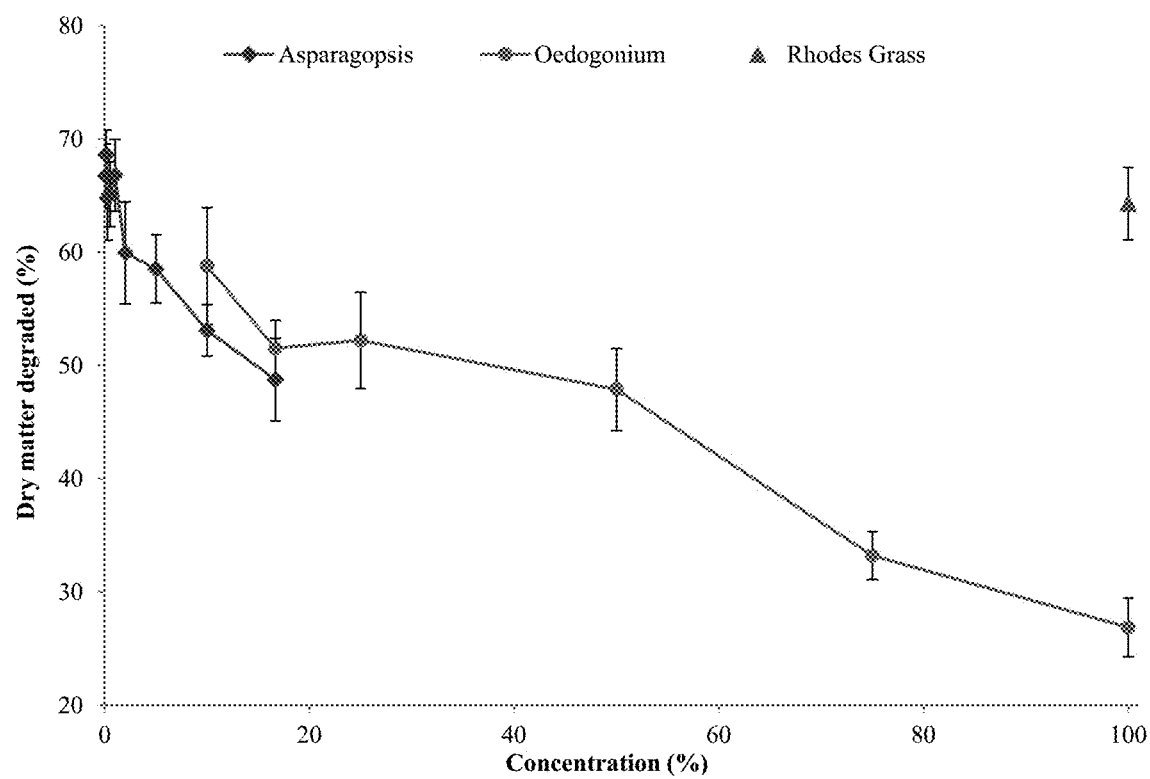
FIG. 9 shows Dry Matter degradation (%) in the presence of *Asparagopsis*, *Oedogonium* and Rhodes grass (control) after 72 h anaerobic incubation in vitro. This figure demonstrates *Asparagopsis* and *Oedogonium* spp. reduce the amount of dry matter degraded from anaerobic fermentation in a dose dependent manner. This figure also demonstrates *Asparagopsis* does not reduce the amount of dry matter degraded at doses of *Asparagopsis* that inhibit total gas and methane production. Error bars represent ±SE.
Figure 10:
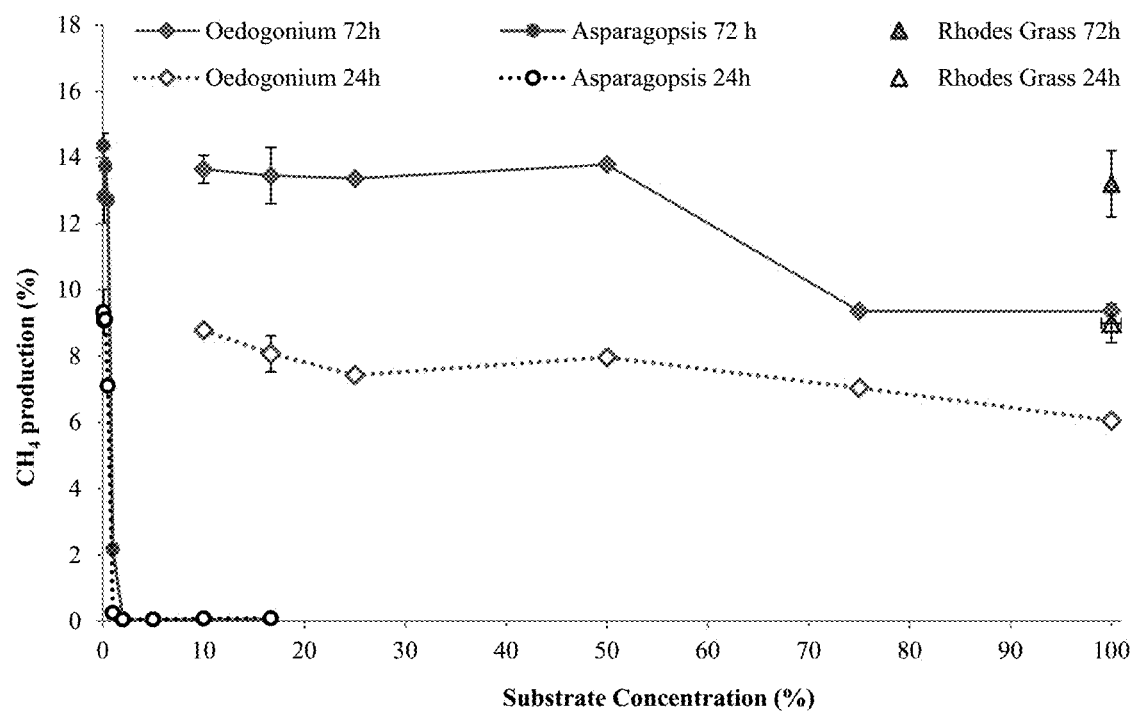
FIG. 10 shows mean $CH_4$ production as % of total gas produced at 24 and 72 h of anaerobic incubation in vitro. This figure demonstrates *Asparagopsis* reduces $CH_4$ production as a % of TGP from anaerobic fermentation. This figure also demonstrates *Asparagopsis* reduces $CH_4$ production as a % of TGP from anaerobic fermentation in a dose dependent manner. Error bars represent ±SE.
Figure 11:
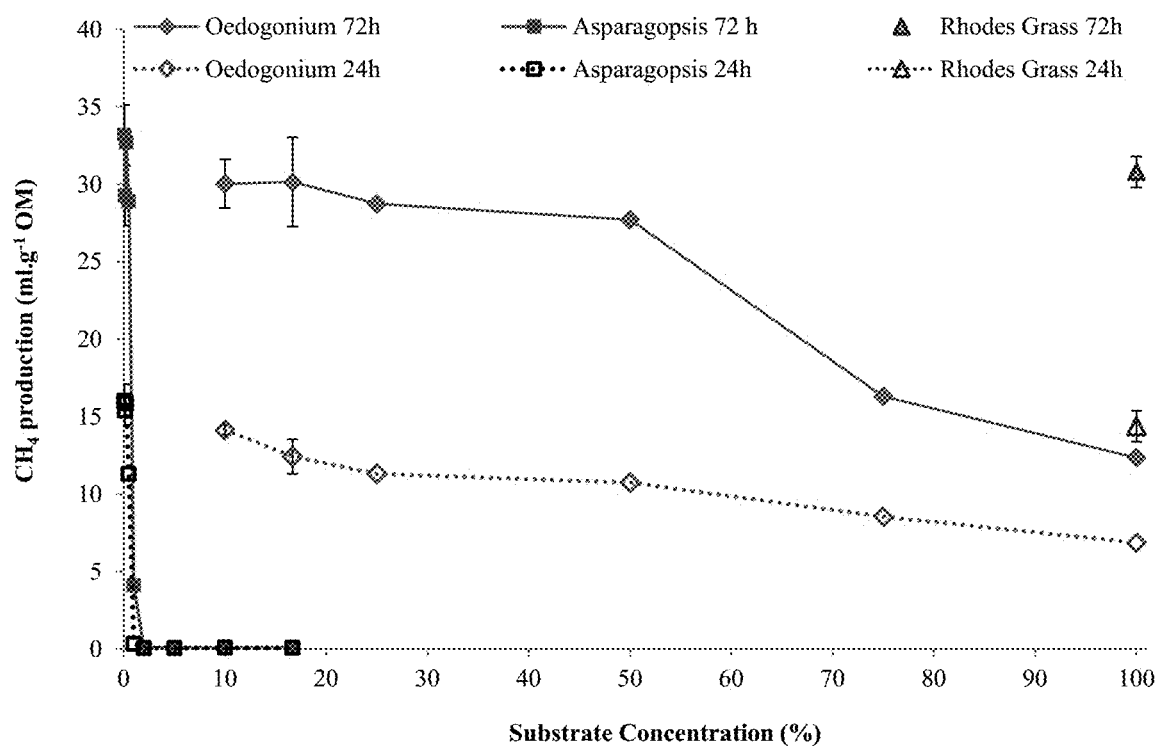
FIG. 11 shows average $CH_4$ production in (ml·g$^{-1}$ OM) of *Asparagopsis*, *Oedogonium*, and Rhodes grass (control) at 24 and 72 h of anaerobic incubation in vitro. Error bars represent ±SE. This figure demonstrates *Asparagopsis* reduces $CH_4$ production from anaerobic fermentation. This figure also demonstrates *Asparagopsis* reduces $CH_4$ production from anaerobic fermentation in a dose dependent manner. Error bars represent ±SE.

A multivariate CART model was produced to investigate the direct effects of biochemical parameters on the main fermentation parameters, TGP, $CH_4$ production, acetate and propionate concentrations (FIG. 4). The best tree model, explaining 79.1% of the variability in the data, showed that zinc was the independent variable with the highest relative importance (100%), splitting *Asparagopsis* and *Dictyota*, which had a concentration of zinc≥0.099 g·kg–1 DM, from the remaining species (Table 1). These two species had the lowest TGP and $CH_4$ production and the highest proportion of propionate. However, *Halymenia* had a similar concentration of zinc, 0.099 g·kg$^{-1}$ DM and the highest TGP and $CH_4$ output of any species of red and brown macroalgae (Table 1). This suggests that a zinc threshold is interacting with other biochemical variables, specific to *Asparagopsis* and/or *Dictyota*, which affects these fermentation parameters. The lack of a linear relationship is also confirmed by the low correlation of zinc with the MDS space (r=0.21). For species with a concentration of zinc <0.099 g·kg$^{-1}$ DM, differences in polyunsaturated fatty acid (PUFA) concentration generated a second split, indicating that species with PUFA >12.64 g·kg$^{-1}$ DM had higher $CH_4$ production than species with PUFA concentration below this value. However, PUFA had a relative importance of 14.8% of zinc indicating that the influence of PUFA in the model was small.

Example 4: Administration of *Asparagopsis* Reduced Methane Production In Vivo

Four fistulated steers (Bos indicus, 320 to 380 Kg liveweight) were used for an in vivo feeding trial which was carried out at the Lansdown research station, CSIRO. All the animals were fistulated and trained in respiration chambers prior to the commencement of the experimental period. Initially steers were held on Flinders grass hay, in group pens (cattle yards) for four days. Subsequently, steers were divided into two groups and allocated to treatments group, control (Flinders grass hay only) and *Asparagopsis* supplementation. Selection of the dose of algae (2% of OM intake per day) was based on results obtained from a previous in vitro study investigating methane reduction potential. The steers were allocated into individual pens in the research station with ad libitum Flinders grass hay and water supply. Animals under algal supplement were dosed directly into the rumen before morning feed to ensure complete intake of the treatment seaweed and consistency of treatment intake between animals. The steers had an acclimation period of 14 days to the different diets before going into open-circuit respiration chambers for measurement of methane production over 48 h. Methane production of animals were also measured after 21 and 29 days of treatment to evaluate the efficacy of *Asparagopsis* in reducing methane production in animals over time. After 31 days the algal treatment ceased and the animals were reallocated to paddocks. Rumen samples were collected 4 h after algal treatment was insert intra-ruminally at day 1, 15, and 30 of algal treatment to evaluate changes in VFA production and acetate to propionate ratios. Live weight, and feed offered and refused were measured daily and total dry matter (DM) intake and total organic matter (OM) intake calculated to determine mean individual DM and OM intakes. Results are shown in FIGS. 14, 15, 16 and 17, and Table 9. At all time-points tested, mean methane production was reduced by over 10%. At days 15-18, mean methane production in cattle was reduced by over 15%.

Figure 14:
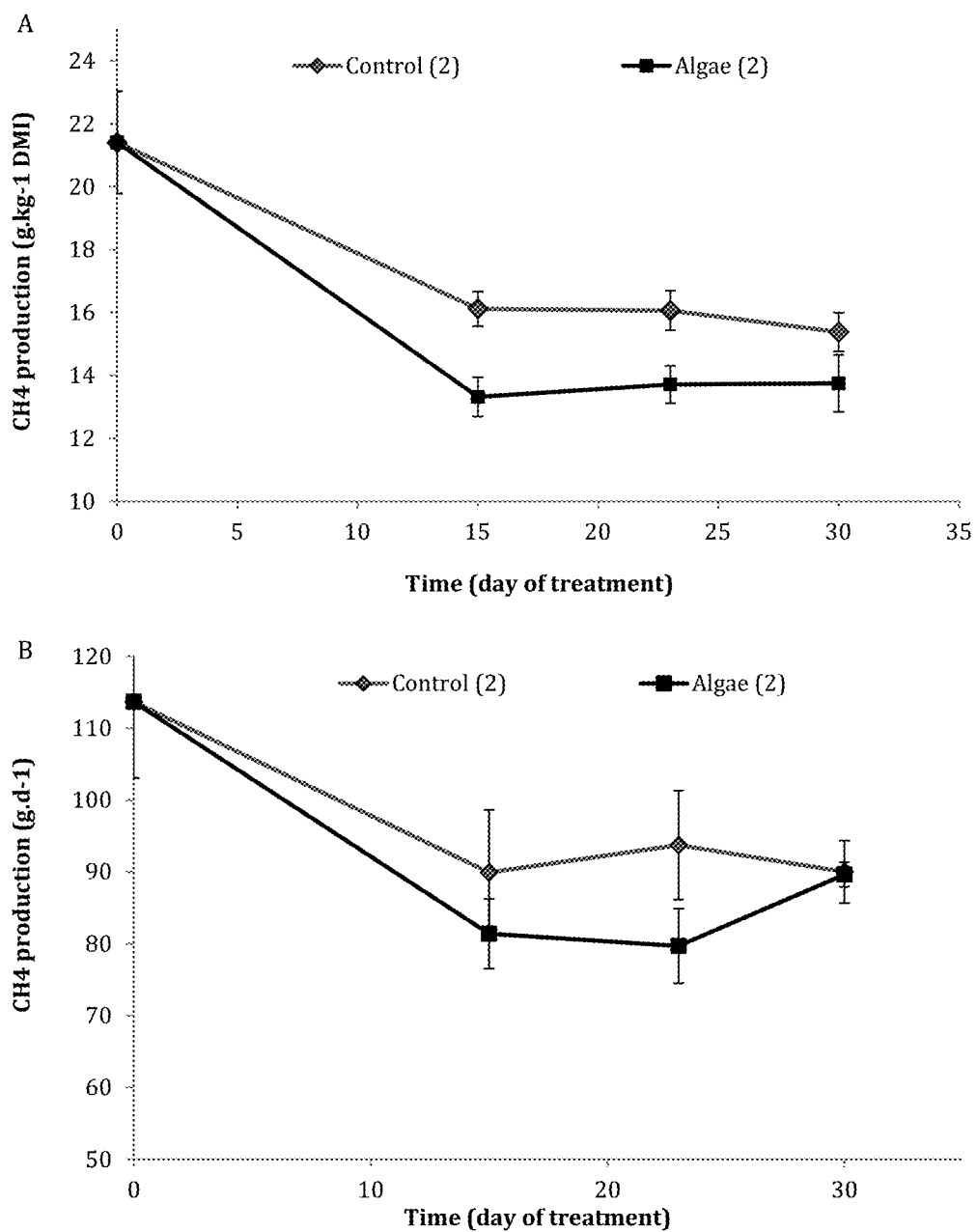
FIG. 14 shows mean methane production for steers fed a basal diet of Flinders grass (*Iseilema* sps.) or fed a basal diet of Flinders grass (*Iseilema* sps.) with *Asparagopsis*. Error bars represent SD. This figure demonstrates administration of *Asparagopsis* spp. reduces methane production in vivo in animals fed a low quality forage.
Figure 15:
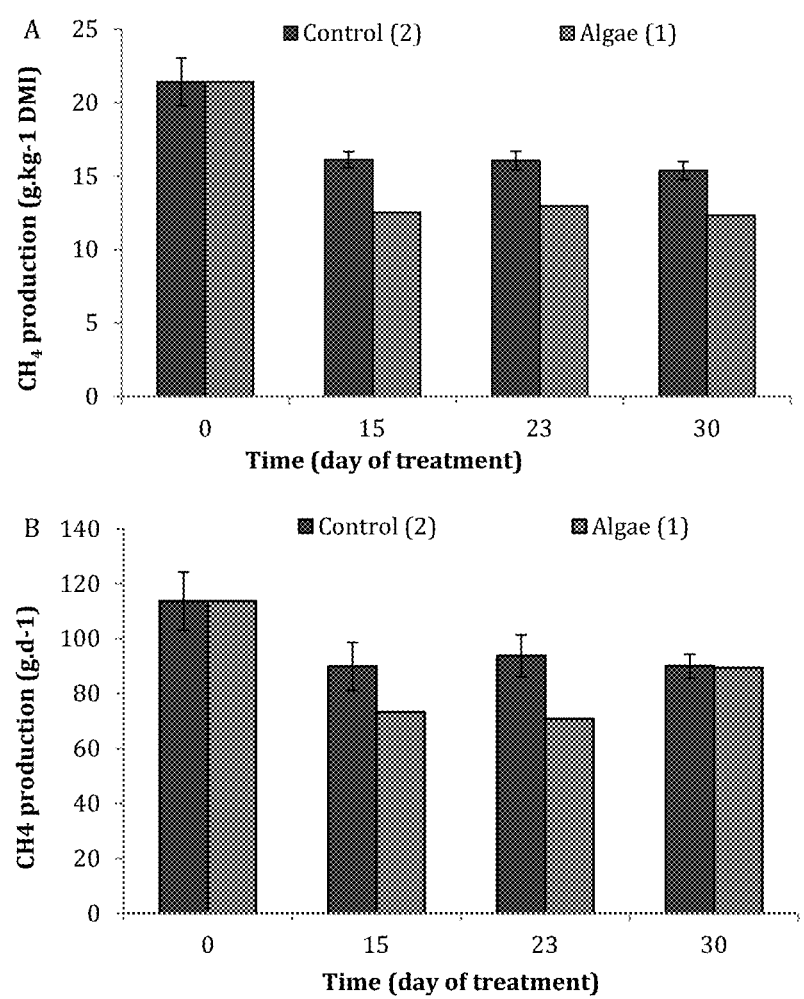
FIG. 15 shows mean methane production in $g \cdot kg^{-1}$ DMI (A) and $g \cdot d^{-1}$ (B) for a steer exhibiting a consistent response to the *Asparagopsis* treatment. This figure demonstrates *Asparagopsis* reduces methane production in vivo. Error bar represent ±SE. Number in parentheses indicates the number of steers per treatment.

Administration of *Asparagopsis* spp. is shown to reduce methane production in vivo in animals (FIG. 14). FIG. 15 shows mean methane production for the steer that responded best to the algal treatment. Importantly, as shown in FIG. 16, *Asparagopsis* does not reduce the dry matter degraded in vivo at doses of *Asparagopsis* that inhibit methane production in vivo. Furthermore, as shown in FIG. 17, *Asparagopsis* does not reduce the amount of VFAs at doses of *Asparagopsis* that inhibit methane production in vivo. However, this figure also demonstrates *Asparagopsis* increases the amount of propionate at doses of *Asparagopsis* that inhibit total gas and methane production at 15 and 30 days of treatment.

Example 5: Administration of *Asparagopsis* Reduced Methane Production In Vivo in Sheep Methodology The trial was conducted at the CSIRO Centre for Environment and Life Sciences Floreat WA between September and December 2014. The experimental protocol was approved by the local animal ethics committee (AEC1404).

Twenty four merino cross wethers [mean±sem live weight (LW); 65.8±1.03 kg] were allocated to one of five groups based on the daily inclusion rate (organic matter, OM basis) of the red macro algae *Asparagopsis* sp. (*Asparagopsis taxiformis*) [0 (control), 0.5, 1.0, 2.0, 3.0%]. Inclusion rates (% OM intake) were equivalent to 0, 13, 26, 58 and 80 g/d algae as fed, respectively.

Sheep were maintained under animal house conditions and fed a pelleted commercial shipper ration based on lupins, oats, barley, wheat with cereal straw as the roughage component [chemical composition (g/kg DM) of ash, 72; crude protein (CP) 112; neutral detergent fibre (aNDFom) 519; acid detergent fibre (ADFom) 338, and free of cobalt, selenium and rumen modifiers] at 1.2× maintenance throughout the study. All sheep were dosed with a Co bullet prior to the commencement of the experimental period.

Biomass of wild *Asparagopsis taxiformis* in the benthic gametophyte phase was collected from a site near Humpy Island, Keppel Bay (23° 13'S, 150° 54.8'E) on the Capricorn Coast. The biomass was initially air dried on ventilated racks in the shade followed by solar kiln drying (45-50° C.) to constant weight. The dried biomass was then packed in approximately 1.0 kg lots and sent to CSIRO Floreat. A sub sample of each algal batch was obtained for elemental and nutritional analysis. The remaining algal biomass was milled through a 5 mm sieve and re packed prior to inclusion in the daily ration. Sheep were gradually adapted to algal inclusion over an initial two weeks by mixing the ground material with 200 g crushed lupins (lupin diet). The algae/lupin mix was then added to the pelleted ration, mixed and fed for a further 75 d.

Feed intake was recorded daily and liveweight (LW) measured at 14 d intervals throughout the trial.

Three measurements of individual animal methane production (g/kg DM intake) were conducted, the first after 30 d algae inclusion and then at 21 d intervals throughout the trial period. During 24 h methane measurements using open circuit respiration chambers as described by Li (2013) [PhD thesis; *Eremophila glabra* reduced methane production in sheep, University of Western Australia] feed on offer (pellets/lupins) was proportionally reduced to 1.0× maintenance to ensure consistent intakes.

Following each methane measurement, up to 50 mL rumen fluid was collected by stomach tube for the determination of volatile fatty acid (VFA) concentration.

Statistical Analysis

The statistical analysis was conducted by fitting linear mixed models to each response variable. These models were able to account for the design of the experiment (the allocation of animals to particular groups and chambers), the structure of the data (repeated measures) and the missing values which occurred. The "fixed effects" in the mixed model consisted of the treatment effect (five inclusion rates of *Asparagopsis taxiformis*), the time effect (three sampling dates), the treatment by time interaction, and any covariates. Initial live weight was included as a covariate when analysing live weight. It was also tested as a potential covariate for other response variables, but was not significant, and so was not included in the final model.

The analysis produced means for all combinations of treatment and time, adjusted for all other terms in the model. P-values were calculated for testing the overall effect of time, treatment, and their interaction. Least significant differences (P=0.05) were calculated for comparing pairs of means.

Results

Biomass of wild *Asparagopsis taxiformis* in the benthic gametophyte phase collected from a site near Humpy Island, Keppel Bay contained approximately 0.22 mg/g DM halogenated metabolites, predominantly: 57% dibromoacetic acid; 26% bromoform; and 17% dibromochloromethane.

Sheep fed lower inclusion rates of *Asparagopsis* (<2.0%) consumed all the algae on a daily basis when mixed with a palatable carrier. Higher doses of *Asparagopsis* generally resulted in actual intakes of the milled algae material of approximately 30 g/d per sheep.

As shown in Table 10, inclusion of *Asparagopsis* in feed does not reduce the dry matter degraded in vivo in sheep, including at doses of *Asparagopsis* that inhibit methane production in vivo. Mean (±sem) daily DM intake across all groups was 1040±11.2 g/d over 75 days. Sheep provided with *Asparagopsis* at a rate of 0.5% consumed approximately 20 g/d more than control (0% *Asparagopsis*) animals. Sheep provided with *Asparagopsis* at a rate of 3.0% consumed approximately 20 g/d less than control (0% *Asparagopsis*) animals (Table 10). Although numerical differences between treatments exists, neither the treatment (algae dose) nor treatment×time effect was significant (P>0.05). Supplementing merino cross wethers with increasing levels of *Asparagopsis* from 0 to 3% (OM basis) did not affect mean daily DM intakes. These results indicate that inclusion of *Asparagopsis* in feed maintains the amount of dry matter degraded. These results also indicate that indicate that inclusion of *Asparagopsis* in feed does not compromise rumen fermentation.

As shown in Table 10, inclusion of *Asparagopsis* in feed does not affect animal liveweight of sheep, including at doses of *Asparagopsis* that inhibit methane production in vivo. Mean±sem live weight (LW) was 65.8±1.03 kg prior to allocation to one of five groups based on the daily inclusion rate of *Asparagopsis* sp. At the completion of the trial mean±sem live weight (LW) was 71.4±0.99 kg; as shown in Table 10, neither the treatment (algae dose) nor treatment×time effect was significant (P>0.05). Supplementing merino cross wethers with increasing levels of *Asparagopsis* from 0 to 3% (OM basis) did not affect animal liveweight. These results indicate that inclusion of *Asparagopsis* in feed does not affect animal liveweight. These results also indicate that indicate that inclusion of *Asparagopsis* in feed does not compromise rumen fermentation.

As shown in Table 11, inclusion of *Asparagopsis* in feed affects total VFA concentration and molar proportions of individual VFA, excluding iso-butyrate, in sheep. Total VFA concentration and molar proportions of short chain fatty acids are shown in Table 11. The overall treatment effect is highly significant (P<0.001) for total VFA concentration and molar proportions of individual VFA, excluding iso-butyrate. In contrast to the work with cattle described above in which cattle were provided with feed ad libitum, during the 24 hour measurement of methane and VFA production, sheep were placed on a restricted diet to ensure consistent feed intakes, and with the inclusion of *Asparagopsis* in feed, rather than administration directly into the rumen of fistulated animals (Example 4). Without being limited by theory, these differences may contribute to differences in total VFA levels observed. Fermentation in the sheep was not compromised, with liveweight not significantly different between control and treatment groups, as shown in Table 10.

Increasing inclusion rates of *Asparagopsis* in the daily ration resulted in a decrease in acetate (%) and increase in propionate (%) compared with the control; total VFA concentration and molar proportion of acetate was significantly higher for the control treatment (0%) compared to values associated with an inclusion of *Asparagopsis* in the daily ration, mean molar proportion of propionate was significantly higher suggesting an alternative hydrogen sink in the rumen when *Asparagopsis* was included in the daily ration compared with values associated with the control group. Importantly, these results indicate that inclusion of *Asparagopsis* in feed does not negatively affect the molar concentration of propionate. Inclusion of *Asparagopsis* in feed increases the amount of propionate, including at doses of *Asparagopsis* that inhibit methane production in vivo.

The inclusion of *Asparagopsis* in feed also significantly decreased the mean acetate: propionate ratio; the mean acetate:propionate was significantly higher for the control compared with *Asparagopsis* treatment groups. There was no significant difference in the acetate:propionate between *Asparagopsis* treatment groups. Sheep supplemented with 1.0% or 3.0% *Asparagopsis* (OM basis) had numerically lower acetate: propionate which corresponded to higher molar proportions of propionate (31.5% and 32%, respectively). These results indicate that inclusion of *Asparagopsis* in feed maintains effective levels of desirable volatile fatty acids.

As shown in FIG. 18, the inclusion of *Asparagopsis* in feed also significantly decreased methane production by the sheep. Individual methane emissions (g/kg DM intake) were measured after an initial 30 d period of algae inclusion in the diet and then at 21 d intervals over the experimental period (FIG. 18). The inclusion of *Asparagopsis* in the diet had a significant effect (P<0.001) on methane production compared to the control. Mean methane production from control (0% *Asparagopsis*) sheep was 14.6 g/kg DM intake, compared with 12.8, 6.8, 5.7 and 2.9 g/kg DM intake for sheep supplemented with *Asparagopsis* at inclusion rates of 0.5, 1.0, 2.0 and 3.0% (OM basis), respectively. There was no significant difference (P>0.05) in methane emissions for control and *Asparagopsis* inclusion at 0.5% (OM basis). There was no significant difference (P>0.05) in methane emissions for *Asparagopsis* inclusion at 1.0% when compared to methane emissions for *Asparagopsis* inclusion at 2.0% (OM basis).

The inclusion rates of *Asparagopsis* in feed at 1.0%, 2.0% and 3.0% (OM basis) demonstrated consistent reductions in methane emissions at each time point compared with the control, equivalent to 53%, 62% and 80%, respectively. In sheep, there was no significant effect of *Asparagopsis* inclusion over time on mean methane production, although after 72 d of inclusion at 0.5% mean emissions decreased numerically by 35% compared to 30 d and 51 d.

These results indicate that methane production is reduced in sheep administered *Asparagopsis*.

Example 6: Administration of *Asparagopsis* Reduced Methane Production In Vivo in Cattle The effect of increasing inclusion rates of *Asparagopsis* in the daily ration was examined in Brangus steers using a protocol adapted from the methods described above at Example 5.

Figure 19:
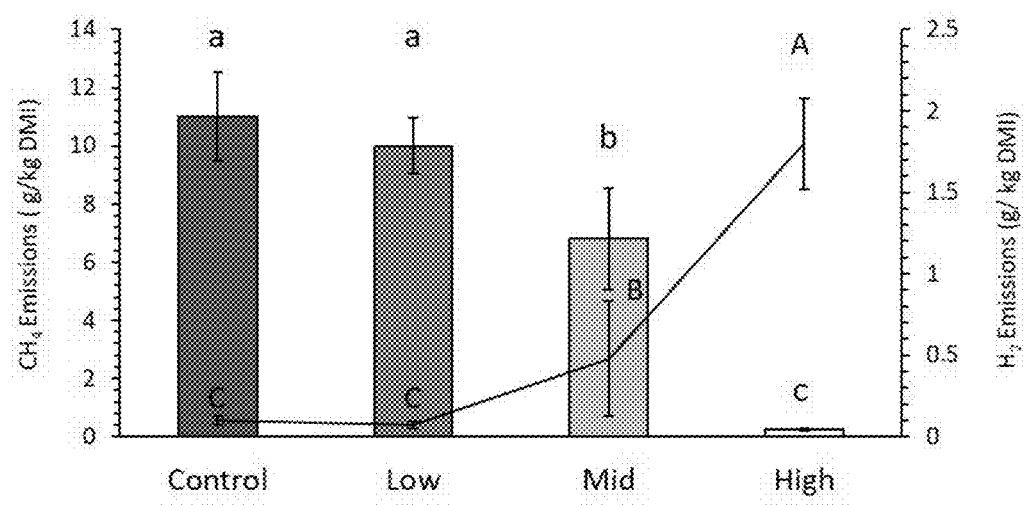
FIG. 19 shows methane ($CH_4$) and hydrogen ($H_2$) emissions as produced by Brangus steers consuming a feedlot total mixed ration with increasing *Asparagopsis taxiformis* inclusion at the four dose levels of 0.00, 0.05, 0.10, and 0.20% of organic matter intake. Columns ($CH_4$) and line points ($H_2$) identified with different letters were significantly different at $P<0.05$. This figure demonstrates *Asparagopsis* reduces methane production in vivo.

FIG. 19 shows methane ($CH_4$) and hydrogen ($H_2$) emissions produced by Brangus steers consuming a feedlot total mixed ration with increasing *Asparagopsis taxiformis* inclusion at the four dose levels of 0.00, 0.05, 0.10, and 0.20% of organic matter intake. Columns ($CH_4$) and line points ($H_2$) identified with different letters were significantly different at P<0.05.

These results indicate that methane production is reduced in cattle administered *Asparagopsis* at an inclusion rate of 0.10% and 0.2% of organic matter intake.

FIG. 20 shows the inclusion of *Asparagopsis* at 0.05, 0.10, and 0.20% of organic matter intake maintains total VFA concentration in cattle. Importantly, these results indicate that inclusion of *Asparagopsis* in feed increases maintains the total level of VFAs, including at doses of *Asparagopsis* that inhibit methane production in vivo.

FIG. 21 shows the inclusion of *Asparagopsis* at 0.05, 0.10, and 0.20% of organic matter intake changes levels of acetate and propionate, and the acetate:propionate ratio. The inclusion of *Asparagopsis* in feed significantly decreased the mean acetate:propionate ratio; the mean acetate:propionate was significantly higher for the control compared with *Asparagopsis* treatment groups at inclusion at 0.10% and 0.20% of organic matter intake.

FIG. 21 also shows *Asparagopsis* in feed resulted in a decrease in acetate (%) and increase in propionate (%) compared with the control. No trend or difference was observed for N-butyrate. Importantly, these results indicate that inclusion of *Asparagopsis* in feed resulted in a decrease in acetate (%) and increase in propionate (%) while maintaining total levels of VFAs, including at doses of *Asparagopsis* that inhibit methane production in vivo.

Example 7: Halogenated Metabolites in *Asparagopsis taxiformis* and *Asparagopis armata*

Figure 22:
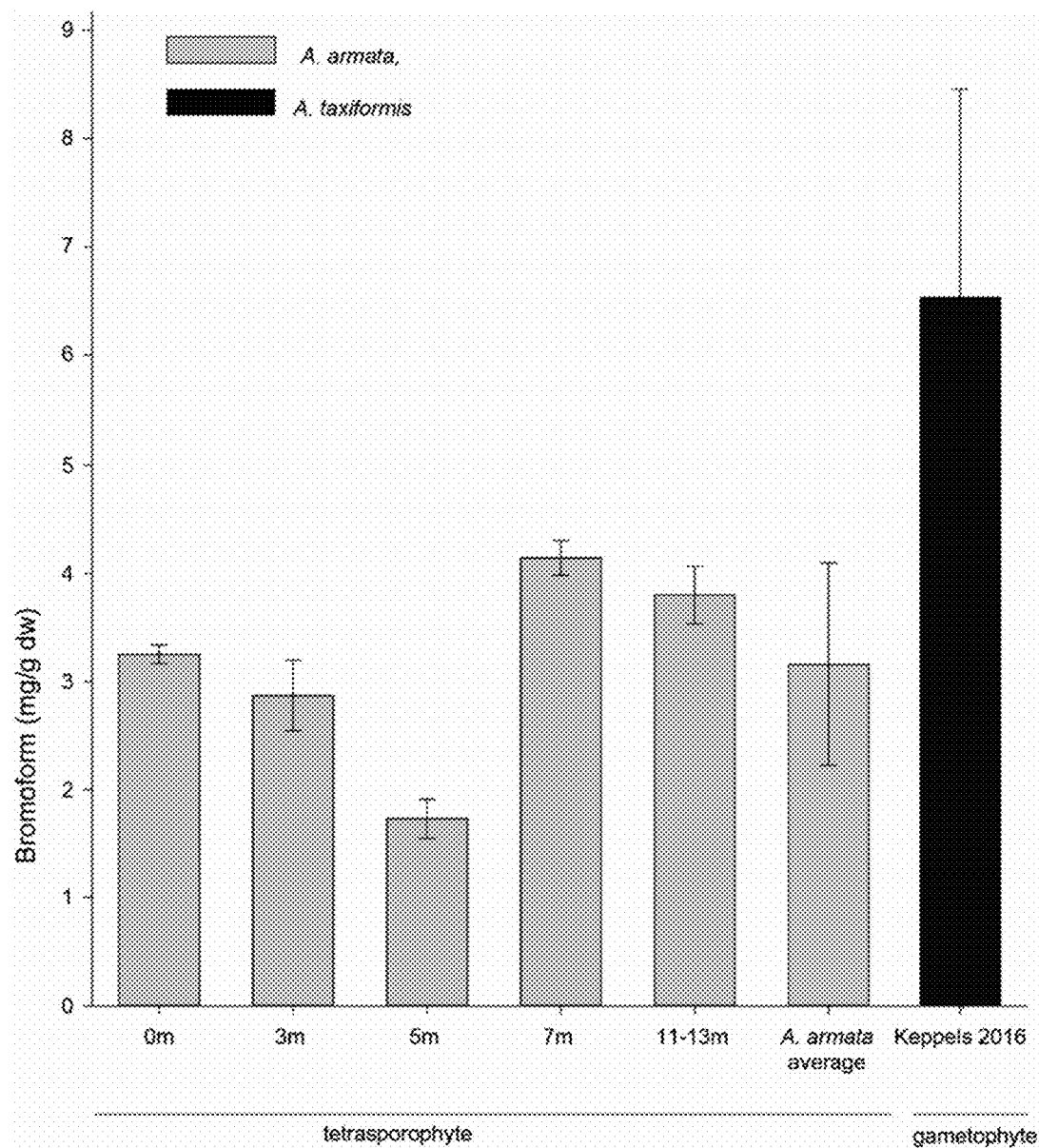
FIG. 22 shows *Asparagopsis taxiformis* and *Asparagopsis armata* contain bromoform. Biomass of *Asparagopsis taxiformis* gametophyte stage collected from a site near Humpy Island, Keppel Bay contained approximately 6.55+/−1.86 mg/g dry weight bromoform ("Kappels 2016"), and biomass of *Asparagopsis armata* contained an average of approximately 3.16+/−90 mg/g bromoform ("*A. armata* average"), a halogenated metabolite. Depths in meters is shown for collection depths of *Asparagopsis armata* tetrasporporophyte stage.

*Asparagopsis* produces halogenated low molecular weight compounds, in particular brominated and chlorinated haloforms. Many of these compounds have strong antimicrobial properties and inhibit a wide range of microorganisms, including Gram-positive and Gram-negative bacteria, as well as, mycobacterium and fungus activities, and therefore may be involved in contributing to the effects described herein. Secondary metabolites from *Asparagopsis* also inhibit protozoans. The levels of halogenated metabolites, including bromoform, were examined in *Aspragopsis* spp. using the methods described herein (e.g. Examples 1, 2 and 3). *Asparagopsis armata* was collected from Cloudy Bay, Bruny Island, Tasmania, 43°.43'94" S; 147°.21'.52" E As demonstrated in Example 5, biomass of wild *Asparagopsis taxiformis* in the benthic gametophyte phase collected from a site near Humpy Island, Keppel Bay contained approximately 0.22 mg/g DM halogenated metabolites, predominantly: 57% dibromoacetic acid; 26% bromoform; and 17% dibromochloromethane. FIG. 22 shows biomass of *Asparagopsis armata* contains bromoform. These results indicate that *Asparagopsis taxiformis* and *Asparagopis armata* contain similar levels of the halogenated metabolite bromoform.

Example 8: Total Gas Production and Methane Production Using *Asparagopsis armata*

Total gas production (TGP) and methane production from anaerobic fermentation in vitro in the presence of *Asparagopsis armata, Asparagopsis taxiformis* and Rhodes grass (control) were examined using the methods described herein (e.g. Example 2 and Example 3).

Figure 23:
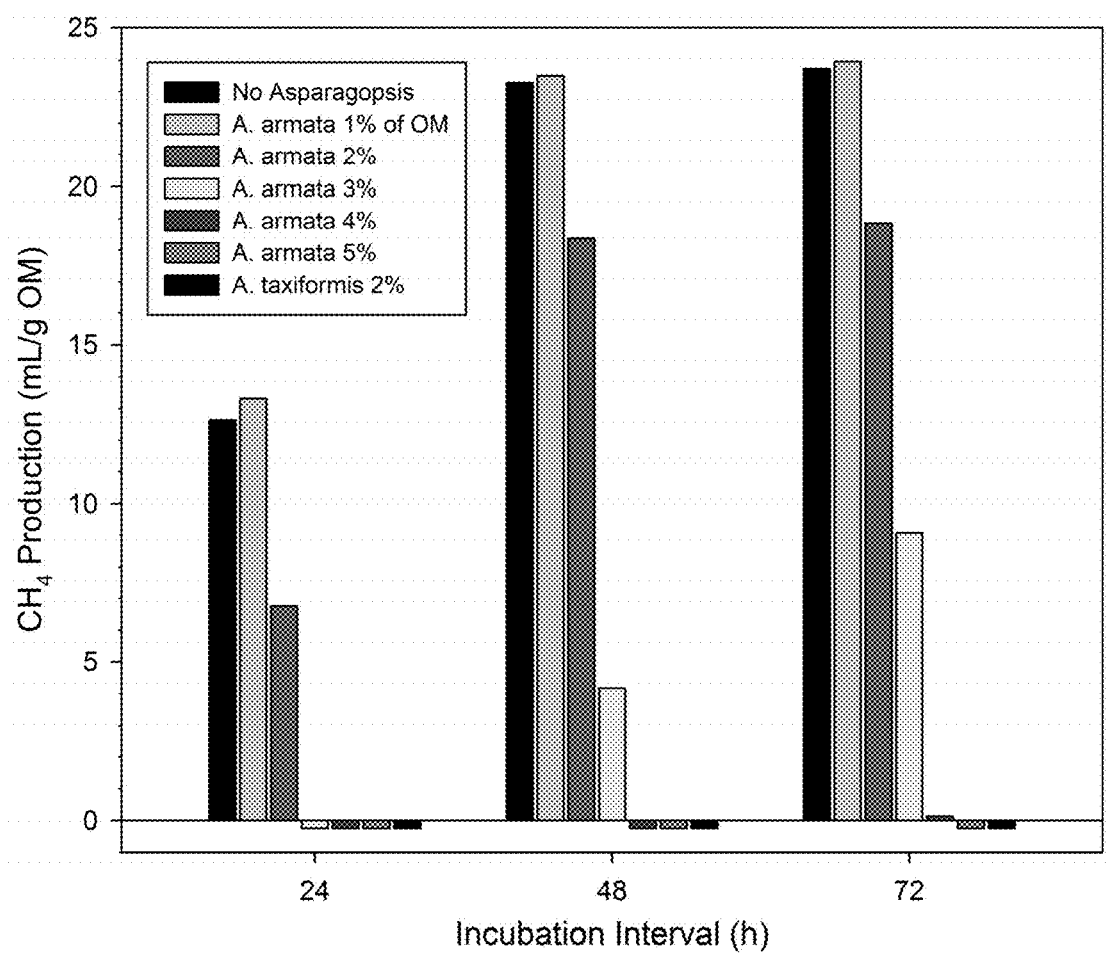
FIG. 23 shows average $CH_4$ production in ($ml \cdot g^{-1}$ OM) of *Asparagopsis armata* and *Asparagopsis taxiformis* and Rhodes grass (control) at 24, 48 and 72 h of anaerobic incubation in vitro. This figure demonstrates *Asparagopsis*, including *Asparagopsis armata*, reduces $CH_4$ production from anaerobic fermentation. This figure also demonstrates *Asparagopsis armata* reduces $CH_4$ production from anaerobic fermentation in a dose dependent manner. Where no $CH_4$ could be detected, a fictitious emission value if −0.25 $ml \cdot g^{-1}$ was assigned to that the representative column could be located.
Figure 24:
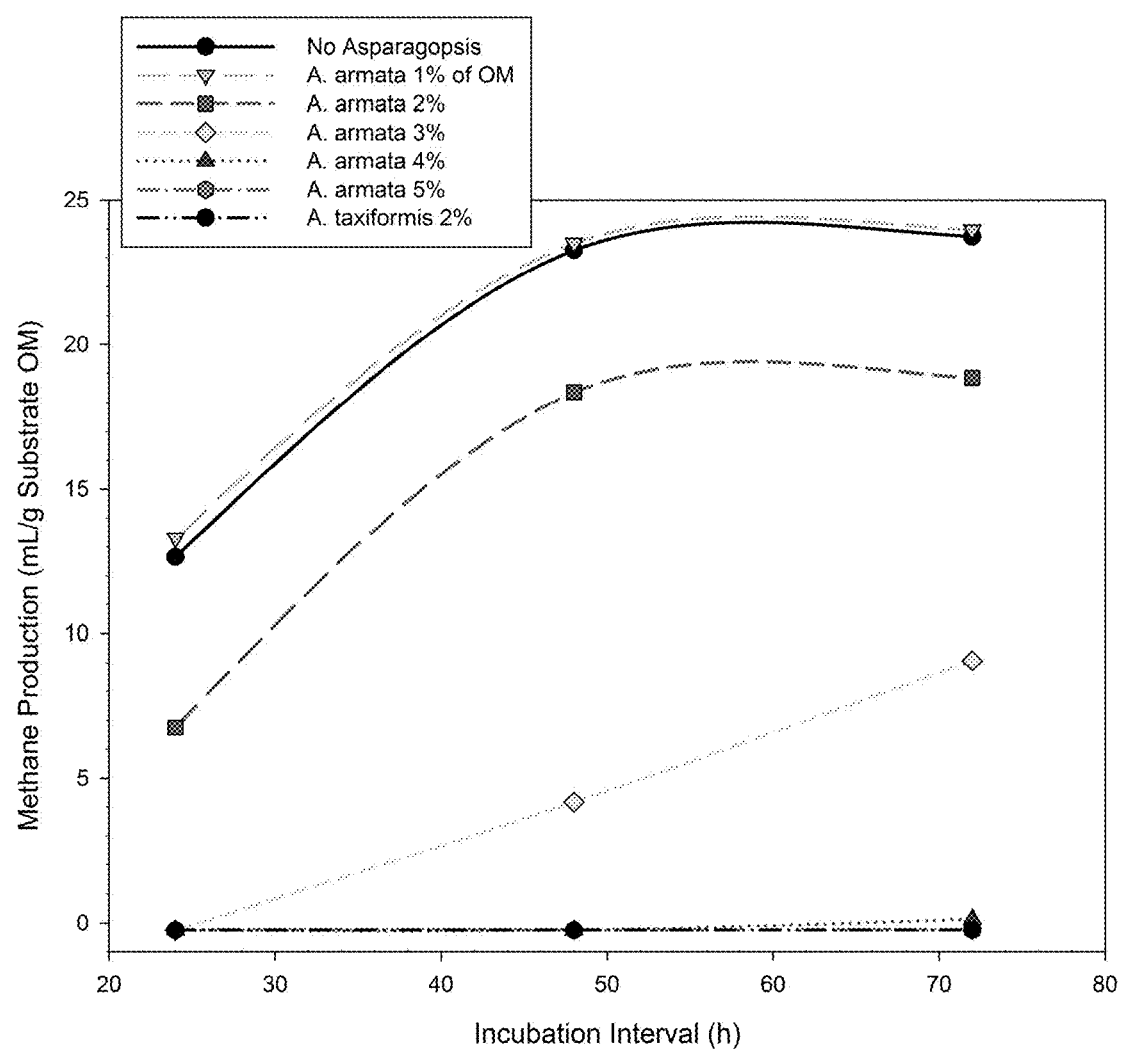
FIG. 24 shows average $CH_4$ production in ($ml \cdot g^{-1}$ OM) from anaerobic fermentation in vitro in the presence of *Asparagopsis armata*, *Asparagopsis taxiformis* and Rhodes grass (control) at 24, 48 and 72 h of anaerobic incubation in vitro. This figure demonstrates *Asparagopsis*, including *Asparagopsis armata*, reduces $CH_4$ production from anaerobic fermentation. This figure also demonstrates *Asparagopsis armata* reduces $CH_4$ production from anaerobic fermentation in a dose dependent manner. There are three curves grouped at zero where no $CH_4$ could be detected (*A. armata* at 4% and 5%, and *A. taxiformis* at 2%).

As shown in FIGS. 23 and 24, $CH_4$ production using *Asparagopsis armata* and *Asparagopsis taxiformis* was reduced compared to control. At 24 hours, *A. armata* at 2% of organic matter (OM) reduced methane production by about 50%, whereas *A. armata* at 3%, 4% and 5% (and *A. taxiformis* at 2%) of OM reduced methane production by 100%. At 48 hours, *A. armata* at 2% of OM reduced methane production by about 25%, *A. armata* at 3% of OM reduced methane production by about 83% whereas *A. armata* at 4% and 5% (and *A. taxiformis* at 2%) of OM reduced methane production by 100%. At 72 hours, *A. armata* at 2% of OM reduced methane production by about 25%, *A. armata* at 3% of OM reduced methane production by about 63% whereas *A. armata* at 4% and 5% (and *A. taxiformis* at 2%) of OM reduced methane production by about 100%. This data demonstrates *Asparagopsis*, including *Asparagopsis armata*, reduces $CH_4$ production from anaerobic fermentation, in a dose dependent manner.

Figure 25:
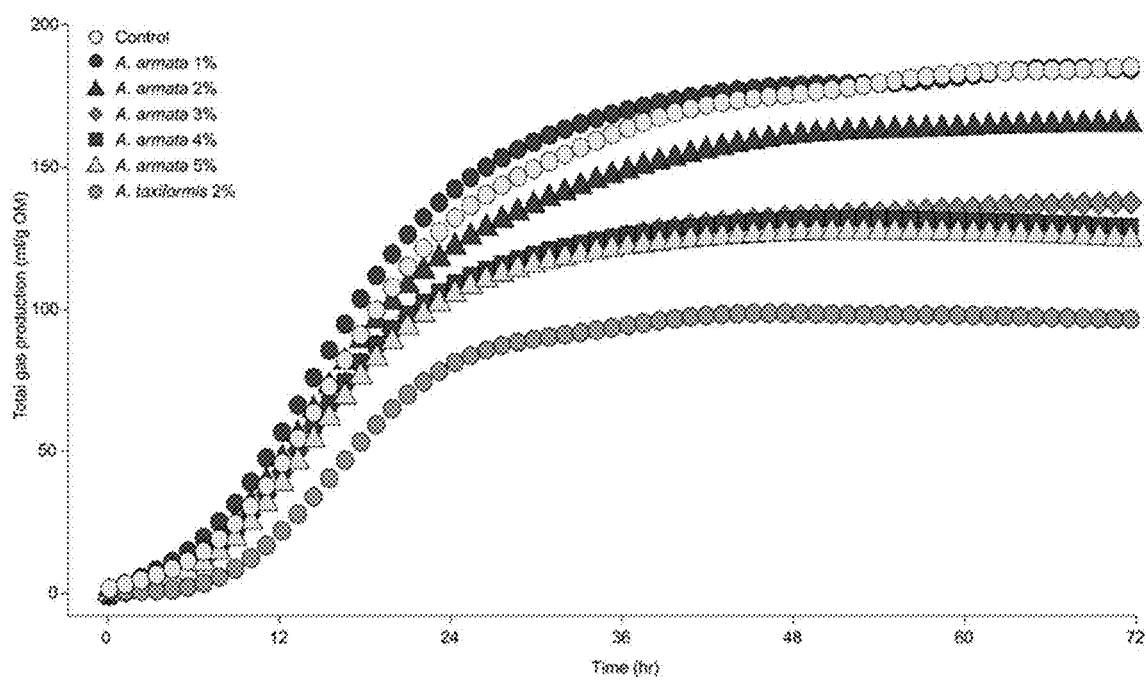
FIG. 25 shows total gas production (TGP) ($ml \cdot g^{-1}$ OM) from anaerobic fermentation in vitro in the presence of *Asparagopsis armata*, *Asparagopsis taxiformis* and Rhodes grass (control) over a 72 h incubation period. This figure demonstrates *Asparagopsis* spp. reduce total gas production from anaerobic fermentation. This figure also demonstrates *Asparagopsis* reduces TGP from anaerobic fermentation in a dose dependent manner.

As shown in FIG. 25, TGP generally followed the same pattern as $CH_4$ production. FIG. 25 shows total gas production (TGP) (ml·$g^{-1}$ OM) from anaerobic fermentation in vitro in the presence of *Asparagopsis armata, Asparagopsis taxiformis* and Rhodes grass (control) over a 72 h incubation period. TGP using *Asparagopsis armata* and *Asparagopsis taxiformis* was reduced compared to control, using levels of *A. armata* at 2% of OM or above. This data demonstrates *Asparagopsis* spp. including *Asparagopsis armata*, reduce total gas production from anaerobic fermentation, in a dose dependent manner.

TABLE 1

Biochemical parameters correlated with MDS and CARTs analyses for TGP and $CH_4$ production.

| Macroalgae species | Ash | C | GE (MJ | H | Total | K | N | Sr | PUFA | C | Ca | Na | S | Zn |
|---|---|---|---|---|---|---|---|---|---|---|---|---|---|---|
| Freshwater algae | | | | | | | | | | | | | | |
| Cladophora vagabunda | 158. | 380. | 16.1 | 57. | 49.6 | 33. | 54. | 0.0 | 21.1 | 8.67 | 4.2 | 2.8 | 11. | 0.02 |
| Oedogonium sp. | 64.1 | 447. | 19.4 | 66. | 57.7 | 13. | 49. | 0.0 | 35.1 | 11.4 | 2.9 | 0.4 | 2.9 | 0.05 |
| Spirogyra sp. | 167. | 372. | 15.2 | 57. | 27.8 | 5.6 | 14. | 0.1 | 16.0 | 7.39 | 16. | 38. | 3.1 | 0.01 |
| Marine green algae | | | | | | | | | | | | | | |
| Caulerpa taxifolia | 269. | 320. | 13.1 | 48. | 25.5 | 6.4 | 32. | 0.0 | 13.2 | 7.81 | 3.8 | 82. | 22. | 0.01 |
| Chaetomorpha linum | 254. | 322. | 12.9 | 48. | 21.0 | 86. | 42. | 0.0 | 10.7 | 5.08 | 4.5 | 10 | 21. | 0.06 |
| Cladophora coelothrix | 234. | 361. | 15.3 | 55 | 30.8 | 38. | 52. | 0.0 | 12.6 | 7.2 | 7.8 | 3.9 | 21 | 0.03 |
| Cladophora | 365 | 292. | 11.2 | 42. | 15.5 | 60. | 23. | 0.1 | 4.34 | 5.18 | 17. | 3.4 | 32. | 0.02 |
| Derbesia tenuissima | 77.5 | 449. | 20.1 | 66. | 48.7 | 9 | 66. | 0.0 | 19.1 | 17.2 | 2.7 | 8.2 | 12. | 0.03 |
| Ulva sp. | 206. | 322. | 13.6 | 54. | 25.6 | 20. | 47. | 0.1 | 12.6 | 7.95 | 10. | 8.4 | 28. | 0.03 |
| Ulva ohnoi | 211. | 291. | 12 | 55. | 14.7 | 21. | 43 | 0.0 | 4.3 | 5.37 | 4.5 | 5.4 | 57. | 0.04 |
| Brown algae | | | | | | | | | | | | | | |
| Cystoseira trinodis | 266. | 317. | 12.1 | 46. | 18.6 | 85. | 18. | 1.2 | 6.92 | 6.19 | 16. | 17. | 13. | 0.01 |
| Dictyota bartayresii | 300. | 332. | 12.9 | 46. | 27.0 | 27 | 17. | 1.1 | 9.93 | 7.15 | 35. | 5.3 | 12 | 0.09 |
| Hormophysa triquetra | 303. | 296. | 10.7 | 41. | 18.7 | 30. | 7.9 | 0.9 | 11.1 | 3.4 | 21. | 6 | 13. | 0.06 |
| Padina australis | 385. | 243. | 8.7 | 38. | 18.3 | 81. | 11 | 1.5 | 7.73 | 5.06 | 21. | 18. | 33. | 0.01 |
| Sargassum flavicans | 255. | 305 | 11.7 | 46. | 13.9 | 78. | 8.4 | 1.7 | 5.67 | 3.86 | 20. | 11. | 9.6 | 0.01 |
| Colpomenia sinuosa | 409. | 270. | 9.9 | 38. | 18.3 | 80. | 14. | 1.5 | 4.86 | 5.34 | 56. | 15. | 7.2 | 0.05 |
| Red algae | | | | | | | | | | | | | | |
| Asparagopsis taxiformis | 189. | 384 | 16.4 | 58. | 27.2 | 14. | 55. | 0.0 | 10.1 | 10.7 | 6.1 | 12. | 26. | 0.15 |
| Halymenia floresii | 277. | 288. | 11.5 | 48. | 12.9 | 36. | 21. | 0.0 | 2.92 | 6.55 | 3.9 | 36 | 55. | 0.09 |
| Hypnea pannosa | 473. | 220 | 7.5 | 34. | 16.0 | 19. | 14. | 0.4 | 6.37 | 5.16 | 32. | 54. | 41. | 0.02 |
| Laurencia filiformis | 359. | 290. | 11.5 | 44. | 11.9 | 12. | 18. | 0.3 | 3.34 | 4.19 | 26 | 64 | 27. | 0.02 |
| DCS | 199 | 427. | 18.6 | 64. | 26.5 | 15. | 79. | 0.0 | 13.2 | 6.64 | 1.9 | 2.1 | 3.1 | 0.05 |
| SEM | 0.36 | 6.66 | 1.11 | 0.1 | 1.29 | 3.0 | 0.2 | 0.7 | 0.8 | 0.34 | 1.4 | 2.4 | 1.7 | 7.35 |
| r | 0.98 | 0.98 | 0.92 | 0.9 | 0.81 | 0.7 | 0.7 | 0.7 | 0.79 | 0.73 | 0.7 | 0.7 | 0.7 | 0.21 |

Parameters were calculated in $g \cdot kg^{-1}$ DM, unless otherwise stated. For TGP and $CH_4$ production, (n = 3-4). r = Pearson's correlation coefficients from MDS analysis. C, carbon; GE, gross energy content; H, hydrogen; Total FA, total fatty acids; K, potassium; N, nitrogen; Sr, strontium; PUFA, total polyunsaturated fatty acids; C16:0, palmitic acid; Ca, calcium; Na, sodium; S, sulfur; Zn, zinc; DCS, decorticated cottonseed meal; SEM, standard error mean.

TABLE 2

Post-fermentation parameters correlated with MDS and CARTs analyses for TGP and $CH_4$ production.

| Macroalgae | TGP ($mL \cdot g^{-1}$ OM) | $CH_4$ ($mL \cdot g^{-1}$ OM) | $CH_4$/G ($mL \cdot L^{-1}$) | Volatile Fatty acids (molar proportion) | | | | | | | | | |
|---|---|---|---|---|---|---|---|---|---|---|---|---|---|
| | | | | Total (mmol/l) | C2 | C3 | IsoC4 | C4 | IsoC5 | C5 | C2:C3 | pH | $NH_3$— ($mg \cdot L^{-1}$) | OM (%) |
| Freshwater | | | | | | | | | | | | | | |
| C. | 106.8[ab] | 14.3[a] | 133.9 | 28.52 | 63.9 | 26.2 | 0.73 | 7.84 | 0.32 | 0.9 | 2.49 | 6.9 | 9.00 | 63.8 |
| Oedogonium | 101.1[bc] | 12.6[b] | 125.0 | 32.26 | 66.4 | 24.2 | 0.67 | 7.28 | 0.45 | 0.9 | 2.79 | 6.9 | 7.60 | 64.5 |
| Spirogyra | 119.3[ab] | 17.3[a] | 144.8 | 36.59 | 66.2 | 23.6 | 0.45 | 8.58 | 0.50 | 0.5 | 2.82 | 6.8 | 8.20 | 62.5 |
| Marine | | | | | | | | | | | | | | |
| Caulerpa | 102.3[ab] | 12.2[b] | 119.7 | 33.46 | 67.0 | 23.2 | 0.58 | 8.05 | 0.48 | 0.5 | 2.90 | 6.9 | 8.60 | 58.6 |
| Chaetomorp | 99.8[bcd] | 10.9[b] | 109.3 | 28.81 | 62.2 | 28.8 | 0.45 | 7.29 | 0.24 | 0.8 | 2.19 | 6.9 | 8.50 | 60.8 |
| C coelothrix | 112.6[ab] | 13.2[a] | 116.9 | 27.56 | 63.7 | 26.7 | 0.65 | 7.46 | 0.44 | 0.8 | 2.39 | 6.9 | 8.50 | 64.2 |
| C. | 79.7[de] | 6.1[cde] | 76.8 | 24.29 | 63.8 | 26.7 | 0.45 | 8.20 | 0.01 | 0.7 | 2.39 | 7.0 | 7.80 | 58.8 |
| Derbesia | 119.7[ab] | 16.3[a] | 136.0 | 25.18 | 66.1 | 24.3 | 0.78 | 7.42 | 0.54 | 0.8 | 2.76 | 6.9 | 9.40 | 65.0 |
| Ulva sp. | 99.0[bcd] | 9.0[bcd] | 91.1 | 28.57 | 63.4 | 26.6 | 0.66 | 7.76 | 0.47 | 0.9 | 2.41 | 6.9 | 8.00 | 61.3 |
| U. ohnoi | 89.0[cd] | 9.9[bcd] | 111.6 | 26.02 | 65.8 | 24.4 | 0.81 | 7.32 | 0.62 | 0.9 | 2.71 | 6.9 | 7.20 | 61.4 |
| Brown | | | | | | | | | | | | | | |
| Cystoseira | 96.8[bcd] | 9.9[bc] | 102.5 | 19.64 | 59.7 | 32.0 | 0.10 | 7.84 | 0.03 | 0.2 | 2.01 | 6.9 | 8.10 | 58.5 |
| Dictyota | 59.4[ef] | 1.4[de] | 23.6 | 17.03 | 60.9 | 35.9 | 0.06 | 2.81 | 0.00 | 0.2 | 1.73 | 7.1 | 7.90 | 58.0 |
| Hormophysa | 104.8[ab] | 10.2[b] | 97.0 | 21.24 | 64.9 | 28.0 | 0.14 | 6.39 | 0.04 | 0.3 | 2.37 | 6.9 | 7.70 | 62.0 |
| Padina | 97.4[bcd] | 9.0[cd] | 92.4 | 24.56 | 65.2 | 26.0 | 0.35 | 7.49 | 0.19 | 0.7 | 2.53 | 6.9 | 7.00 | 60.0 |
| Sargassum | 113.6[ab] | 11.9[b] | 105.0 | 29.23 | 66.4 | 24.4 | 0.45 | 8.03 | 0.27 | 0.3 | 2.77 | 6.8 | 7.70 | 60.7 |
| Colpomenia | 95.8[bcd] | 9.2[bcd] | 95.5 | 23.06 | 62.7 | 29.0 | 0.30 | 7.50 | 0.00 | 0.2 | 2.16 | 6.9 | 8.10 | 61.8 |
| Red algae | | | | | | | | | | | | | | |
| Asparagopsis | 48.4[f] | 0.2[e] | 4.3 | 14.79 | 39.9 | 40.2 | 0.00 | 19.2 | 0.00 | 0.5 | 0.92 | 7.0 | 6.70 | 59.2 |
| Halymenia | 114.0[ab] | 13.3[a] | 116.3 | 22.52 | 64.6 | 23.9 | 0.83 | 8.96 | 0.65 | 0.9 | 2.71 | 6.9 | 8.30 | 61.4 |
| Hypnea | 101.9[ab] | 10.4[b] | 102.1 | 28.44 | 66.3 | 23.9 | 0.58 | 7.77 | 0.41 | 0.6 | 2.78 | 6.9 | 6.70 | 60.8 |
| Laurencia | 96.1[bcd] | 10.9[b] | 113.0 | 24.36 | 65.7 | 25.3 | 0.33 | 8.12 | 0.08 | 0.3 | 2.59 | 6.9 | 7.70 | 61.1 |

TABLE 2-continued

Post-fermentation parameters correlated with MDS and CARTs analyses for TGP and CH$_4$ production.

| Macroalgae | TGP (mL · g$^{-1}$ OM) | CH$_4$ (mL · g$^{-1}$ OM) | CH$_4$/G (mL · L$^{-1}$) | Volatile Fatty acids (molar proportion) | | | | | | | | | NH$_3$— (mg · L$^{-1}$) | OM (%) |
|---|---|---|---|---|---|---|---|---|---|---|---|---|---|---|
| | | | | Total (mmol/l) | C2 | C3 | IsoC4 | C4 | IsoC5 | C5 | C2:C3 | pH | | |
| DCS | 126.8$^a$ | 18.1$^a$ | 142.9 | 27.80 | 64.0 | 25.5 | 0.80 | 7.89 | 0.63 | 1.1 | 2.55 | 6.9 | 9.50 | 64.5 |
| SEM | 2.29 | 0.61 | 4.60 | 0.94 | 0.75 | 0.63 | 0.37 | 0.31 | 0.04 | 0.0 | 0.06 | 0.0 | 0.11 | 0.49 |
| r | 0.19 | 0.42 | 0.34 | 0.37 | 0.23 | 0.34 | 0.43 | 0.17 | 0.62 | 0.4 | 0.35 | 0.1 | 0.59 | 0.55 |

For TGP and CH$_4$ production, (n = 3-4) species not connected by the same letters within the same column are significantly different. r = Pearson's correlation coefficients from MDS analysis; C2, acetate; C3, propionate; C4, butyrate; Iso C4, Iso-butyrate; C5, valerate; Iso C5, Iso - valerate C2:C3, acetate/propionate ratio; OMd, organic matter degraded; DCS, decorticated cottonseed meal; SEM, standard error mean.

TABLE 3

Proximate analysis of freshwater and marine macroalgae species, decorticated cottonseed meal (DCS) and Flinders grass hay.

| Species | Site | FW:DW | DM | OM | CP | TL | Carbohydrates | Ash | GE (MJ · kg$^{-1}$ DM) |
|---|---|---|---|---|---|---|---|---|---|
| Freshwater algae | | | | | | | | | |
| Cladophora vagabunda | MARFU$^A$ | 6.31 | 940.87 | 841.11 | 278.56 | 96.76 | 406.66 | 158.89 | 16.08 |
| Oedogonium sp. | MARFU | 4.37 | 937.93 | 935.90 | 252.40 | 79.35 | 542.08 | 64.10 | 19.41 |
| Spirogyra sp. | GFB$^B$ Kelso | 11.98 | 926.84 | 832.35 | 75.41 | 52.09 | 631.69 | 167.65 | 15.18 |
| Green algae | | | | | | | | | |
| Caulerpa taxifolia | MARFU | 11.11 | 930.81 | 730.39 | 166.73 | 58.98 | 435.49 | 269.61 | 13.07 |
| Chaetomorpha linum | MARFU | 6.00 | 934.81 | 745.56 | 218.54 | 47.89 | 413.94 | 254.44 | 12.86 |
| Cladophora coelothrix | GFB$^B$ Bowen | 3.72 | 923.57 | 765.90 | 269.33 | 49.96 | 370.18 | 234.10 | 15.32 |
| Cladophora patentiramea | PR$^C$ | 4.45 | 938.31 | 635.04 | 122.61 | 26.07 | 424.67 | 364.96 | 11.22 |
| Derbesia tenuissima | MARFU | 8.10 | 919.27 | 922.52 | 339.09 | 130.13 | 372.55 | 77.48 | 20.14 |
| Ulva sp. | MARFU | 6.90 | 911.42 | 793.49 | 241.62 | 33.05 | 430.23 | 206.51 | 13.57 |
| Ulva ohnoi | MARFU | 6.52 | 907.00 | 788.74 | 220.59 | 24.56 | 450.59 | 211.26 | 12.02 |
| Brown algae | | | | | | | | | |
| Cystoseira trinodis | NB$^D$ | 6.39 | 919.95 | 733.33 | 98.45 | 35.22 | 524.18 | 266.67 | 12.09 |
| Dictyota bartayresii | NB and RB$^E$ | 6.74 | 945.44 | 699.27 | 96.30 | 112.82 | 440.06 | 300.73 | 12.86 |
| Hormophysa triquetra | NB | 5.73 | 925.32 | 696.93 | 42.50 | 33.94 | 547.78 | 303.07 | 10.68 |
| Padina australis | RB | 5.38 | 933.88 | 614.43 | 59.18 | 24.98 | 466.90 | 385.57 | 8.65 |
| Sargassum flavicans | NB | 6.80 | 925.19 | 744.19 | 45.19 | 27.21 | 599.08 | 255.81 | 11.67 |
| Colpomenia sinuosa | NB | 15.63 | 945.06 | 590.31 | 75.86 | 31.05 | 431.99 | 409.69 | 9.86 |
| Red algae | | | | | | | | | |
| Asparagopsis taxiformis | MARFU | 3.73 | 944.82 | 810.58 | 254.75 | 33.33 | 437.35 | 189.42 | 16.44 |
| Halymenia floresii | NB | 7.88 | 929.30 | 722.50 | 99.60 | 15.14 | 525.34 | 277.50 | 11.55 |
| Hypnea pannosa | NB | 10.40 | 935.74 | 526.65 | 65.64 | 28.51 | 360.52 | 473.35 | 7.54 |
| Laurencia filiformis | NB | 11.70 | 936.57 | 640.21 | 86.75 | 64.32 | 415.50 | 359.79 | 11.46 |
| DCS | — | — | 897.91 | 801.01 | 497.50 | 47.18 | 154.24 | 198.99 | 18.55 |
| Flinders grass | — | — | 925.92 | 875.76 | 27.50 | 28.68 | 745.51 | 124.24 | 15.51 |

$^A$Marine and Aquaculture Research Facility Unit, Macroalgal Biofuels and Bioproducts Research Group, James Cook University (19.33° S; 146.76° E);
$^B$Good Fortune Bay Fisheries, a barramundi farm (19.36° S; 146.70° E);
$^C$Pacific Reef Fisheries, Tiger prawn farm (19.58° S, 147.40° E);
$^D$Nelly Bay, an intertidal reef flat situated in Magnetic Island (19.16° S; 146.85° E),
$^E$Rowes Bay, an intertidal reef flat situated in Townsville (19.23° S, 146.79° E).

Parameters were calculated in g · kg$^{-1}$ DM, unless otherwise stated; FW:DW, fresh weight to dry weight ratio; DM, dry matter; OM, organic matter; CP, crude protein (nitrogen factors of 5.13, 5.38, and 4.59 for green, brown and red macroalgae, respectively [Bach S J, Wang Y, McAllister T A (2008) Effect of feeding sun-dried seaweed (Ascophyllum nodosum) on fecal shedding of Escherichia coli o157:H7 by feedlot cattle and on growth performance of lambs. Animal Feed Science and Technology 142: 17-32], and 6.25 for cottonseed and Flinders grass hay); TL, total lipids; GE, gross energy; (n = 2).

TABLE 4

Elemental analysis (±SD) of freshwater and marine macroalgae species, decorticated cottonseed meal (DCS) and Flinders grass hay.

| Species | Al | As* | B | Ba | C | Ca^ | Cd* | Co^ | Cr^ |
|---|---|---|---|---|---|---|---|---|---|
| Freshwater green algae | | | | | | | | | |
| C vagabunda | 109 ± 1 | 1.1 ± 0.02 | 46.4 ± 1.1 | 64.1 ± 1.1 | 380193 ± 44 | 4150 ± 29 | | 0.35 ± 0.003 | 0.7 ± 0.04 |
| Oedogonium | 307 ± 2 | | 2.7 ± 0.5 | 54.2 ± 1.3 | 447447 ± 5 | 2850 ± 15 | | 0.53 ± 0.005 | 1.4 ± 0.04 |
| Spirogyra | 770 ± 8 | 10.4 ± 0.2 | 3.9 ± 0.45 | 2420 ± 69 | 372454 ± 419 | 16700 ± 157 | 0.08 ± 0.003 | 0.89 ± 0.014 | 0.1 ± 0.02 |

TABLE 4-continued

Elemental analysis (±SD) of freshwater and marine macroalgae species, decorticated cottonseed meal (DCS) and Flinders grass hay.

| Marine green algae | | | | | | | | | |
|---|---|---|---|---|---|---|---|---|---|
| Caulerpa | 34.1 ± 4.8 | 1.0 ± 0.04 | 18.5 ± 0.8 | 6.7 ± 0.16 | 320232 ± 2128 | 3750 ± 13 | 0.06 ± 0.002 | 0.17 ± 0.002 | 0.3 ± 0.02 |
| Chaetomorpha | 68.4 ± 1.9 | 2.0 ± 0.04 | 176 ± 2 | 2.7 ± 0.02 | 322278 ± 2190 | 4540 ± 18 | 0.49 ± 0.014 | 0.28 ± 0.005 | 0.3 ± 0.01 |
| Cladophora | 2580 ± 25 | 7.0 ± 0.13 | 292 ± 4 | 17.2 ± 0.2 | 361389 ± 990 | 7790 ± 36 | 0.11 ± 0.002 | 1.39 ± 0.01 | 2.6 ± 0.05 |
| C. patentiramea | 3320 ± 18 | 3.7 ± 0.05 | 212 ± 2 | 26.6 ± 0.4 | 292572 ± 2316 | 17400 ± 182 | 0.18 ± 0.002 | 4.36 ± 0.05 | 3.7 ± 0.1 |
| Derbesia | 55 ± 3.7 | 5.5 ± 0.12 | 43 ± 1.4 | 3.2 ± 0.03 | 449668 ± 2616 | 2740 ± 19 | 0.29 ± 0.009 | 0.67 ± 0.012 | 0.3 ± 0.03 |
| Ulva sp. | 470 ± 6 | | 591 ± 5 | 6.0 ± 0.07 | 322491 ± 2200 | 10100 ± 100 | 0.48 ± 0.004 | 0.34 ± 0.005 | 1.1 ± 0.04 |
| U. ohnoi | 24.9 ± 2.2 | | 61.6 ± 2.3 | 2.7 ± 0.05 | 291623 ± 1274 | 4540 ± 34 | 0.24 ± 0.006 | 0.48 ± 0.013 | 0.9 ± 0.03 |
| Brown algae | | | | | | | | | |
| Cystoseira | 1120 ± 10 | 148 ± 3 | 125 ± 2 | 13.9 ± 0.2 | 317347 ± 1114 | 16300 ± 164 | 0.41 ± 0.009 | 0.52 ± 0.011 | 0.6 ± 0.31 |
| Dictyota | 6890 ± 78 | 20.4 ± 0.3 | 136 ± 5 | 28.2 ± 0.8 | 332795 ± 2976 | 35200 ± 177 | 1.25 ± 0.02 | 1.38 ± 0.04 | 3.8 ± 0.03 |
| Hormophysa | 6860 ± 77 | 16.5 ± 0.3 | 55.4 ± 0.9 | 33.5 ± 0.6 | 296874 ± 3371 | 21500 ± 100 | 0.18 ± 0.005 | 1.09 ± 0.01 | 3.5 ± 0.05 |
| Padina | 1640 ± 26 | 79.5 ± 1.6 | 102 ± 1 | 17.2 ± 0.1 | 243383 ± 541 | 21200 ± 273 | 0.09 ± 0.001 | 0.36 ± 0.005 | 1 ± 0.02 |
| Sargassum | 1230 ± 20 | 54.5 ± 1.1 | 149 ± 2 | 18 ± 0.2 | 305020 ± 560 | 20200 ± 100 | 0.51 ± 0.014 | 0.61 ± 0.008 | 0.8 ± 0.03 |
| Colpomenia | 13200 ± 106 | 18.2 ± 0.3 | 28.2 ± 1.7 | 35.4 ± 0.4 | 270564 ± 1057 | 56300 ± 364 | 0.10 ± 0.005 | 1.49 ± 0.04 | 5.9 ± 0.13 |
| Red algae | | | | | | | | | |
| Asparagopsis | 360 ± 1 | 2.8 ± 0.05 | 159 ± 4 | 3.9 ± 0.04 | 383998 ± 598 | 6050 ± 34 | 0.52 ± 0.005 | 0.23 ± 0.005 | 0.6 ± 0.03 |
| Halymenia | 40.6 ± 1.5 | 16.9 ± 0.3 | 59.4 ± 1.2 | 0.9 ± 0.01 | 288515 ± 1153 | 3910 ± 30 | 2.79 ± 0.06 | 2.09 ± 0.04 | 0.2 ± 0.02 |
| Hypnea | 6660 ± 35 | 9.5 ± 0.16 | 149 ± 4 | 17 ± 0.3 | 219976 ± 1674 | 32200 ± 450 | 0.33 ± 0.008 | 1.02 ± 0.01 | 4.2 ± 0.11 |
| Laurencia | 5200 ± 60 | 10.7 ± 0.3 | 114 ± 3 | 9.8 ± 0.13 | 290681 ± 1558 | 26000 ± 196 | 0.31 ± 0.007 | 0.71 ± 0.012 | 2.8 ± 0.08 |
| DCS | 2.1 ± 0.1 | | 23.5 ± 1.4 | 1.5 ± 0.03 | 427763 ± 1922 | 1850 ± 18 | | 0.43 ± 0.016 | |
| Flinders grass | 759 ± 3 | | 9.6 ± 0.5 | 16.6 ± 0.2 | 389407 ± 1560 | 3490 ± 36 | | 0.19 ± 0.001 | 0.8 ± 0.02 |

| Species | Cu^ | Fe^ | H | K^ | Mg^ |
|---|---|---|---|---|---|
| Freshwater green algae | | | | | |
| C vagabunda | 8.2 ± 0.18 | 930 ± 7 | 57363 ± 174 | 33700 ± 104 | 2110 ± 13 |
| Oedogonium | 55.8 ± 2.1 | 1860 ± 16 | 66547 ± 477 | 13300 ± 109 | 2140 ± 49 |
| Spirogyra | 4.0 ± 0.12 | 385 ± 1 | 57617 ± 1139 | 5640 ± 62 | 3110 ± 43 |
| Marine green algae | | | | | |
| Caulerpa | 2.2 ± 0.04 | 40.6 ± 0.1 | 48077 ± 84 | 6390 ± 38 | 5800 ± 10 |
| Chaetomorpha | 21.3 ± 0.4 | 474 ± 3 | 48794 ± 447 | 86700 ± 316 | 6220 ± 69 |
| Cladophora | 93.8 ± 2.4 | 3390 ± 28 | 55033 ± 244 | 38600 ± 351 | 5320 ± 50 |
| C. patentiramea | 10.1 ± 0.1 | 4350 ± 11 | 42131 ± 1063 | 60300 ± 537 | 4990 ± 49 |
| Derbesia | 22.5 ± 0.5 | 1990 ± 10 | 66253 ± 1063 | 8990 ± 27 | 5050 ± 47 |
| Ulva sp. | 31 ± 0.5 | 766 ± 11 | 54847 ± 378 | 20500 ± 100 | 26700 ± 497 |
| U. ohnoi | 11.4 ± 0.2 | 110 ± 1 | 55415 ± 258 | 21600 ± 290 | 37800 ± 100 |
| Brown algae | | | | | |
| Cystoseira | 1.3 ± 0.04 | 698 ± 3 | 46413 ± 247 | 85500 ± 1960 | 7830 ± 52 |
| Dictyota | 6.9 ± 0.16 | 4600 ± 14 | 46808 ± 554 | 27000 ± 164 | 27000 ± 181 |
| Hormophysa | 9.2 ± 0.11 | 4420 ± 39 | 41653 ± 217 | 30800 ± 429 | 10900 ± 100 |
| Padina | 3.1 ± 0.06 | 997 ± 13 | 38562 ± 88 | 81300 ± 138 | 6810 ± 35 |
| Sargassum | 3.0 ± 0.07 | 801 ± 5 | 46314 ± 404 | 78100 ± 1060 | 7010 ± 80 |
| Colpomenia | 7.0 ± 0.15 | 8150 ± 19 | 38868 ± 538 | 80100 ± 1520 | 7480 ± 72 |
| Red algae | | | | | |
| Asparagopsis | 15.5 ± 0.2 | 997 ± 6 | 58657 ± 771 | 14700 ± 127 | 4730 ± 60 |
| Halymenia | 2.0 ± 0.06 | 75.1 ± 0.5 | 48842 ± 1371 | 36600 ± 172 | 9010 ± 19 |
| Hypnea | 5.3 ± 0.08 | 3790 ± 22 | 34898 ± 855 | 19300 ± 246 | 7020 ± 37 |
| Laurencia | 4.5 ± 0.06 | 2930 ± 18 | 44524 ± 13 | 12300 ± 100 | 6020 ± 53 |
| Cottonseed | 11.2 ± 0.2 | 112 ± 4 | 64058 ± 1140 | 15900 ± 109 | 7220 ± 12 |
| Flinders Grass | 3.4 ± 0.08 | 757 ± 6 | 53420 ± 8 | 7750 ± 148 | 1050 ± 14 |

| Species | Mn^ | Mo^ | N | Na^ |
|---|---|---|---|---|
| Freshwater green algae | | | | |
| C vagabunda | 578 ± 4 | 9.5 ± 0.1 | 54296 ± 742 | 2790 ± 10 |
| Oedogonium | 180 ± 3 | 2.1 ± 0.07 | 49219 ± 115 | 424 ± 7 |
| Spirogyra | 1320 ± 18 | 0.8 ± 0.03 | 14719 ± 419 | 38700 ± 604 |
| Marine green algae | | | | |
| Caulerpa | 5.3 ± 0.1 | 0.9 ± 0.08 | 32478 ± 17 | 82400 ± 806 |
| Chaetomorpha | 30.9 ± 0.6 | 1.5 ± 0.24 | 42552 ± 440 | 9950 ± 39 |

TABLE 4-continued

Elemental analysis (±SD) of freshwater and marine macroalgae species, decorticated cottonseed meal (DCS) and Flinders grass hay.

| | | | | |
|---|---|---|---|---|
| Cladophora | 92.5 ± 1 | 2.2 ± 0.05 | 52462 ± 144 | 3850 ± 23 |
| C. patentiramea | 5480 ± 90 | 2.1 ± 0.13 | 23887 ± 1183 | 3430 ± 38 |
| Derbesia | 55.4 ± 0.9 | 0.8 ± 0.01 | 66072 ± 130 | 8180 ± 74 |
| Ulva sp. | 34.5 ± 0.5 | 0.6 ± 0.01 | 47075 ± 494 | 8430 ± 188 |
| U. ohnoi | 10.0 ± 0.4 | 0.4 ± 0.02 | 43018 ± 227 | 5390 ± 74 |
| Brown algae | | | | |
| Cystoseira | 26.4 ± 0.2 | 1.2 ± 0.08 | 18332 ± 352 | 17100 ± 105 |
| Dictyota | 458 ± 5 | 1.1 ± 0.07 | 17917 ± 683 | 5310 ± 33 |
| Hormophysa | 179 ± 2 | 1.1 ± 0.02 | 7897 ± 183 | 6010 ± 72 |
| Padina | 27 ± 0.5 | 1.3 ± 0.22 | 10966 ± 438 | 18400 ± 100 |
| Sargassum | 59.7 ± 0.5 | 1.7 ± 0.16 | 8430 ± 64 | 11700 ± 199 |
| Colpomenia | 156 ± 2 | 1.3 ± 0.02 | 14067 ± 258 | 15700 ± 112 |
| Red algae | | | | |
| Asparagopsis | 34.2 ± 0.2 | 1.6 ± 0.03 | 55508 ± 294 | 12800 ± 167 |
| Halymenia | 8.3 ± 0.1 | 0.7 ± 0.03 | 21685 ± 388 | 36000 ± 290 |
| Hypnea | 115 ± 2 | 1.0 ± 0.07 | 14348 ± 159 | 54400 ± 504 |
| Laurencia | 63.8 ± 0.8 | 1.1 ± 0.08 | 18878 ± 1417 | 64000 ± 1200 |
| Cottonseed | 17.2 ± 1.2 | 1.6 ± 0.06 | 79583 ± 641 | 2080 ± 12 |
| Flinders Grass | 54.8 ± 0.8 | 1.8 ± 0.1 | 4412 ± 698 | 868 ± 7 |

| Species | Ni^ | O | P | Pb* | S^ | Se^ | Sr* | V | Zn^ |
|---|---|---|---|---|---|---|---|---|---|
| Freshwater green algae | | | | | | | | | |
| C vagabunda | 0.4 ± 0.01 | 353500 ± 141 | 1380 ± 24 | 0.5 ± 0.01 | 11227 ± 812 | 1.07 ± 0.12 | 31.7 ± 0.6 | 0.35 ± 0.01 | 15.5 ± 0.3 |
| Oedogonium | 0.8 ± 0.01 | 373300 ± 1273 | 4950 ± 32 | 1.4 ± 0.02 | 2900 ± 420 | | 17.7 ± 0.3 | 0.60 ± 0.01 | 51.4 ± 0.5 |
| Spirogyra | 0.6 ± 0.02 | 412450 ± 1202 | 274 ± 21 | 0.3 ± 0.002 | 3100 ± 170 | | 132 ± 3 | 0.86 ± 0.02 | 10.9 0.1 |
| Marine green algae | | | | | | | | | |
| Caulerpa | 1.7 ± 0.06 | 326650 ± 1909 | | 0.1 ± 0.003 | 22051 ± 891 | 1.98 ± 0.18 | 67.4 ± 1.8 | 0.91 ± 0.04 | 13.6 ± 0.2 |
| Chaetomorpha | 1.5 ± 0.03 | 363600 ± 1131 | | 0.3 ± 0.003 | 21415 ± 554 | | 47.1 ± 0.5 | 1.36 ± 0.01 | 64 ± 0.6 |
| Cladophora | 2.9 ± 0.05 | 330150 ± 212 | 2320 ± 38 | 0.7 ± 0.008 | 21021 ± 2074 | | 67.6 ± 1.7 | 4.55 ± 0.06 | 30 ± 0.5 |
| C. patentiramea | 4.7 ± 0.04 | 336700 ± 2970 | | 1.5 ± 0.02 | 32778 ± 839 | 2.51 ± 0.19 | 131 ± 1 | 5.19 ± 0.13 | 19.1 ± 0.4 |
| Derbesia | 1.7 ± 0.06 | 312100 ± 1273 | 2340 ± 47 | 1.3 ± 0.01 | 12308 ± 538 | 1.39 ± 0.05 | 31.3 ± 0.6 | 1.17 ± 0.03 | 34.5 ± 0.8 |
| Ulva sp. | 1.9 ± 0.01 | 379000 ± 1131 | 1860 ± 47 | 0.3 ± 0.006 | 28244 ± 827 | 1.25 ± 0.16 | 117 ± 2 | 1.1 ± 0.01 | 25.3 ± 0.3 |
| U. ohnoi | 3.0 ± 0.08 | 459350 ± 1768 | | 0.1 ± 0.003 | 57464 ± 1055 | | 49.7 ± 1.1 | 0.29 ± 0.01 | 39.6 ± 0.6 |
| Brown algae | | | | | | | | | |
| Cystoseira | 1.4 ± 0.05 | 386000 ± 1414 | | 0.3 ± 0.005 | 13138 ± 837 | | 1230 ± 27 | 1.89 ± 0.04 | 13.6 ± 0.2 |
| Dictyota | 4.5 ± 0.09 | 360350 ± 71 | | 3.1 ± 0.01 | 11975 ± 247 | | 1180 ± 10 | 5.47 ± 0.08 | 99.5 ± 1.4 |
| Hormophysa | 4.0 ± 0.08 | 394350 ± 1344 | | 2.8 ± 0.02 | 13375 ± 780 | | 905 ± 34 | 5.34 ± 0.08 | 56.7 ± 0.5 |
| Padina | 2.7 ± 0.06 | 377450 ± 778 | | 0.5 ± 0.457 | 33734 ± 1514 | | 1500 ± 25 | 2.05 ± 0.04 | 10.5 ± 0.2 |
| Sargassum | 1.8 ± 0.05 | 384800 ± 566 | | 0.3 ± 0.004 | 9600 ± 1025 | 1.4 ± 0.21 | 1700 ± 27 | 1.72 ± 0.04 | 13.7 ± 0.2 |
| Colpomenia | 8.0 ± 0.1 | 324650 ± 2192 | | 2.4 ± 0.01 | 7200 ± 552 | | 1500 ± 34 | 9.41 ± 0.29 | 45.3 ± 0.6 |
| Red algae | | | | | | | | | |
| Asparagopsis | 1.6 ± 0.03 | 355300 ± 2687 | 70.5 ± 23.5 | 0.4 ± 0.006 | 26871 ± 442 | 38.8 ± 3.7 | 56.5 ± 1.3 | 0.90 ± 0.01 | 145 ± 2 |
| Halymenia | 0.7 ± 0.2 | 407550 ± 354 | | | 55744 ± 1350 | 1.16 ± 0.15 | 71.7 ± 1 | 0.93 ± 0.01 | 98 ± 1.8 |
| Hypnea | 5.1 ± 0.09 | 353500 ± 2687 | | 1.3 ± 0.02 | 41576 ± 3596 | 4.32 ± 0.26 | 441 ± 7 | 10.6 ± 0.3 | 19.1 ± 0.4 |
| Laurencia | 4.4 ± 0.05 | 329950 ± 2333 | | 1.0 ± 0.021 | 27133 ± 735 | 18.9 ± 0.4 | 309 ± 6 | 5.65 ± 0.11 | 23.2 ± 0.3 |
| Cottonseed | 2.0 ± 0.04 | 331522 ± 1441 | 12700 ± 100 | 0.5 ± 0.007 | 3111 ± 155 | | 11.2 ± 0.1 | | 52.9 ± 1.8 |
| Flinders Grass | 0.7 ± 0.01 | 399000 ± 1131 | | 0.13 ± 0.003 | 1676 ± 183 | | 47 ± 0.7 | 0.92 ± 0.01 | 36.6 ± 0.2 |

Parameters were calculated in mg · kg$^{-1}$ DM; (n = 2-5);
*elements toxic or not required by beef cattle;
^minerals required by beef cattle;
Numbers in bold are very close or above the maximum tolerable concentrations for beef cattle (NRC, 2000);

TABLE 5

FAME profile (±SD) of macroalgae species, decorticated cottonseed meal (DCS) and Flinders grass hay.

| | C. vagabunda | Oedogonium | Spirogyra | C. aulerpa | Chaetomorpha | C. coelothrix |
|---|---|---|---|---|---|---|
| C 12:0 | 0.21 ± 0.04 | | | | | |
| C 14:0 | 5.59 ± 0.27 | 0.56 ± 0.04 | 0.33 ± 0.04 | 0.46 ± 0.03 | 1.67 ± 0.04 | 2.34 ± 0.16 |
| C 15:0 | 0.51 ± 0.05 | 0.59 ± 0.03 | 0.26 ± 0.04 | 0.29 ± 0.02 | 0.34 ± 0.02 | 0.39 ± 0.05 |
| C 16:0 | 8.67 ± 0.65 | 11.46 ± 0.37 | 7.39 ± 0.65 | 7.81 ± 0.16 | 5.08 ± 0.05 | 7.20 ± 0.27 |
| C16:1 (7) | 0.94 ± 0.04 | 0.48 ± 0.03 | 0.66 ± 0.06 | 0.33 ± 0.05 | 0.41 ± 0.02 | 0.45 ± 0.03 |
| C 16:1 (9) | 1.08 ± 0.00 | 0.70 ± 0.33 | 0.47 ± 0.00 | 0.87 ± 0.02 | 0.62 ± 0.03 | 1.43 ± 0.03 |

TABLE 5-continued

FAME profile (±SD) of macroalgae species, decorticated cottonseed meal (DCS) and Flinders grass hay.

| | | | | | | |
|---|---|---|---|---|---|---|
| C16:2 (7,10) | 0.67 ± 0.07 | 0.94 ± 0.00 | 0.44 ± 0.05 | 0.69 ± 0.01 | 0.32 ± 0.02 | 0.48 ± 0.02 |
| C16:2 (9,12) | 3.95 ± 0.48 | 0.47 ± 0.02 | | | 1.81 ± 0.04 | 1.20 ± 0.10 |
| C 17:0 | | | 0.23 ± 0.03 | 0.23 ± 0.02 | | |
| C 17:1 (cis - 10) | 0.32 ± 0.04 | | | | | |
| C16:3 (7,10,13) | 0.44 ± 0.05 | 2.75 ± 0.02 | 2.27 ± 0.25 | 2.16 ± 0.12 | | |
| C16:4 (4,7,10,13) | 0.49 ± 0.08 | 4.99 ± 0.14 | | | 1.13 ± 0.05 | 2.03 ± 0.18 |
| C 18:0 | 0.30 ± 0.03 | 0.61 ± 0.01 | 0.34 ± 0.05 | 0.30 ± 0.02 | 0.23 ± 0.01 | 0.43 ± 0.05 |
| C 18:1 (9)cis | 7.97 ± 0.60 | 1.74 ± 0.04 | 0.97 ± 0.13 | 0.32 ± 0.03 | 0.76 ± 0.02 | 2.08 ± 0.15 |
| C 18:1 (11) | 1.39 ± 0.05 | 0.70 ± 0.02 | 0.35 ± 0.05 | 0.54 ± 0.02 | 0.74 ± 0.02 | 2.36 ± 0.11 |
| C 18:2 (9,12) Cis | 6.58 ± 0.43 | 4.23 ± 0.08 | 2.51 ± 0.17 | 1.92 ± 0.02 | 4.85 ± 0.09 | 4.92 ± .024 |
| C18:3 (6,9,12) | 3.42 ± 0.26 | 0.63 ± 0.04 | 0.63 ± 0.00 | 0.46 ± 0.02 | 0.29 ± 0.02 | 0.24 ± 0.00 |
| C 18:3 (9,12,15) | 1.26 ± 0.10 | 15.80 ± 0.57 | 6.59 ± 0.64 | 4.25 ± 0.02 | 0.67 ± 0.03 | 1.41 ± 0.10 |
| C18:4 (6,9,12,15) | 0.30 ± 0.03 | 0.84 ± 0.02 | 0.58 ± 0.06 | 0.55 ± 0.01 | 0.43 ± 0.02 | 0.24 ± 0.02 |
| C 20:0 | | | | | | 0.18 ± 0.02 |
| C 20:1 (11) | 0.40 ± 0.05 | 0.57 ± 0.01 | | | | 0.18 ± 0.03 |
| C 20:2 (11,14) | 0.31 ± 0.04 | 0.41 ± 0.00 | 0.28 ± 0.04 | 0.24 ± 0.03 | 0.20 ± 0.02 | 0.20 ± 0.03 |
| C 21:0 | | | | 0.21 ± 0.07 | 0.19 ± 0.04 | 0.22 ± 0.09 |
| C 20:3 (8,11,14) | 0.48 ± 0.06 | 0.26 ± 0.00 | 0.26 ± 0.04 | 0.24 ± 0.02 | 0.21 ± 0.02 | 0.19 ± 0.03 |
| C 20:4 (5,8,11,14) | 2.79 ± 0.28 | 1.14 ± 0.05 | 0.98 ± 0.07 | 0.81 ± 0.04 | 0.52 ± 0.04 | 0.59 ± 0.05 |
| C 20:3 (11,14,17) | | 0.66 ± 0.01 | 0.35 ± 0.01 | 0.22 ± 0.02 | | |
| C 22:0 | 0.26 ± 0.03 | | 0.52 ± 0.04 | | | 0.21 ± 0.03 |
| C 20:5 (5,8,11,14,17) | 0.46 ± 0.07 | 2.01 ± 0.00 | 1.12 ± 0.07 | 1.32 ± 0.05 | 0.37 ± 0.03 | 0.75 ± 0.07 |
| C 24:0 | 0.79 ± 0.02 | | 0.33 ± 0.03 | 0.87 ± 0.06 | 0.28 ± 0.02 | 0.40 ± 0.03 |
| Total FA | 49.60 ± 3.76 | 57.77 ± 0.70 | 27.88 ± 2.55 | 25.50 ± 0.64 | 21.09 ± 0.45 | 30.83 ± 1.82 |
| PUFA | 21.15 ± 1.93 | 35.14 ± 0.77 | 16.01 ± 1.41 | 13.27 ± 0.30 | 10.79 ± 0.38 | 12.67 ± 0.94 |
| MUFA | 12.11 ± 0.77 | 4.40 ± 0.44 | 2.45 ± 0.24 | 2.27 ± 0.15 | 2.71 ± 0.04 | 7.01 ± 0.27 |
| SFA | 16.35 ± 1.06 | 13.22 ± 0.37 | 9.41 ± 0.89 | 10.16 ± 0.27 | 7.78 ± 0.07 | 11.37 ± 0.70 |

| | C. patentiramea | Derbesia | Ulva sp. | U. ohnoi | Cystoseira |
|---|---|---|---|---|---|
| C 12:0 | | 0.44 ± 0.02 | | | |
| C 14:0 | 1.40 ± 0.09 | 1.28 ± 0.06 | 0.32 ± 0.02 | 0.24 ± 0.01 | 0.86 ± 0.02 |
| C 15:0 | 0.27 ± 0.03 | 0.87 ± 0.02 | 0.46 ± 0.03 | 0.33 ± 0.02 | 0.26 ± 0.01 |
| C 16:0 | 5.18 ± 0.25 | 17.29 ± 0.79 | 7.95 ± 0.15 | 5.37 ± 0.01 | 6.19 ± 0.40 |
| C16:1 (7) | | 0.92 ± 0.01 | 0.94 ± 0.02 | 0.56 ± 0.06 | 0.30 ± 0.02 |
| C 16:1 (9) | 0.57 ± 0.04 | 1.08 ± 0.01 | 0.46 ± 0.05 | 0.73 ± 0.05 | 0.83 ± 0.06 |
| C16:2 (7,10) | 0.29 ± 0.02 | 0.52 ± 0.03 | 0.37 ± 0.03 | | |
| C16:2 (9,12) | 0.51 ± 0.05 | | | | |
| C 17:0 | | 0.26 ± 0.01 | 0.25 ± 0.03 | 0.22 ± 0.02 | 0.21 ± 0.01 |
| C 17:1 (cis - 10) | | 0.28 ± 0.00 | 0.24 ± 0.01 | 0.26 ± 0.02 | |
| C16:3 (7,10,13) | | 3.64 ± 0.12 | 1.01 ± 0.07 | | |
| C16:4 (4,7,10,13) | 0.47 ± 0.06 | | 1.60 ± 0.12 | 0.62 ± 0.01 | |
| C 18:0 | 0.32 ± 0.04 | 0.61 ± 0.04 | 0.32 ± 0.03 | 0.26 ± 0.02 | 0.32 ± 0.01 |
| C 18:1 (9)cis | 1.63 ± 0.04 | 2.13 ± 0.12 | 0.39 ± 0.04 | 0.22 ± 0.04 | 2.24 ± 0.02 |
| C 18:1 (11) | 1.32 ± 0.03 | 1.46 ± 0.03 | 0.97 ± 0.02 | 1.74 ± 0.02 | 0.30 ± 0.02 |
| C 18:2 (9,12) Cis | 1.50 ± 0.05 | 2.56 ± 0.15 | 1.89 ± 0.09 | 0.39 ± 0.03 | 0.90 ± 0.03 |
| C18:3 (6,9,12) | | 0.80 ± 0.04 | 0.29 ± 0.00 | 0.23 ± 0.02 | 0.29 ± 0.01 |
| C 18:3 (9,12,15) | 0.45 ± 0.02 | 7.96 ± 0.49 | 5.29 ± 0.36 | 1.17 ± 0.02 | 1.04 ± 0.06 |
| C18:4 (6,9,12,15) | | 0.99 ± 0.01 | 0.84 ± 0.03 | 1.34 ± 0.01 | 0.78 ± 0.04 |
| C 20:0 | | 0.22 ± 0.00 | | | |
| C 20:1 (11) | | 0.23 ± 0.02 | | | |
| C 20:2 (11,14) | | | | | 0.19 ± 0.02 |
| C 21:0 | | | | | |
| C 20:3 (8,11,14) | | 0.30 ± 0.03 | 0.33 ± 0.04 | | 0.34 ± 0.00 |
| C 20:4 (5,8,11,14) | 0.77 ± 0.05 | 1.42 ± 0.06 | 0.46 ± 0.04 | 0.17 ± 0.02 | 2.52 ± 0.07 |
| C 20:3 (11,14,17) | | | 0.19 ± 0.01 | 0.18 ± 0.03 | |
| C 22:0 | | 0.94 ± 0.07 | 0.47 ± 0.06 | 0.52 ± 0.03 | |
| C 20:5 (5,8,11,14,17) | 0.34 ± 0.04 | 0.96 ± 0.06 | 0.34 ± 0.02 | 0.20 ± 0.00 | 0.86 ± 0.06 |
| C 24:0 | 0.26 ± 0.01 | 1.58 ± 0.07 | 0.24 ± 0.03 | | 0.26 ± 0.02 |
| Total FA | 15.56 ± 0.78 | 48.74 ± 2.00 | 25.63 ± 1.14 | 14.75 ± 0.39 | 18.69 ± 0.72 |
| PUFA | 4.34 ± 0.19 | 19.16 ± 0.87 | 12.60 ± 0.81 | 4.30 ± 0.13 | 6.92 ± 0.28 |
| MUFA | 3.53 ± 0.11 | 6.09 ± 0.05 | 3.01 ± 0.01 | 3.51 ± 0.15 | 3.68 ± 0.07 |
| SFA | 7.70 ± 0.49 | 23.49 ± 1.07 | 10.02 ± 0.34 | 6.94 ± 0.11 | 8.10 ± 0.37 |

| | Dictyota | Hormophysa | Padina | Sargassum | Colpomenia | Asparagopsis |
|---|---|---|---|---|---|---|
| C 12:0 | | | | | | 0.19 ± 0.00 |
| C 14:0 | 2.29 ± 0.01 | 0.62 ± 0.02 | 0.76 ± 0.02 | 0.70 ± 0.01 | 1.51 ± 0.02 | 1.58 ± 0.04 |
| C 15:0 | 0.36 ± 0.01 | 0.25 ± 0.01 | 0.30 ± 0.02 | 0.26 ± 0.01 | 0.32 ± 0.00 | 0.30 ± 0.00 |
| C 16:0 | 7.15 ± 0.16 | 3.40 ± 0.17 | 5.06 ± 0.20 | 3.86 ± 0.11 | 5.34 ± 0.05 | 10.71 ± 0.22 |
| C16:1 (7) | 0.31 ± 0.00 | 0.21 ± 0.02 | 0.26 ± 0.02 | 0.30 ± 0.01 | 0.36 ± 0.05 | 0.22 ± 0.01 |
| C 16:1 (9) | 0.43 ± 0.01 | 0.52 ± 0.02 | 0.76 ± 0.03 | 0.69 ± 0.04 | 0.49 ± 0.02 | 0.51 ± 0.01 |
| C16:2 (7,10) | | | | | | 0.16 ± 0.00 |
| C16:2 (9,12) | | | | | | |
| C 17:0 | | 0.24 ± 0.01 | 0.22 ± 0.02 | 0.21 ± 0.01 | 0.20 ± 0.00 | 0.22 ± 0.00 |
| C 17:1 (cis - 10) | | | | | | |

TABLE 5-continued

FAME profile (±SD) of macroalgae species, decorticated cottonseed meal (DCS) and Flinders grass hay.

| | | | | | | |
|---|---|---|---|---|---|---|
| C16:3 (7,10,13) | | | | | | 0.27 ± 0.00 |
| C16:4 (4,7,10,13) | | 0.17 ± 0.01 | | | | 0.17 ± 0.00 |
| C 18:0 | 0.65 ± 0.00 | 0.28 ± 0.01 | 0.40 ± 0.03 | 0.27 ± 0.01 | 0.33 ± 0.01 | 0.38 ± 0.00 |
| C 18:1 (9)cis | 5.07 ± 0.04 | 1.55 ± 0.03 | 2.28 ± 0.03 | 1.39 ± 0.01 | 3.03 ± 0.02 | 1.38 ± 0.05 |
| C 18:1 (11) | 0.44 ± 0.01 | 0.32 ± 0.00 | 0.37 ± 0.02 | 0.29 ± 0.02 | 0.49 ± 0.02 | 0.80 ± 0.00 |
| C 18:2 (9,12) Cis | 0.74 ± 0.02 | 2.16 ± 0.07 | 0.75 ± 0.02 | 0.66 ± 0.01 | 0.53 ± 0.01 | 0.49 ± 0.02 |
| C18:3 (6,9,12) | 0.36 ± 0.00 | 0.44 ± 0.00 | 0.36 ± 0.01 | 0.32 ± 0.03 | 0.30 ± 0.01 | 0.35 ± 0.01 |
| C 18:3 (9,12,15) | 1.16 ± 0.01 | 0.67 ± 0.01 | 1.14 ± 0.01 | 0.81 ± 0.02 | 0.43 ± 0.01 | 0.71 ± 0.02 |
| C18:4 (6,9,12,15) | 3.40 ± 0.03 | 0.65 ± 0.02 | 2.30 ± 0.06 | 0.88 ± 0.02 | 0.72 ± 0.04 | 0.98 ± 0.02 |
| C 20:0 | 0.37 ± 0.02 | | 0.25 ± 0.01 | | 0.32 ± 0.00 | |
| C 20:1 (11) | | | | | | 0.23 ± 0.01 |
| C 20:2 (11,14) | | 0.39 ± 0.00 | | 0.21 ± 0.01 | | 0.26 ± 0.01 |
| C 21:0 | | | | | | 0.16 ± 0.00 |
| C 20:3 (8,11,14) | 0.36 ± 0.00 | 2.45 ± 0.16 | 0.47 ± 0.01 | 0.31 ± 0.02 | 0.24 ± 0.01 | 0.25 ± 0.00 |
| C 20:4 (5,8,11,14) | 2.21 ± 0.04 | 3.65 ± 0.11 | 2.08 ± 0.03 | 1.74 ± 0.01 | 1.42 ± 0.03 | 3.83 ± 0.58 |
| C 20:3 (11,14,17) | | | | | | |
| C 22:0 | | | | | 0.21 ± 0.01 | |
| C 20:5 (5,8,11,14,17) | 1.69 ± 0.03 | 0.57 ± 0.12 | 0.64 ± 0.03 | 0.74 ± 0.02 | 1.23 ± 0.01 | 2.65 ± 0.38 |
| C 24:0 | | 0.21 ± 0.00 | | 0.29 ± 0.06 | 0.30 ± 0.00 | 0.22 ± 0.02 |
| Total FA | 27.01 ± 0.12 | 18.77 ± 0.18 | 18.39 ± 0.17 | 13.93 ± 0.20 | 18.30 ± 0.34 | 27.28 ± 1.32 |
| PUFA | 9.93 ± 0.04 | 11.15 ± 0.25 | 7.73 ± 0.04 | 5.67 ± 0.13 | 4.86 ± 0.12 | 10.13 ± 1.04 |
| MUFA | 6.24 ± 0.04 | 2.61 ± 0.04 | 3.67 ± 0.02 | 2.67 ± 0.07 | 4.90 ± 0.13 | 3.53 ± 0.04 |
| SFA | 10.83 ± 0.11 | 5.01 ± 0.11 | 6.99 ± 0.11 | 5.58 ± 0.00 | 8.53 ± 0.10 | 13.77 ± 0.25 |

| | Halymenia | Laurencia | Hypnea | DCS | Flinders grass |
|---|---|---|---|---|---|
| C 12:0 | | | | | 0.30 ± 0.02 |
| C 14:0 | 0.25 ± 0.00 | 1.43 ± 0.05 | 0.90 ± 0.06 | 0.27 ± 0.00 | 0.26 ± 0.01 |
| C 15:0 | 0.23 ± 0.00 | 0.27 ± 0.08 | 0.24 ± 0.02 | | 0.18 ± 0.01 |
| C 16:0 | 6.55 ± 0.11 | 5.16 ± 0.30 | 4.19 ± 0.02 | 6.64 ± 0.03 | 1.14 ± 0.13 |
| C16:1 (7) | 0.30 ± 0.00 | | 0.22 ± 0.03 | | 0.19 ± 0.01 |
| C 16:1 (9) | 0.42 ± 0.05 | 0.56 ± 0.08 | 0.77 ± 0.03 | 0.31 ± 0.02 | |
| C16:2 (7,10) | | | | | |
| C16:2 (9,12) | | | | | 0.20 ± 0.01 |
| C 17:0 | | | 0.21 ± 0.03 | 0.19 ± 0.00 | |
| C 17:1 (cis - 10) | | | | | |
| C16:3 (7,10,13) | | | 0.21 ± 0.03 | | |
| C16:4 (4,7,10,13) | | | | | |
| C 18:0 | 0.23 ± 0.09 | 0.32 ± 0.01 | 0.28 ± 0.03 | 1.00 ± 0.00 | 0.36 ± 0.03 |
| C 18:1 (9)cis | 1.45 ± 0.03 | 1.44 ± 0.05 | 1.00 ± 0.06 | 4.63 ± 0.01 | 0.59 ± 0.12 |
| C 18:1 (11) | 0.61 ± 0.00 | 0.51 ± 0.03 | 0.39 ± 0.01 | | 0.20 ± 0.02 |
| C 18:2 (9,12) Cis | 0.27 ± 0.00 | 0.42 ± 0.01 | 0.30 ± 0.04 | 12.98 ± 0.15 | 1.07 ± 021 |
| C18:3 (6,9,12) | 0.26 ± 0.03 | 0.29 ± 0.05 | 0.26 ± 0.04 | | |
| C 18:3 (9,12,15) | | 0.23 ± 0.00 | 0.22 ± 0.04 | 0.23 ± 0.00 | 0.57 ± 0.03 |
| C18:4 (6,9,12,15) | | 0.31 ± 0.04 | 0.32 ± 0.02 | | |
| C 20:0 | | | | 0.25 ± 0.00 | 0.49 ± 0.06 |
| C 20:1 (11) | | | 0.19 ± 0.03 | | |
| C 20:2 (11,14) | | | | | |
| C 21:0 | | | | | 0.19 ± 0.01 |
| C 20:3 (8,11,14) | 0.20 ± 0.01 | 0.29 ± 0.02 | 0.22 ± 0.03 | | |
| C 20:4 (5,8,11,14) | 1.16 ± 0.07 | 1.58 ± 0.07 | 0.72 ± 0.05 | | |
| C 20:3 (11,14,17) | | | | | |
| C 22:0 | | | | | 0.38 ± 0.03 |
| C 20:5 (5,8,11,14,17) | 1.03 ± 0.04 | 3.25 ± 0.18 | 1.09 ± 0.04 | | |
| C 24:0 | | | 0.26 ± 0.02 | | 0.49 ± 0.03 |
| Total FA | 12.97 ± 0.18 | 16.06 ± 0.34 | 11.99 ± 0.51 | 26.51 ± 0.22 | 6.62 ± 0.66 |
| PUFA | 2.92 ± 0.15 | 6.37 ± 0.14 | 3.34 ± 0.28 | 13.21 ± 0.15 | 1.84 ± 0.19 |
| MUFA | 2.78 ± 0.01 | 2.51 ± 0.06 | 2.58 ± 0.10 | 4.95 ± 0.02 | 1.18 ± 0.15 |
| SFA | 7.27 ± 0.02 | 7.18 ± 0.26 | 6.07 ± 0.13 | 8.35 ± 0.04 | 3.80 ± 0.32 |

Parameters were calculated in mg · g$^{-1}$ DM; (n = 2); Total FA, total fatty acids; PUFA, polyunsaturated fatty acids; MUFA, monounsaturated fatty acids; SFA; saturated fatty acids

TABLE 6

Proximate analysis of substrates (measured in g/kg DM unless otherwise stated).

| Species | DM | OM | CP | TL | Carbohydrates | NDF | ADF | GE (MJ/Kg DM) | N | C | H | S | O |
|---|---|---|---|---|---|---|---|---|---|---|---|---|---|
| *Oedogonium* | 939.9 | 885.6 | 307.5 | 79.4 | 498.8 | 614.7 | 186.7 | 19.4 | 49.2 | 447.4 | 66.5 | 2.9 | 373.3 |
| *Asparagopsis* | 944.3 | 936.0 | 346.9 | 33.3 | 555.8 | 410.9 | 98.8 | 16.8 | 55.5 | 384.0 | 58.7 | 26.9 | 355.3 |
| Rhodes Grass | 902.2 | 859.4 | 166.9 | 26.0 | 666.7 | 749.6 | 400.7 | 17.3 | 26.7 | 425.8 | 58.6 | 2.0 | 419.7 |

TABLE 7

Post-fermentation parameters.

| Species | Concentration % | A maximal gas production (ml/g) | B lag period (h) | C specific gas production rate (ml/h) | ln(B)/C Inflexion point | TGP 24 h (ml/g OM) | TGP 72 h | DM deg (%) | OM deg (%) | pH |
|---|---|---|---|---|---|---|---|---|---|---|
| Asparagopsis | 0.07 | 234.9 | 1.97 | 0.08 | 8.9 | 175.6 | 232.6 | 68.5 | 66 | 6.64 |
|  | 0.125 | 231.4 | 1.94 | 0.08 | 8.7 | 169.7 | 229.5 | 68.5 | 66 | 6.64 |
|  | 0.25 | 239.6 | 1.95 | 0.08 | 8.9 | 173.5 | 237.4 | 67.9 | 66 | 6.63 |
|  | 0.5 | 229.7 | 2.05 | 0.07 | 10.0 | 159.2 | 226.9 | 65.1 | 64 | 6.69 |
|  | 1 | 184.1 | 1.87 | 0.08 | 7.9 | 138.99 | 182.5 | 68.1 | 66 | 6.65 |
|  | 2 | 176.3 | 1.85 | 0.08 | 7.3 | 138.05 | 175.5 | 60.8 | 60 | 6.65 |
|  | 5 | 177.0 | 1.80 | 0.07 | 7.9 | 130.97 | 175.5 | 56.4 | 56 | 6.68 |
|  | 10 | 170.2 | 1.67 | 0.06 | 8.0 | 119.23 | 167.4 | 53.8 | 53 | 6.68 |
|  | 17 | 154.7 | 1.57 | 0.06 | 8.2 | 102.58 | 150.3 | 45.1 | 47 | 6.73 |
| Oedogonium | 10 | 223.1 | 1.88 | 0.07 | 8.6 | 160.88 | 220.7 | 62.5 | 60 | 6.69 |
|  | 17 | 221.5 | 1.87 | 0.07 | 9.1 | 154.55 | 218.6 | 52.9 | 55 | 6.71 |
|  | 25 | 220.4 | 1.74 | 0.06 | 8.5 | 152.41 | 216.7 | 54.7 | 54 | 6.73 |
|  | 50 | 208.7 | 1.50 | 0.05 | 7.9 | 134.17 | 200.7 | 49.3 | 50 | 6.77 |
|  | 75 | 180.2 | 1.30 | 0.05 | 5.3 | 120.44 | 174.0 | 32.6 | 36 | 6.93 |
|  | 100 | 130.5 | 1.35 | 0.10 | 2.9 | 115.26 | 130.4 | 25.9 | 26 | 7.01 |
| Rhodes Grass | 100 | 231.9 | 1.98 | 0.07 | 9.8 | 159.47 | 228.7 | 61.6 | 61 | 6.63 |
| Blank | 0 | 74.5 | 1.1 | 0.1 | 1.0 | 67.93 | 75.2 | NA | NA | 7.16 |

TABLE 8

Mean short chain volatile fatty acid production after 72 h in vitro incubation.

| Species | Concentration % | Total VFA (mmol/l) | C2 % | C3 % | Iso C4 % | C4 % | Iso C5 % | C5 % | C2/C3 |
|---|---|---|---|---|---|---|---|---|---|
| Asparagopsis | 0.07 | 105.20 | 72.57 | 16.78 | 0.74 | 7.78 | 1.28 | 0.84 | 4.33 |
|  | 0.125 | 105.67 | 72.68 | 16.72 | 0.75 | 7.74 | 1.27 | 0.84 | 4.35 |
|  | 0.25 | 106.61 | 70.94 | 17.25 | 0.77 | 8.80 | 1.32 | 0.91 | 4.12 |
|  | 0.5 | 105.58 | 68.41 | 18.90 | 0.75 | 9.48 | 1.51 | 0.95 | 3.63 |
|  | 1 | 99.17 | 65.32 | 20.78 | 0.45 | 10.19 | 2.25 | 1.00 | 3.15 |
|  | 2 | 94.66 | 63.81 | 22.04 | 0.14 | 10.97 | 2.00 | 1.04 | 2.90 |
|  | 5 | 90.11 | 62.12 | 23.48 | 0.00 | 12.17 | 0.83 | 1.41 | 2.65 |
|  | 10 | 85.44 | 62.41 | 22.33 | 0.16 | 12.81 | 0.69 | 1.60 | 2.80 |
|  | 17 | 81.09 | 61.75 | 21.64 | 0.17 | 14.02 | 0.76 | 1.67 | 2.86 |
| Oedogonium | 10 | 103.65 | 72.98 | 16.63 | 0.78 | 7.45 | 1.33 | 0.83 | 4.39 |
|  | 17 | 103.18 | 72.05 | 16.32 | 0.84 | 8.53 | 1.37 | 0.89 | 4.41 |
|  | 25 | 99.58 | 71.79 | 16.28 | 0.83 | 8.78 | 1.43 | 0.89 | 4.42 |
|  | 50 | 97.01 | 72.99 | 15.42 | 0.86 | 8.41 | 1.44 | 0.88 | 4.74 |
|  | 75 | 93.06 | 73.21 | 14.63 | 0.82 | 9.06 | 1.39 | 0.88 | 5.01 |
|  | 100 | 80.47 | 72.56 | 15.40 | 0.89 | 8.63 | 1.52 | 1.00 | 4.73 |
| Rhodes Grass | 100 | 108.24 | 71.94 | 16.69 | 0.72 | 8.56 | 1.25 | 0.84 | 4.31 |
| Blank | 0 | 59.26 | 77.05 | 12.00 | 0.00 | 9.12 | 1.34 | 0.49 | 6.44 |

TABLE 9

Mean liveweight, dry matter intake (DMI), dose rates and methane production (DMI basis) for Brahman steers dosed intra-ruminally with a red macroalgae (±SD).

| Treatment | CONTROL | MACROALGAE |
|---|---|---|
| 1st Chamber measurement | | |
| No of animals | 2 | 4 |
| Liveweight (Kg) | 339.1 ± 22.16 | 371.3 ± 8.98 |
| DMI (Kg/d) - 7 days average | 5.17 ± 0.21 | 4.73 ± 0.19 |
| Algal dose (%) - before chambers | 0 | 1.71 ± 1.05 |
| Algal dose (%) - in chambers | 0 | 1.66 ± 1.07 |
| Length of treatment (days) | 0 | 15-18 |
| $CH_4$ (g/Kg DMI) - Day 1 | 15.44 ± 1.23 | 13.6 ± 2.05 |
| $CH_4$ (g/Kg DMI) - Day 2 | 16.79 ± 0.59 | 13.58 ± 1.44 |
| $CH_4$ (g/Kg DMI) - Mean | 16.12 ± 1.11 | 13.55 ± 1.74 |
| 2nd Chamber measurement | | |
| No of animals | 2 | 2 |
| Liveweight (Kg) | 324.7 ± 7.28 | 362 ± 11.55 |
| DMI (Kg/d) - 7 days average | 5.25 ± 0.84 | 5.44 ± 1.32 |
| Algal dose (%) - before chambers | 0 | 1.72 ± 0.96 |
| Algal dose (%) - in chambers | 0 | 2.04 ± 0.22 |
| Length of treatment (days) | 0 | 23-26 |
| $CH_4$ (g/Kg DMI) - Day 1 | 15.88 ± 2.14 | 14.01 ± 1.97 |
| $CH_4$ (g/Kg DMI) - Day 2 | 16.25 ± 0.21 | 13.42 ± 0.16 |
| $CH_4$ (g/Kg DMI) - Mean | 16.07 ± 1.26 | 13.7 ± 1.19 |
| 3rd Chamber measurement | | |
| No of animals | 2 | 2 |
| Liveweight (Kg) | 321.6 ± 4 | 361.5 ± 9.13 |
| DMI (Kg/d) - 7 days average | 5.55 ± 0.74 | 5.88 ± 0.87 |
| Algal dose (%) - before chambers | 0 | 1.88 ± 0.68 |
| Algal dose (%) - in chambers | 0 | 1.96 ± 0.2 |
| Length of treatment (days) | 0 | 31-34 |
| $CH_4$ (g/Kg DMI) - Day 1 | 15.28 ± 1.14 | 13.75 ± 1.03 |
| $CH_4$ (g/Kg DMI) - Day 2 | 15.49 ± 1.77 | 13.75 ± 2.97 |
| $CH_4$ (g/Kg DMI) - Mean | 15.38 ± 1.22 | 13.75 ± 1.81 |

TABLE 10

Mean dietary mass (DM) intake over 75 d and each experimental period for sheep fed a pelleted diet with and without a supplement of *Asparagopsis* at different inclusion levels.

| | *Asparagopsis* inclusion (% OM intake per day) | | | | | |
|---|---|---|---|---|---|---|
| | 0% | 0.5% | 1.0% | 2.0% | 3.0% | P-value |
| DM intake (0-75 d) | | | | | | |
| n | 11 | 13 | 14 | 14 | 10 | |
| Mean (7 d) Period 1 (23-29 d) | 1038 | 1057 | 1041 | 1054 | 1016 | 0.386* |
| n | 4 | 4 | 5 | 5 | 3 | |
| Mean (7 d) Period 2 (44-50 d) | 976 | 1024 | 914 | 1011 | 925 | 0.771# |
| n | 3 | 4 | 4 | 4 | 3 | |
| Mean (7 d) Period 3 (65-71 d) | 1074 | 1086 | 1095 | 1081 | 1042 | 0.771# |
| n | 4 | 5 | 5 | 5 | 4 | |
| Mean (7 d) Live weight | 1070 | 1083 | 1097 | 1078 | 1036 | 0.771# |
| Mean (kg) | 68.7 | 69.1 | 68.6 | 68.8 | 67.1 | 0.390* |

Fixed term for *Asp.* X time effect,
*Fixed term for *Asp* effect only

TABLE 11

Mean ruminal fermentation parameters for sheep fed a pelleted diet with and without a supplement of *Asparagopsis* at different inclusion levels[1]

| | *Asparagopsis* inclusion (% OM intake per day) | | | | | P-value[2] | |
|---|---|---|---|---|---|---|---|
| | Control | 0.5% | 1.0% | 2.0% | 3.0% | Treatment | Time |
| n | 11 | 13 | 14 | 14 | 11 | | |
| Total, mM | 92.0 | 86.5 | 74.9 | 69.1 | 65.4 | 0.006 | 0.097 |
| VFA proportions, % Total | | | | | | | |
| Acetate | 65.0 | 56.3 | 54.4 | 55.0 | 54.5 | <0.001 | 0.035 |
| Propionate | 20.8 | 27.7 | 31.5 | 30.8 | 32.0 | <0.001 | 0.026 |
| Butyrate | 11.6 | 13.0 | 11.2 | 11.1 | 10.3 | 0.017 | 0.287 |
| Iso-butyrate | 0.41 | 0.36 | 0.32 | 0.42 | 0.47 | 0.192 | 0.208 |
| Valerate | 1.00 | 1.50 | 1.66 | 1.87 | 1.80 | <0.001 | 0.237 |
| Iso-valerate | 0.76 | 0.46 | 0.34 | 0.55 | 0.53 | 0.022 | 0.577 |
| A:P[3] | 3.19 | 2.10 | 1.76 | 1.86 | 1.77 | <0.001 | 0.074 |

[1]Mean values shown are pooled means for three sampling events at approx 21 d intervals throughout the experimental period;
[2]Main effects only;
[3]Acetate:Propionate.

The claims defining the invention are as follows:

1. A methane reducing ruminant animal feed comprising a methane reducing amount of a methane reducing red macroalgae comprising *Asparagopsis* in combination with a ruminant animal feed.

2. A methane reducing ruminant animal feed according to claim 1 wherein the *Asparagopsis* is provided in a form in which the secondary metabolites remain effective.

3. A methane reducing ruminant animal feed according to claim 1 wherein the *Asparagopsis* is *Asparagopsis taxiformis* and/or *Asparagopsis armata*.

4. An anti-methanogenic ruminant animal feed according to claim 1 wherein the feed comprises at least 0.067% *Asparagopsis* of organic matter of the feed.

5. An anti-methanogenic ruminant animal feed according to claim 1 wherein the feed comprises at least 0.125% *Asparagopsis* of organic matter of the feed.

6. An anti-methanogenic ruminant animal feed according to claim 1 wherein the feed comprises at least 0.25% *Asparagopsis* of organic matter of the feed.

7. An anti-methanogenic ruminant animal feed according to claim 1 wherein the feed comprises at least 0.5% *Asparagopsis* of organic matter of the feed.

8. An anti-methanogenic ruminant animal feed according to claim 1 wherein the feed comprises at least 1% *Asparagopsis* of organic matter of the feed.

9. A method of making a methane reducing ruminant animal feed comprising
adding a methane reducing animal feed supplement comprising a methane reducing amount of a methane reducing red macroalgae to a ruminant animal feed,
wherein the methane reducing red macroalgae comprises *Asparagopsis*.

10. A method according to claim 9 wherein the *Asparagopsis* is provided in a form in which the secondary metabolites remain effective.

11. A method according to claim 10 wherein the *Asparagopsis* is *Asparagopsis taxiformis* and/or *Asparagopsis armata*.

12. A method methane reducing animal feed supplement according to claim 10 wherein the feed comprises at least 0.067% *Asparagopsis* of organic matter of the feed.

13. A method according to claim 10 wherein the feed comprises at least 0.125% *Asparagopsis* of organic matter of the feed.

14. A method according to claim 10 wherein the feed comprises at least 0.25% *Asparagopsis* of organic matter of the feed.

15. A method according to claim 10 wherein the feed comprises at least 0.5% *Asparagopsis* of organic matter of the feed.

16. A method according to claim 10 wherein the feed comprises at least 1% *Asparagopsis* of organic matter of the feed.

17. A method of making a methane reducing animal feed comprising adding a methane reducing animal feed supplement consisting of a methane reducing red macroalgae, wherein the methane reducing red macroalgae is *Asparagopsis*, to a ruminant animal feed.

18. A method according to claim 17 wherein the *Asparagopsis* is provided in a form in which the secondary metabolites remain effective.

19. A method according to claim 17 wherein the feed comprises at least 0.067% *Asparagopsis* of organic matter of the feed.

* * * * *